US011672888B2

(12) United States Patent
Anikeeva et al.

(10) Patent No.: US 11,672,888 B2
(45) Date of Patent: Jun. 13, 2023

(54) STRUCTURES WITH COMPLEX GEOMETRIES AND CONTROLLED POROSITY IN MICROMETER TO METER DIMENSIONS PRODUCED AT LARGE SCALE

(71) Applicant: Massachusetts Institute of Technology, Cambridge, MA (US)

(72) Inventors: Polina Olegovna Anikeeva, Somerville, MA (US); Dena Shahriari, Boston, MA (US); Yoel Fink, Brookline, MA (US); Zi Jie Gabriel Loke, Cambridge, MA (US); Ian James Tafel, Jamaica Plain, MA (US)

(73) Assignees: Massachusetts Institute of Technology, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 448 days.

(21) Appl. No.: 16/695,932

(22) Filed: Nov. 26, 2019

(65) Prior Publication Data

US 2021/0170074 A1 Jun. 10, 2021

Related U.S. Application Data

(60) Provisional application No. 62/772,968, filed on Nov. 29, 2018.

(51) Int. Cl.
A61L 27/56 (2006.01)
A61L 27/36 (2006.01)
A61L 27/26 (2006.01)
A61L 27/16 (2006.01)

(52) U.S. Cl.
CPC .............. *A61L 27/56* (2013.01); *A61L 27/16* (2013.01); *A61L 27/26* (2013.01); *A61L 27/3675* (2013.01); *A61L 27/3687* (2013.01); *A61L 27/3691* (2013.01); *A61L 2430/32* (2013.01)

(58) Field of Classification Search
CPC ...... A61L 27/56; A61L 27/16; A61L 27/3675; A61L 2430/32; B33Y 80/00
See application file for complete search history.

(56) References Cited

U.S. PATENT DOCUMENTS

| 6,589,173 | B1 | 7/2003 | Mitragotri | |
| 6,716,225 | B2 | 4/2004 | Li et al. | |
| 10,426,872 | B2 | 10/2019 | Sakamoto et al. | |
| 2008/0119779 | A1 | 5/2008 | Babaev | |
| 2016/0155534 | A1* | 6/2016 | Fink .................. | D01D 5/30 252/500 |

FOREIGN PATENT DOCUMENTS

| WO | 2009153973 A1 | 12/2009 |
| WO | 2017062845 A1 | 4/2017 |

OTHER PUBLICATIONS

Tran et al. "A new generation of sodium chloride porogen for tissue engineering", Biotechnology and Applied Biochemistry, vol. 58, Issue 5, 2011, pp. 335-344 (Year: 2011).*
Angius et al., "A systematic review of animal models used to study nerve regeneration in tissue-engineered scaffolds." Biomaterials 33.32 (2012): 8034-8039.
Annabi et al., "Controlling the porosity and microarchitecture of hydrogels for tissue engineering." Tissue Engineering Part B: Reviews 16.4 (2010): 371-383.
Baino et al., "Bioactive glass-based materials with hierarchical porosity for medical applications: review of recent advances." Acta biomaterialia 42 (2016): 18-32.
Behbehani et al., "Pre-clinical evaluation of advanced nerve guide conduits using a novel 3D in vitro testing model." International Journal of Bioprinting 4.1 (2018). 13 pages.
Bellamkonda, "Peripheral nerve regeneration: an opinion on channels, scaffolds and anisotropy." Biomaterials 27.19 (2006): 3515-3518.
Canales et al., "Multifunctional fibers for simultaneous optical, electrical and chemical interrogation of neural circuits in vivo." Nature biotechnology 33.3 (2015): 277. 10 pages.
Ciaramitaro et al., "Traumatic peripheral nerve injuries: epidemiological findings, neuropathic pain and quality of life in 158 patients." Journal of the Peripheral Nervous System 15.2 (2010): 120-127.
Cosson et al., "Concise review: tailoring bioengineered scaffolds for stem cell applications in tissue engineering and regenerative medicine." Stem cells translational medicine 4.2 (2015): 156-164.
De Ruiter et al., "Designing ideal conduits for peripheral nerve repair." Neurosurgical focus 26.2 (2009): E5. 9 pages.
Den Dunnen et al., "Long-term evaluation of degradation and foreign-body reaction of subcutaneously implanted poly(DL-lactide-ε-caprolactone)." Journal of Biomedical Materials Research: An Official Journal of The Society for Biomaterials and The Japanese Society for Biomaterials 36.3 (1997): 337-346.
Duan et al., "Water-resistant porous coordination polymers for gas separation." Coordination Chemistry Reviews 332 (2017): 48-74.
Eshraghi et al., "Mechanical and microstructural properties of polycaprolactone scaffolds with one-dimensional, two-dimensional, and three-dimensional orthogonally oriented porous architectures produced by selective laser sintering." Acta biomaterialia 6.7 (2010): 2467-2476.
Führmann et al., "The role of biomaterials in overcoming barriers to regeneration in the central nervous system." Biomedical Materials 13.5 (2018): 050201. 4 pages.

(Continued)

*Primary Examiner* — James W Rogers
(74) *Attorney, Agent, or Firm* — Smith Baluch LLP

(57) ABSTRACT

Methods for generating porous scaffolds may include tuning a porogen/crystallite's particle size to a desired range and mixing the crystallite particles with a polymer solution. The mixture is then cast to form films. The films are rolled and consolidated around another inner material to create a preform, which is then thermally drawn. The inner material and the porogen can be selectively removed to obtain porous constructs/fibers. The structures can be fuse-printed to produce complex tissue scaffolds with dimensions up to several centimeters and beyond.

17 Claims, 40 Drawing Sheets

(56) References Cited

OTHER PUBLICATIONS

Grena et al., "Thermally-drawn fibers with spatially-selective porous domains." Nature communications 8.1 (2017): 1-8.
Guvendiren et al., "Designing biomaterials for 3D printing." ACS biomaterials science & engineering 2.10 (2016): 1679-1693.
Jafari et al., "Polymeric scaffolds in tissue engineering: a literature review." Journal of Biomedical Materials Research Part B: Applied Biomaterials 105.2 (2017): 431-459.
Jeon et al., "Fabrication of three-dimensional porous carbon scaffolds with tunable pore sizes for effective cell confinement." Carbon 130 (2018): 814-821.
Jiang et al., "Electrospinning of polymer nanofibers fortissue regeneration." Progress in polymer Science 46 (2015): 1-24.
Johnson et al., "3D printed anatomical nerve regeneration pathways." Advanced functional materials 25.39 (2015): 6205-6217.
Kameyama et al., "Morphologic features of the normal human cadaveric spinal cord." Spine 21.11 (1996): 1285-1290.
Kehoe et al., "FDA approved guidance conduits and wraps for peripheral nerve injury: a review of materials and efficacy." Injury 43.5 (2012): 553-572.
Khudiyev et al., "Electrostrictive microelectromechanical fibres and textiles." Nature communications 8.1 (2017): 1-7.
Khudiyev et al., "Sub-micrometer surface-patterned ribbon fibers and textiles." Advanced Materials 29.22 (2017): 1605868. 6 pages.
Koppes et al., "Thermally drawn fibers as nerve guidance scaffolds." Biomaterials 81 (2016): 27-35.
Lu et al., "Flexible and stretchable nanowire-coated fibers for optoelectronic probing of spinal cord circuits." Science advances 3.3 (2017): e1600955. 9 pages.
Lundborg, "A 25-year perspective of peripheral nerve surgery: evolving neuroscientific concepts and clinical significance." The Journal of hand surgery 25.3 (2000): 391-414.
Martin et al., "The role of bioreactors in tissue engineering." Trends in Biotechnology 22.2 (2004): 80-86.
Materials Research Society 2017 MRS Fall Meeting & Exhibit. Nov. 29, 2017. 3 pages.
Maurin et al., "The new age of MOFs and of their porous-related solids." Chemical Society Reviews 46.11 (2017): 3104-3107.
Mobini et al., "Recent advances in strategies for peripheral nerve tissue engineering." Current Opinion in Biomedical Engineering 4 (2017): 134-142.
Mosadegh-Sedghi et al., "Highly hydrophobic microporous low-density polyethylene hollow fiber membranes by melt-extrusion coupled with salt-leaching technique." Polymers for advanced technologies 24.6 (2013): 584-592.
Padaki et al., "Membrane technology enhancement in oil-water separation. A review." Desalination 357 (2015): 197-207.
Park et al., "One-step optogenetics with multifunctional flexible polymer fibers." Nature neuroscience 20.4 (2017): 612.
Park et al., "Optogenetic control of nerve growth." Scientific reports 5 (2015): 9669. 9 pages.
Particles Leaching. Electrospintech Aug. 27, 2012. Accessed at http://electrospintech.com/particles-leaching.html#.W_1LtUxFyUk on May 20, 2020. 3 pages.
Pawar et al., "Increasing capillary diameter and the incorporation of gelatin enhance axon outgrowth in alginate-based anisotropic hydrogels." Acta biomaterialia 7.7 (2011): 2826-2834.
Petcu et al., "3D printing strategies for peripheral nerve regeneration." Biofabrication 10.3 (2018): 032001. 22 pages.
Sarker et al., "Strategic design and fabrication of nerve guidance conduits for peripheral nerve regeneration." Biotechnology journal 13.7 (2018): 1700635. 16 pages.
Schuh, How Grain Boundary Segregation Enables 3D Printing of Bulk Nanostructured Metals. ASM Boston Chapter, Boston, MA May 24, 2018. 4 pages.
Shahriari et al., "Characterizing the degradation of alginate hydrogel for use in multilumen scaffolds for spinal cord repair." Journal of Biomedical Materials Research Part A 104.3 (2016): 611-619.
Shahriari et al., "Hierarchically ordered porous and high-volume polycaprolactone microchannel scaffolds enhanced axon growth in transected spinal cords." Tissue Engineering Part A 23.9-10 (2017): 415-425.
Shahriari et al., "Peripheral nerve growth within a hydrogel microchannel scaffold supported by a kink-resistant conduit." Journal of Biomedical Materials Research Part A 105.12 (2017): 3392-3399.
Shahriari et al., "Scalable Fabrication of Porous Microchannel Nerve Guidance Scaffolds with Complex Geometries." Advanced Materials 31.30 (2019): 1902021. 8 pages.
Stokols et al., "Templated agarose scaffolds support linear axonal regeneration." Tissue engineering 12.10 (2006): 2777-2787.
Thomas et al., "Channel density and porosity of degradable bridging scaffolds on axon growth after spinal injury." Biomaterials 34.9 (2013): 2213-2220.
Tuinstra et al., "Multifunctional, multichannel bridges that deliver neurotrophin encoding lentivirus for regeneration following spinal cord injury." Biomaterials 33.5 (2012): 1618-1626.
Upasani et al., "Preparation and characterization of porous polyester fibres by salt leaching method." Journal of the Textile Institute 104.4 (2013): 351-356.
Wang et al., "Porous chitosan tubular scaffolds with knitted outer wall and controllable inner structure for nerve tissue engineering." Journal of Biomedical Materials Research Part A: An Official Journal of The Society for Biomaterials, The Japanese Society for Biomaterials, and The Australian Society for Biomaterials and the Korean Society for Biomaterials 79.1 (2006): 36-46.
Wintermantel et al., "Tissue engineering scaffolds using superstructures." Biomaterials 17.2 (1996): 83-91.
Yang et al., "Hierarchically porous materials: synthesis strategies and structure design." Chemical Society Reviews 46.2 (2017): 481-558.
Yao et al., "Salt-leached silk scaffolds with tunable mechanical properties." Biomacromolecules 13.11 (2012): 3723-3729.
Yin et al., "Toward biomimetic porous poly (ε-caprolactone) scaffolds: structural evolution and morphological control during solid phase extrusion." Composites Science and Technology 156 (2018): 192-202.
Yuan et al., "Integrating membrane filtration into bioelectrochemical systems as next generation energy-efficient wastewater treatment technologies for water reclamation: a review." Bioresource technology 195 (2015): 202-209.

* cited by examiner

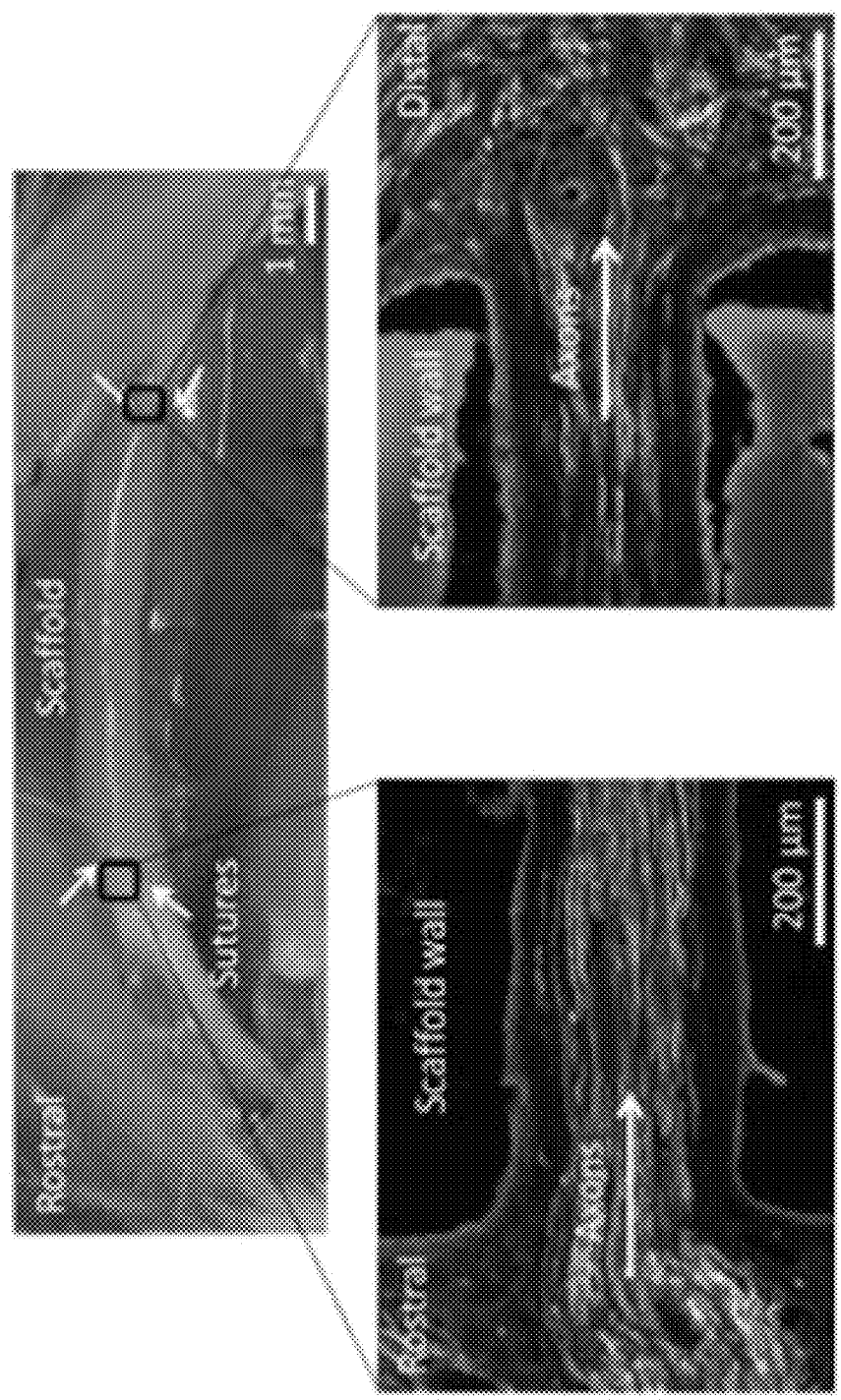
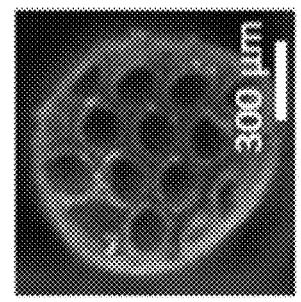
FIG. 1A
FIG. 1B
FIG. 1C
FIG. 1D

310
Ballmill and filter NaCl to desired size

315
Mix NaCl with polymer solution

320
Blade movement
Doctor blade films

325
Roll films, thermally draw and fuse-print

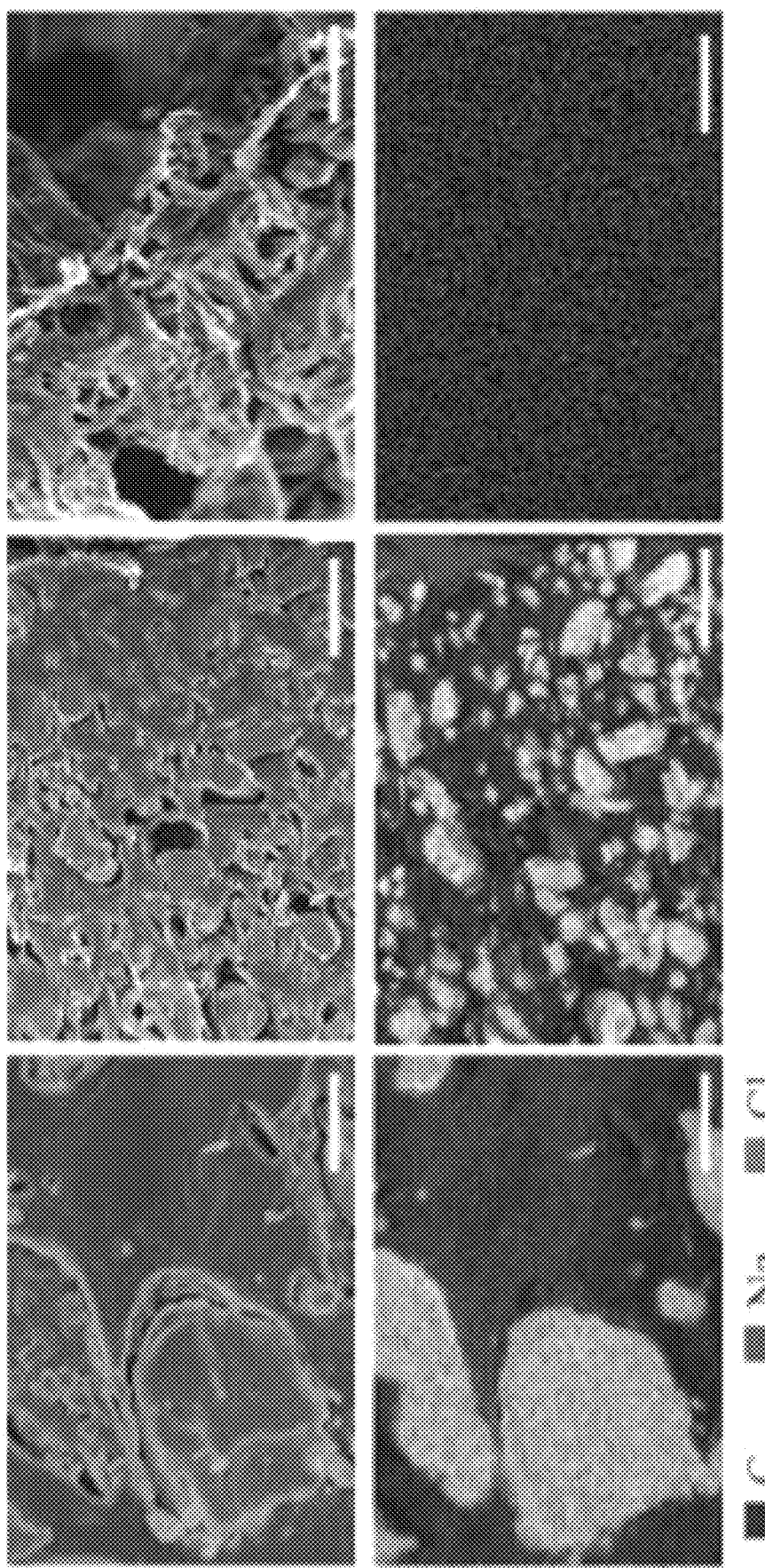

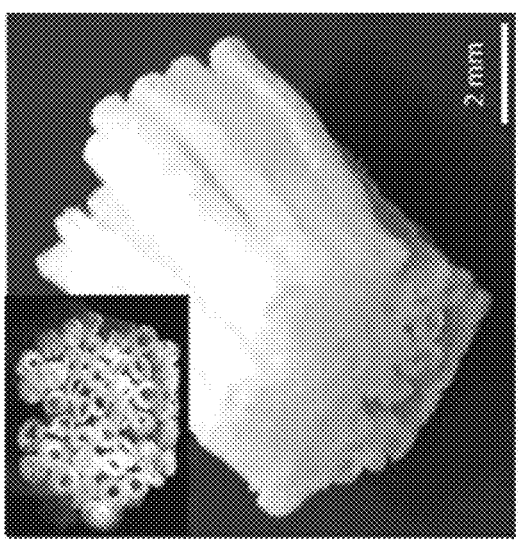
FIG. 5A  FIG. 5B  FIG. 5C  FIG. 5D
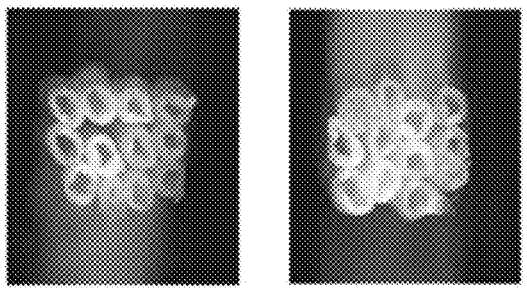
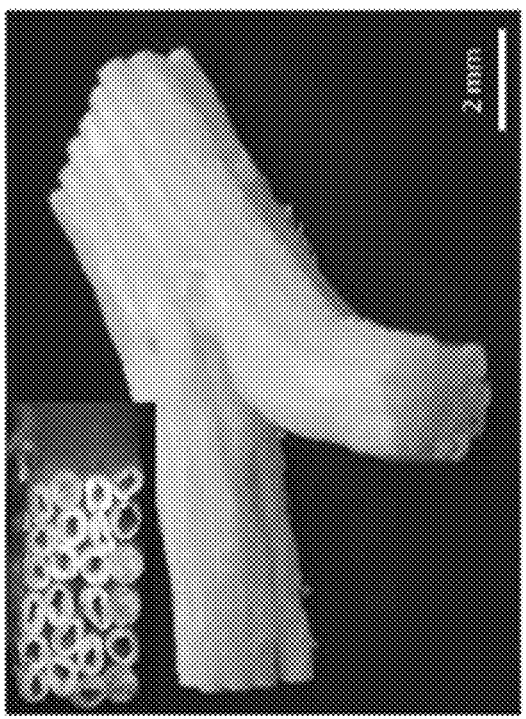
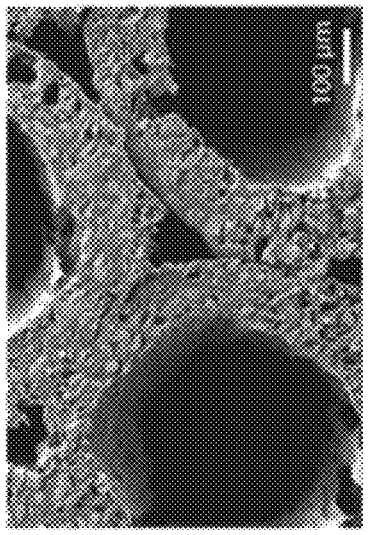
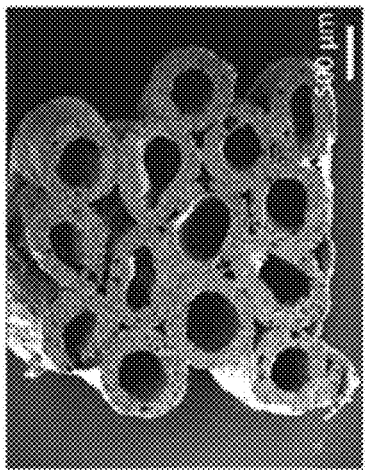
FIG. 5E  FIG. 5F  FIG. 5G

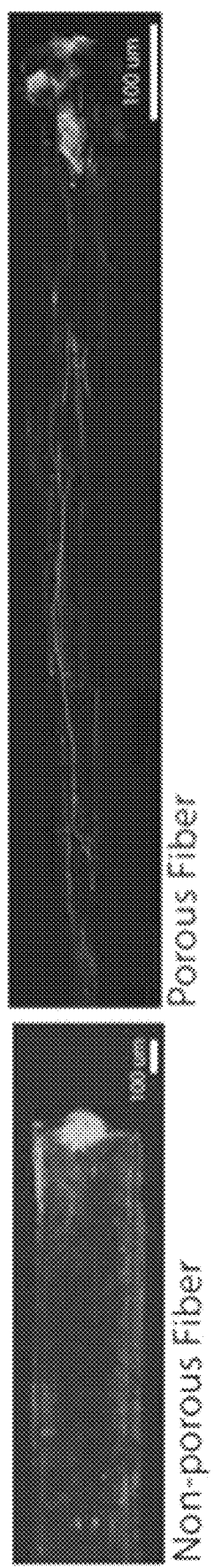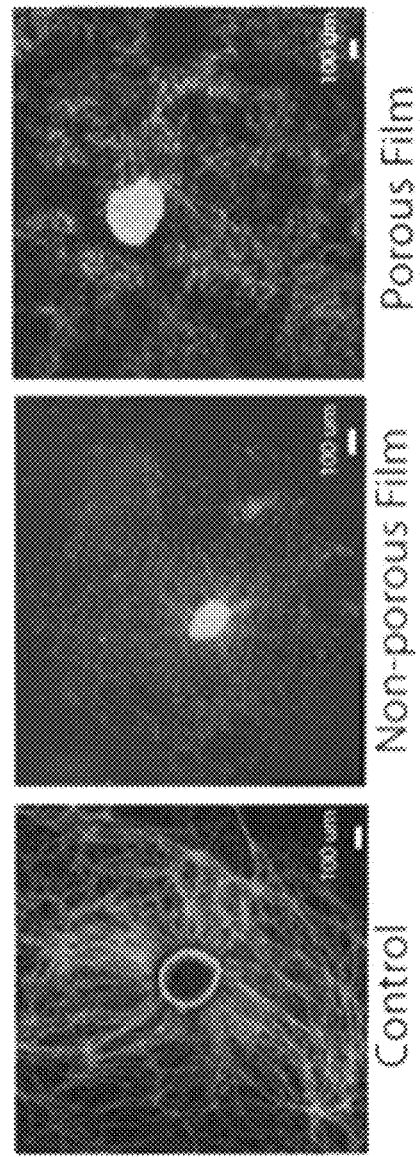
FIG. 6A  FIG. 6B  FIG. 6C  FIG. 6D  FIG. 6E

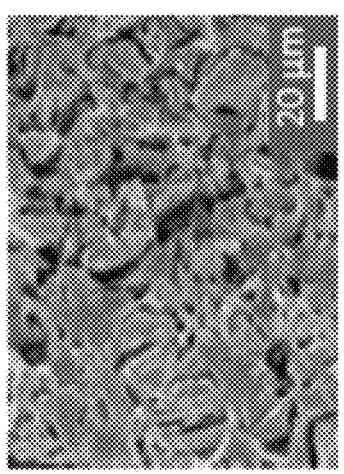
FIG. 7A
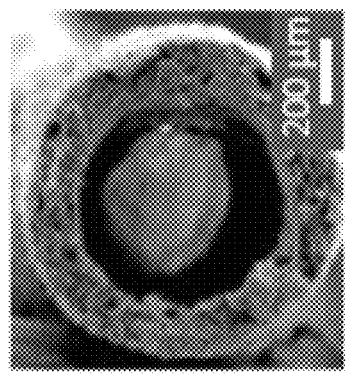
FIG. 7B
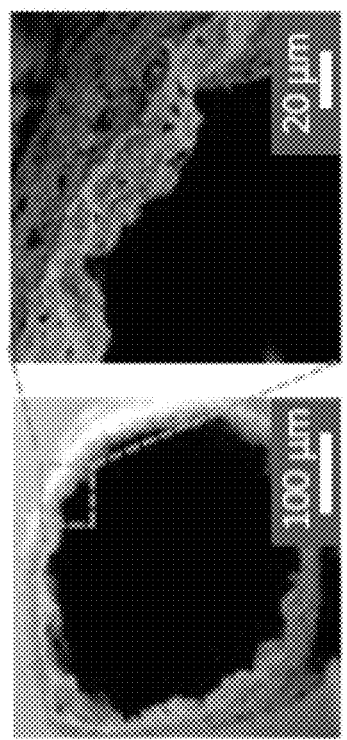
FIG. 7C
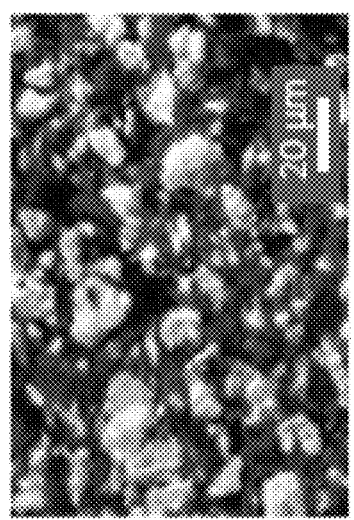
FIG. 7D
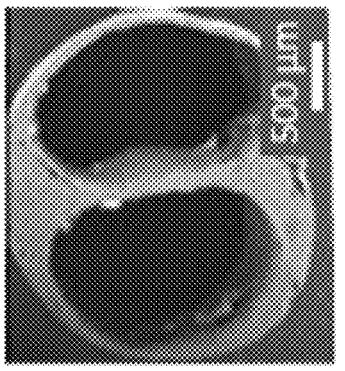
FIG. 7E
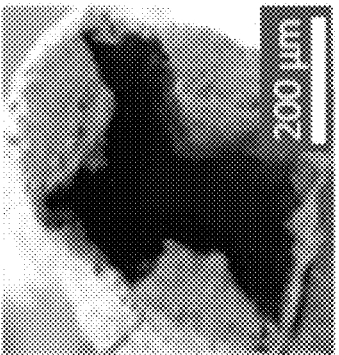
FIG. 7F
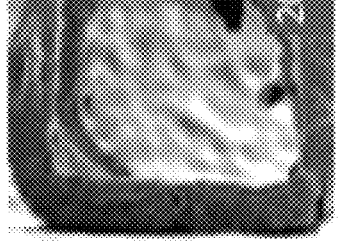
FIG. 7G
FIG. 7H

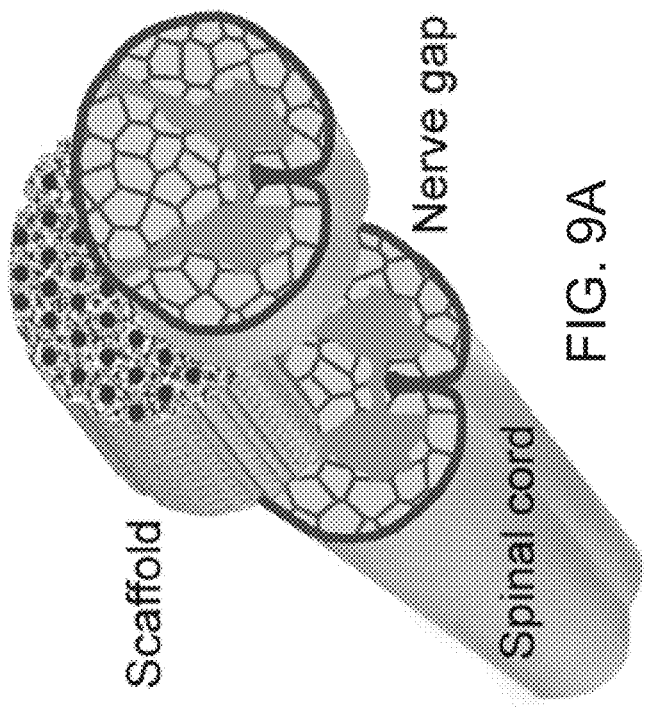
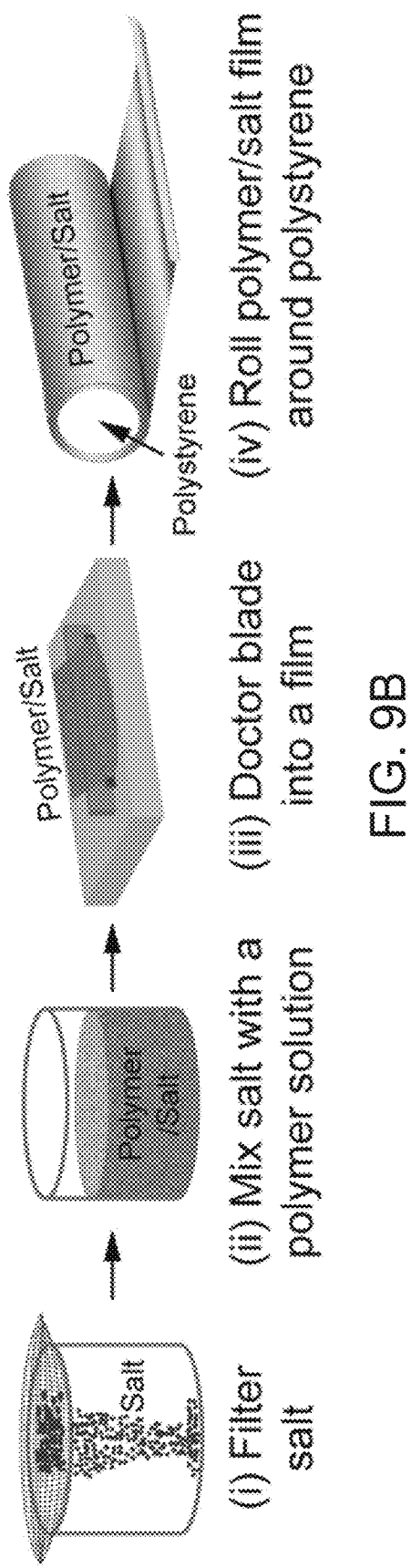
FIG. 9A
FIG. 9B

FIG. 9J
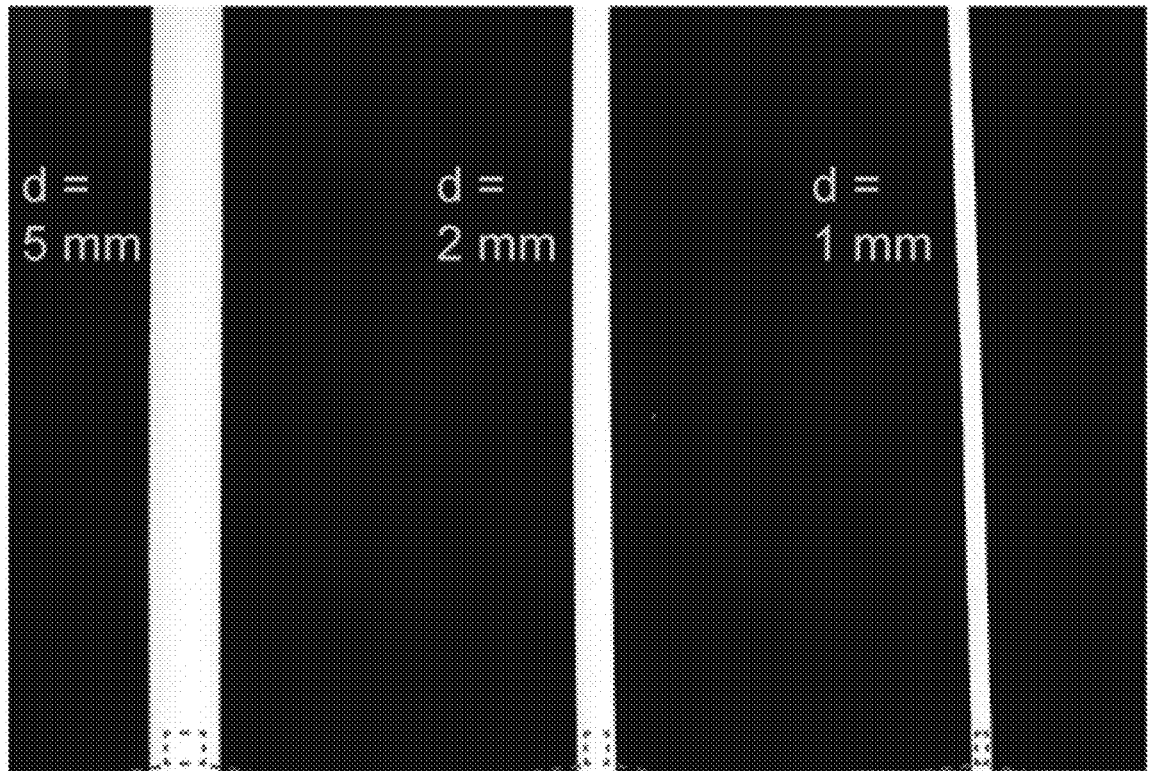
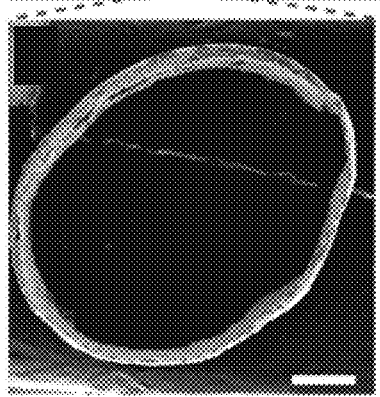
FIG. 9K
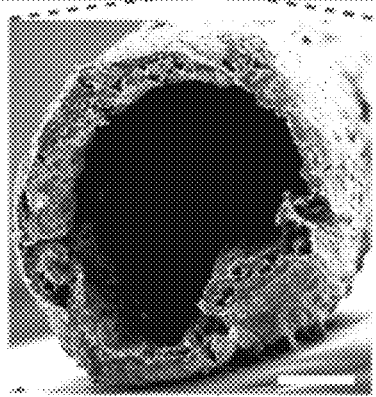
FIG. 9L
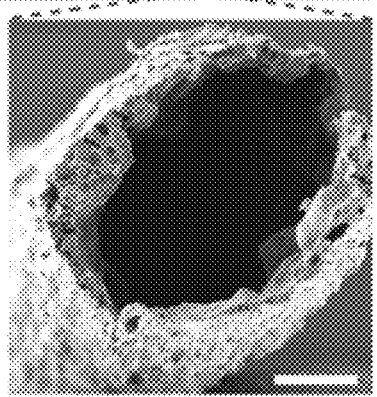
FIG. 9M
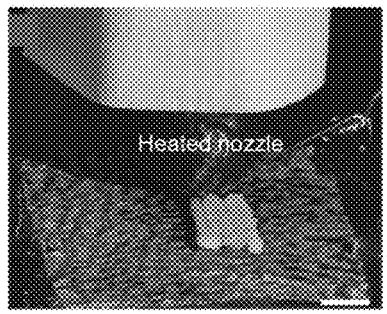
FIG. 9N
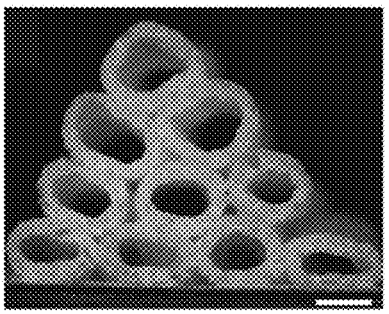
FIG. 9O
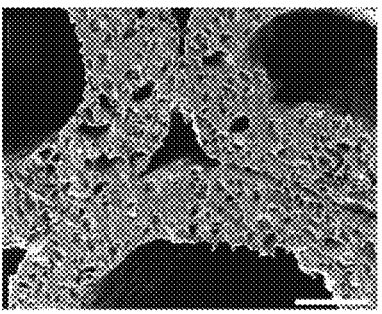
FIG. 9P ■ C  ■ Na  ■ Cl

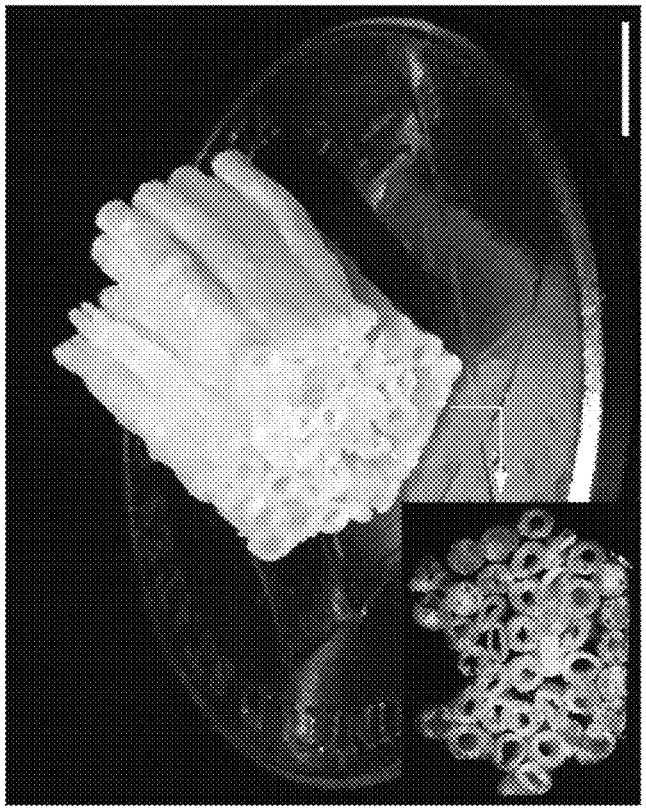
FIG. 11A
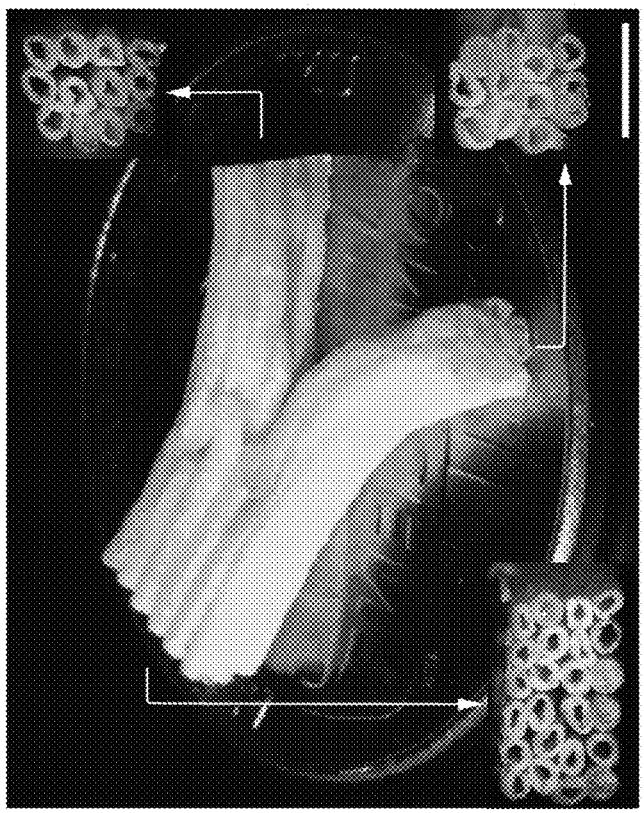
FIG. 11B
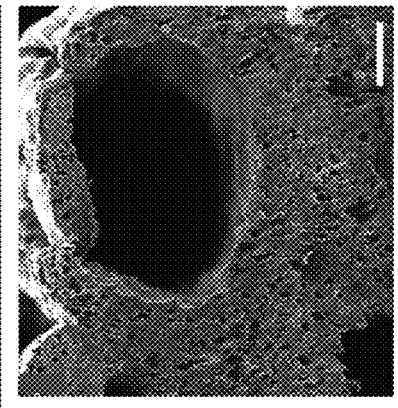
FIG. 11F
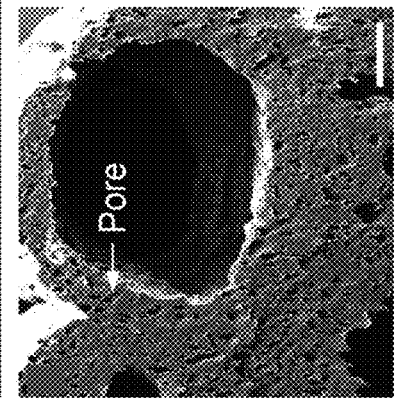
FIG. 11E
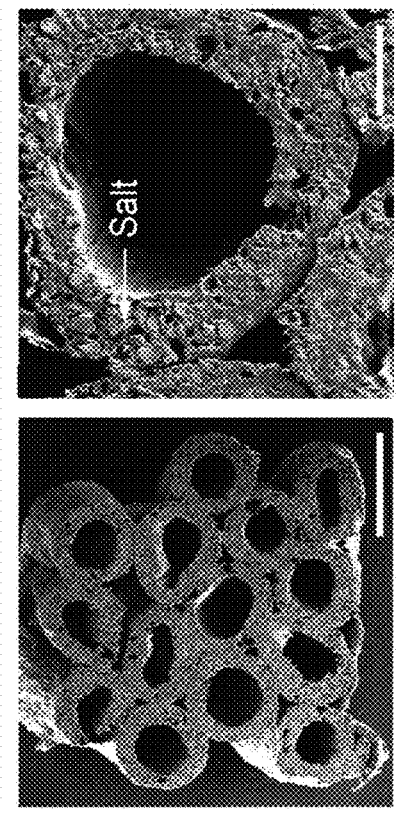
FIG. 11D / FIG. 11C

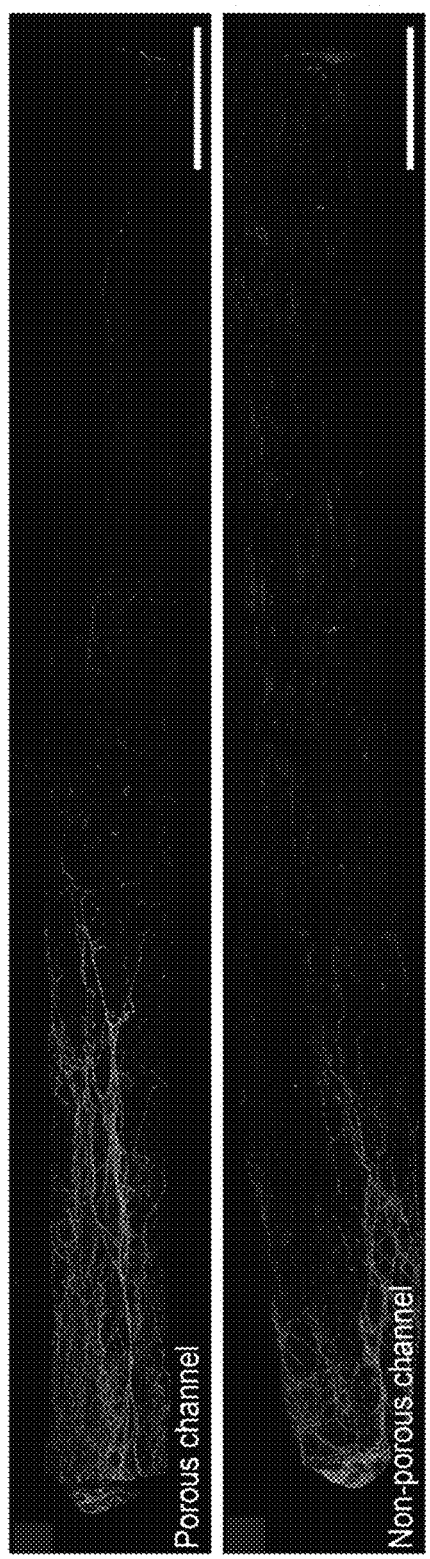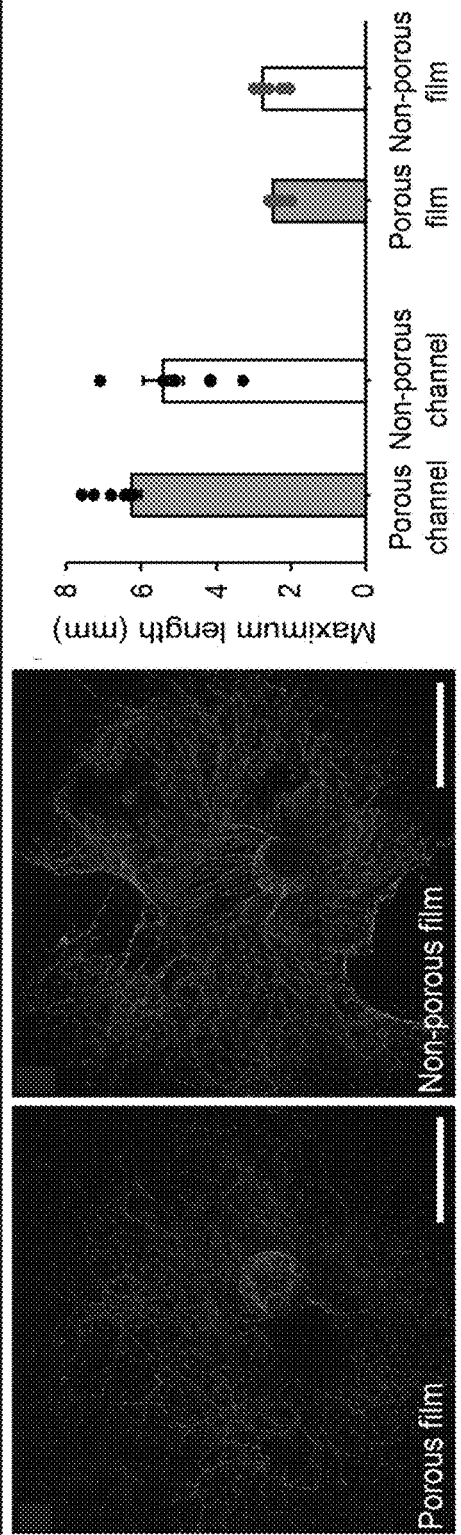
FIG. 12A FIG. 12B FIG. 12C FIG. 12D FIG. 12E

FIG. 16A
FIG. 16B
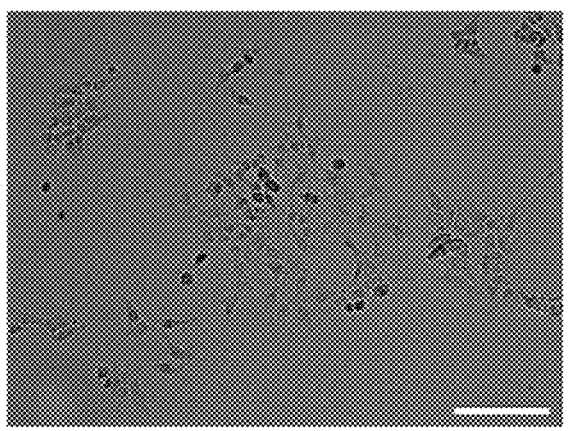
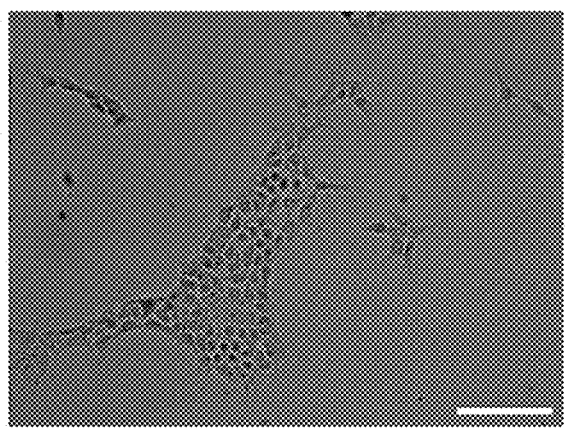
FIG. 16C
FIG. 16D
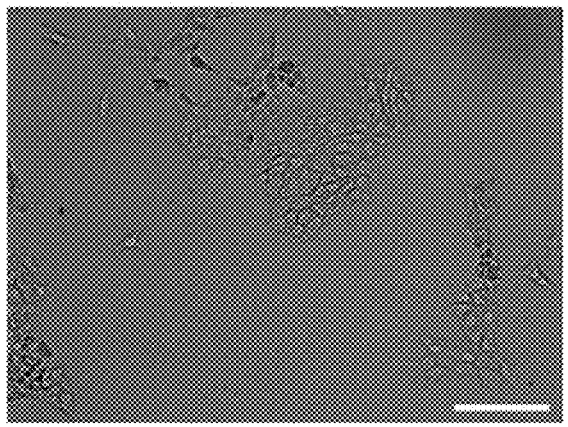
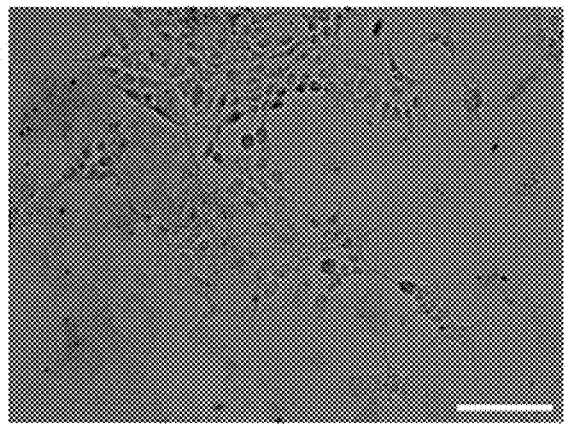
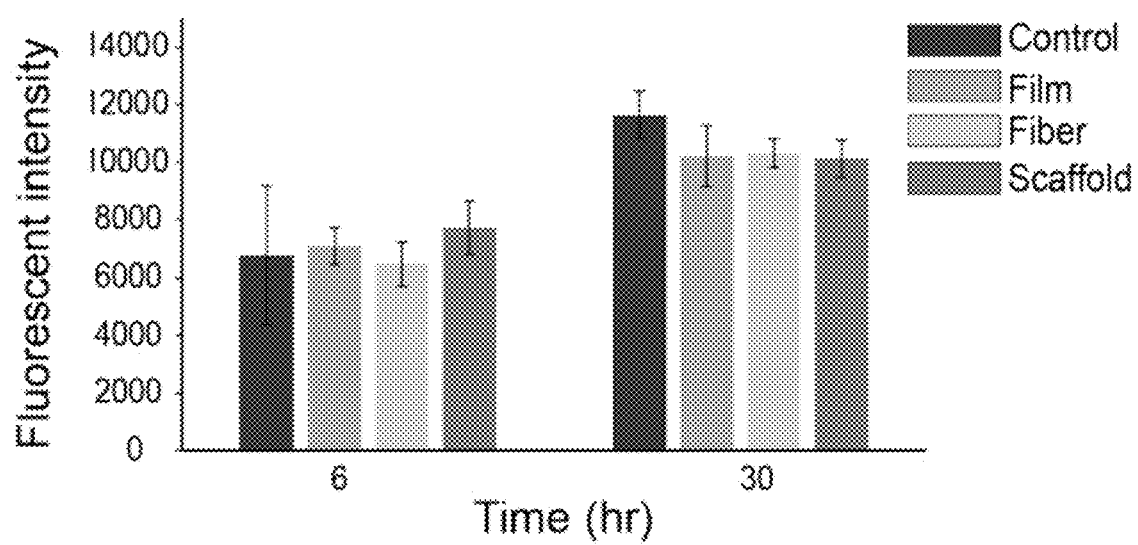
FIG. 16E

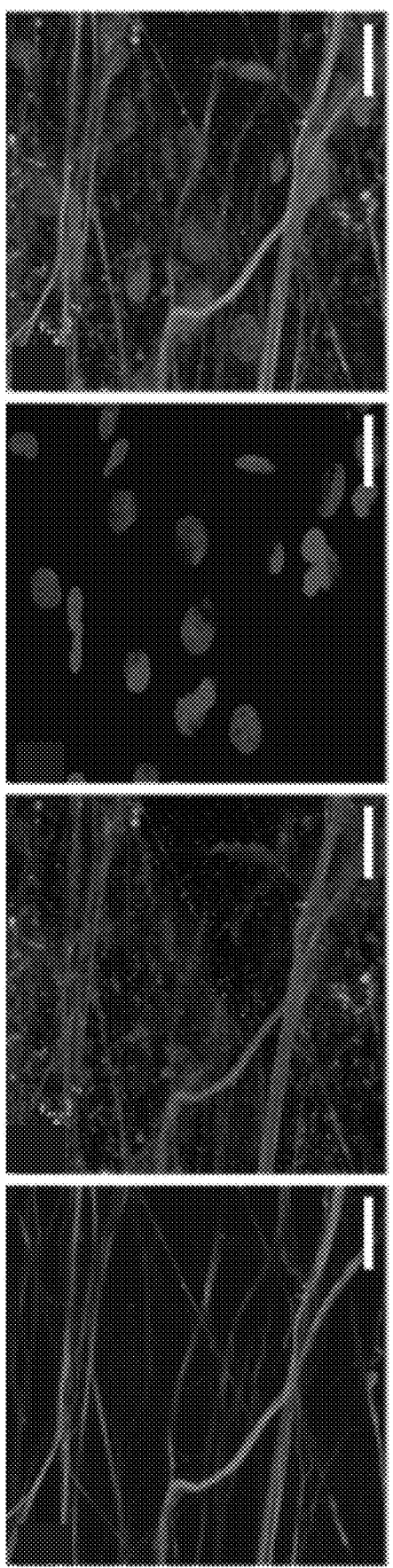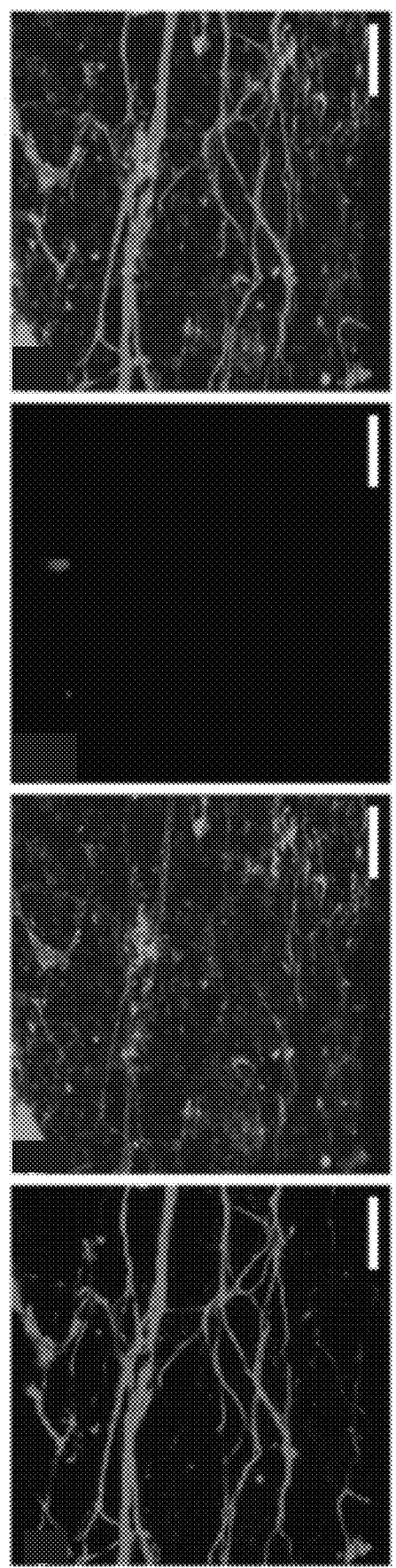

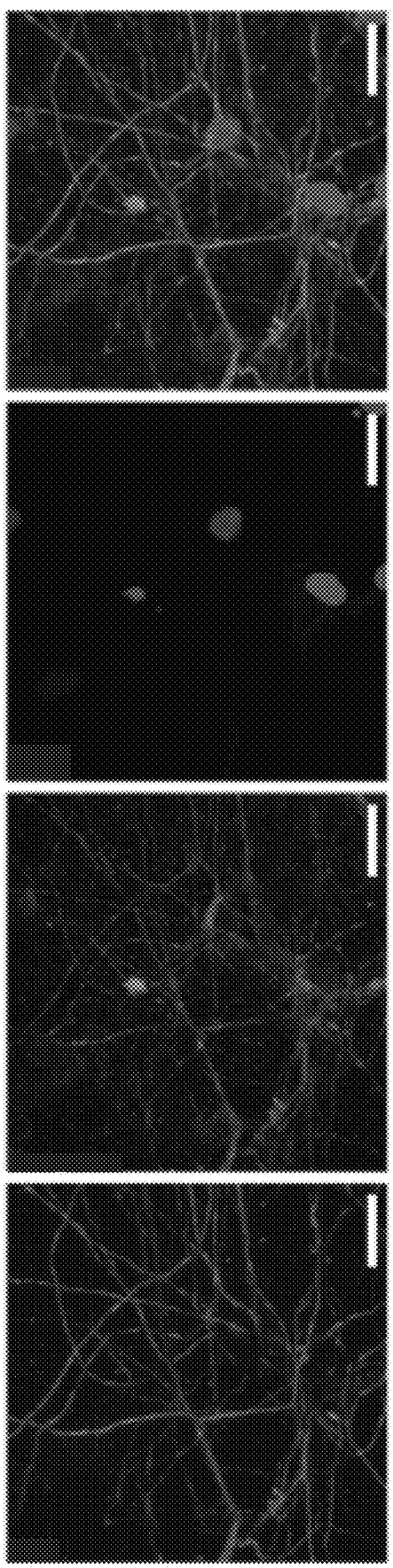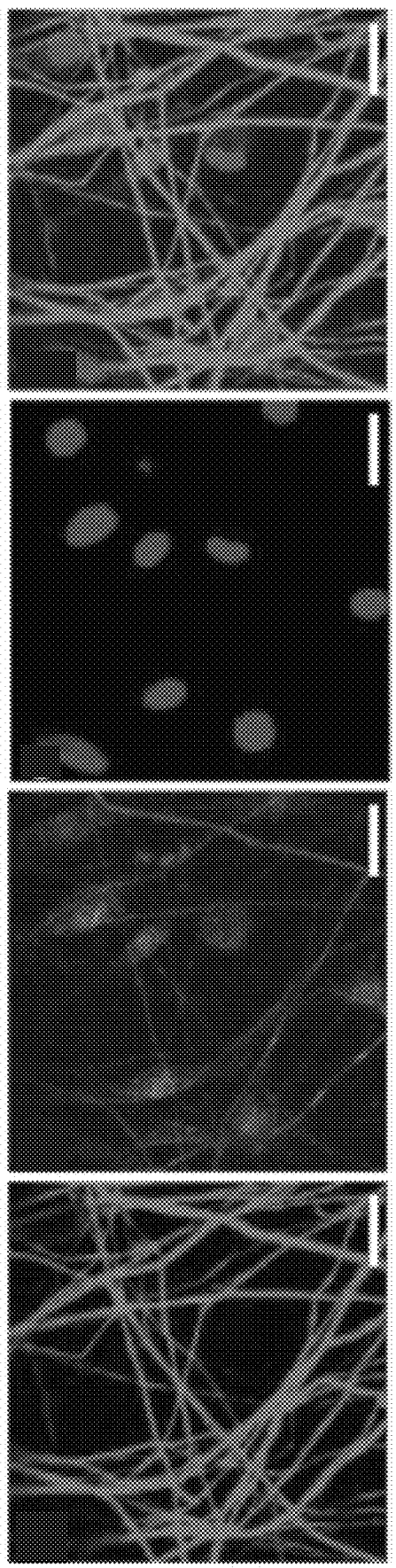

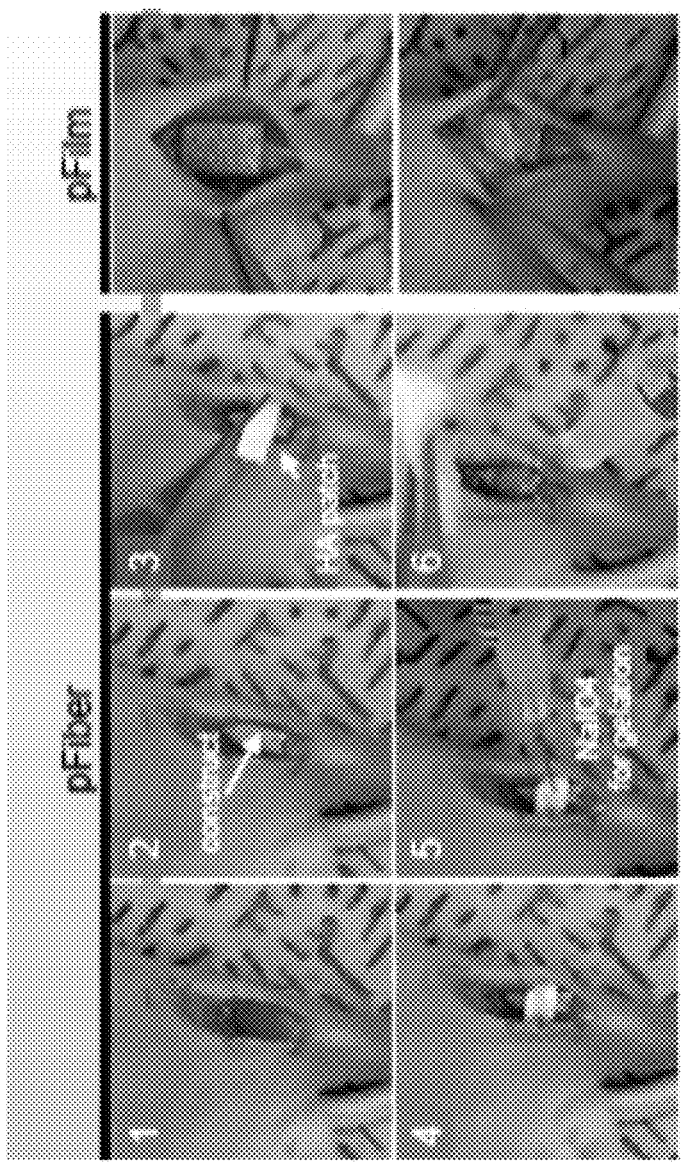
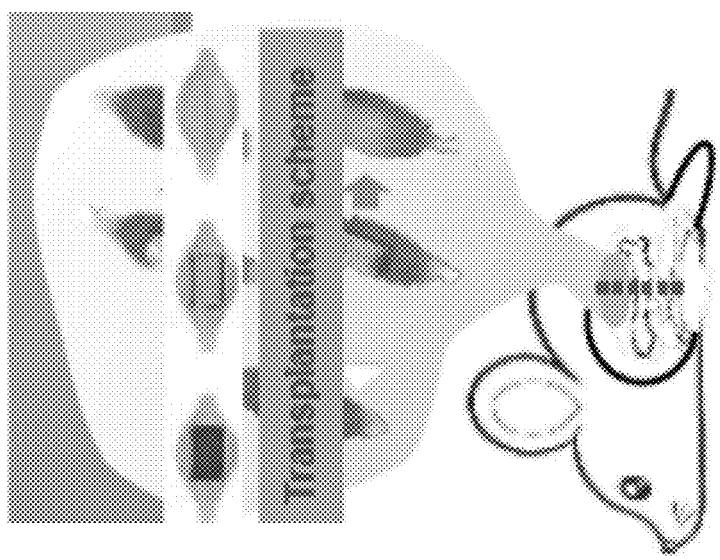
FIG. 19B
FIG. 19A

STRUCTURES WITH COMPLEX GEOMETRIES AND CONTROLLED POROSITY IN MICROMETER TO METER DIMENSIONS PRODUCED AT LARGE SCALE

CROSS-REFERENCE TO RELATED APPLICATION

This application claims priority to U.S. Provisional Application No. 62/772,968 filed Nov. 29, 2018, titled "STRUCTURES WITH COMPLEX GEOMETRIES AND CONTROLLED POROSITY IN MICROMETER TO METER DIMENSIONS PRODUCED AT LARGE SCALE", the entire disclosure of which is incorporated herein by reference.

STATEMENT OF GOVERNMENT SUPPORT

This invention was made with Government support under Grant No. R01 NS086804 awarded by the National Institutes of Health, and Grant No. DMR1419807 awarded by the National Science Foundation. The Government has certain rights in the invention.

BACKGROUND

Porous scaffolds with precise microstructures and geometries are ubiquitous in biological applications, such as tissue regeneration and cell and bacteria confinement, as well as non-biological fields, such as gas separation and water filtration. In particular, nerve guidance scaffolds (NGS) have gained utility in the field of nerve regeneration. There are several FDA-approved conduits used in the clinical setting for peripheral nerve repair. The implants are hypothesized to guide the growing axons to recapitulate with their pre-existing targets. However, the current commercially available fabrication techniques do not result in flexible conduits in few cm-scale, a length scale that corresponds to common human peripheral nerve injuries. NeuroFlex is currently one of the most flexible FDA-approved implants with a maximum of 60° of flexibility but is only up to 2.5 cm in length. Conduits as long as 6 cm are marketed but have limited flexibility and can result in pain after implantation. Another major drawback of the clinically available synthetic implants is that they are single-channel conduits. Single-channel conduits cannot maintain the organization of the neurons and guiding axons over cm-long scales. In addition, the abnormal synaptic formation of neurons to incorrect targets is inefficient for nerve repair and can result in neuropathy. As such, the clinical efficacy of NGS is less than 30%. One intervention to circumvent this problem is to develop scaffolds that confine axon growth within microchannels. Other work describes conduits produced at cm scale that can then be manually stacked in a larger conduit to produce multichannel scaffolds, but this process is manual with low precision and reproducibility. In addition the material selection for the scaffold is limited.

Several studies have developed microchannel scaffolds from different materials and have confirmed their efficacy in rodents in both the transected spinal cord and sciatic nerve. The common techniques include molding, extrusion, freeze drying, 3D printing, lithography and electrospinning. There are still several challenges that need to be addressed to transition microchannel scaffolds to the clinical setting. First, a scaffold fabrication technique with flexibility over material selection is required to optimize the scaffolds mechanical and chemical properties for enhanced biocompatibility and nerve growth. Also, it is essential to develop and control interconnected porosity to enable the transport of nutrients, oxygen and waste. Moreover, hollow microchannels with various outer geometries and bifurcation are also necessary to match the nerve structure. The ability to produce scaffolds with different lengths and cross-sectional sizes at high-throughput can enhance the seamless applicability of the scaffolds to the clinical setting.

SUMMARY

A method of manufacturing a porous fiber includes combining salt particles with a thermoplastic to generate a preform having the salt particles embedded therein. The method also includes drawing a fiber from the preform at a temperature above a glass transition temperature of the thermoplastic, and removing the salt particles from the fiber to generate the porous fiber.

A method of manufacturing a porous tissue scaffold with a target pore size and a target porosity includes combining salt particles of the same diameter or smaller than the target pore diameter with a solution including a thermoplastic dissolved in a solvent to generate a salt-thermoplastic solution. A ratio of the salt particles to the thermoplastic in the salt-thermoplastic solution can be selected based on the target porosity. The method further includes blading the salt-thermoplastic solution into a film having a predetermined thickness, and rolling the film onto a core substrate to create a preform. The method further includes inserting the preform into a cladding to create a cladded preform, and drawing a fiber from the cladded preform. The method further includes etching the fiber to remove the cladding and the core substrate, and depositing the fiber as a set of stacked filaments in a predetermined arrangement. The method also includes trimming the ends of one or more filaments of the set of filaments to expose an inner core of that filament, and leaching the salt particles from the set of filaments to generate the porous tissue scaffold.

All combinations of the foregoing concepts and additional concepts discussed in greater detail below (provided such concepts are not mutually inconsistent) are part of the inventive subject matter disclosed herein. In particular, all combinations of claimed subject matter appearing at the end of this disclosure are part of the inventive subject matter disclosed herein. The terminology used herein that also may appear in any disclosure incorporated by reference should be accorded a meaning most consistent with the particular concepts disclosed herein.

BRIEF DESCRIPTIONS OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIG. 1A is an image of an agarose scaffold in a polycaprolactone (PCL) conduit.

FIG. 1B is an image of a scaffold sutured to a transected rat sciatic nerve.

FIG. 1C is a magnified view of a rostral end of the scaffold of FIG. 1B.

FIG. 1D is a magnified view of a distal end of the scaffold of FIG. 1B.

Figure 3A:
FIG. 3A illustrates fabrication steps for generating a rolled film from a polymer-salt particle solution.
Figure 3A:
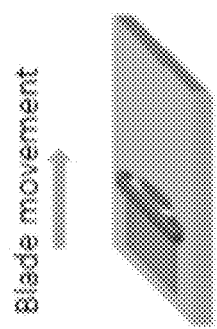
Figure 3A:
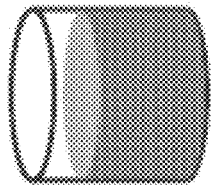
Figure 3A:
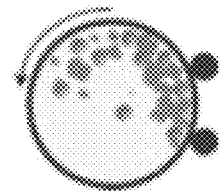
Figure 3B:
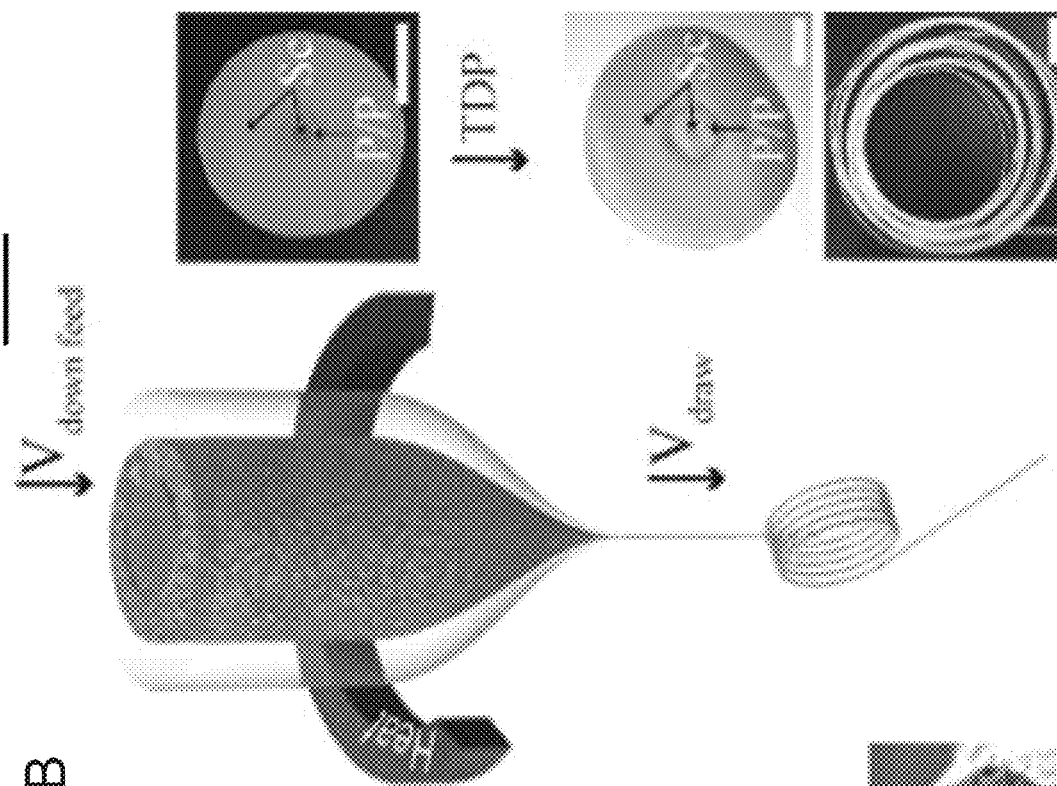

FIG. 3B illustrates insertion of the rolled inform into another sacrificial layer to generate a preform, which is then thermally drawn. Also illustrated are thermally drawn polycaprolactone (PCL) fibers, both the preform cross-section (top panel) and its drawn fiber cross-section (middle panel). As seen in the bottom panel, drawing produces meters of the fibers. The scale bars are 1 cm (top panel), 0.3 mm (middle panel), and 1 cm (bottom panel).

Figure 3C:
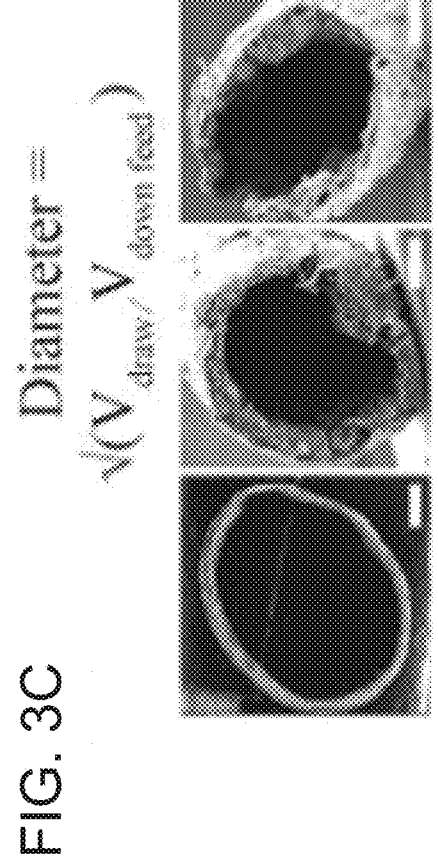

FIG. 3C illustrates drawn fibers of three different diameters upon the removal of the outer sacrificial layer/material. The diameter of the drawn material can be controlled by the preform feeding rate and/or drawing speed. The scale bars are 500 µm (left panel), 200 µm (middle panel), and 100 µm (right panel).

Figure 3E:
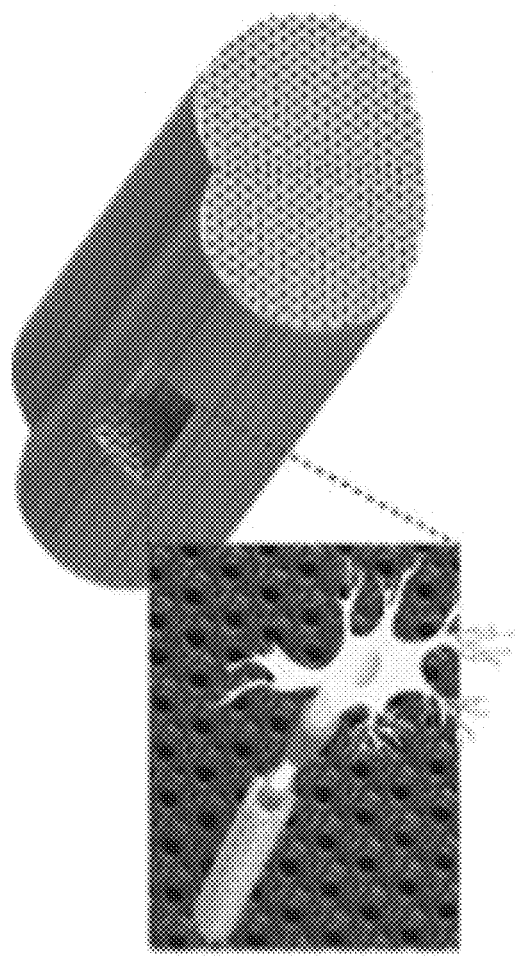
Figure 3D:
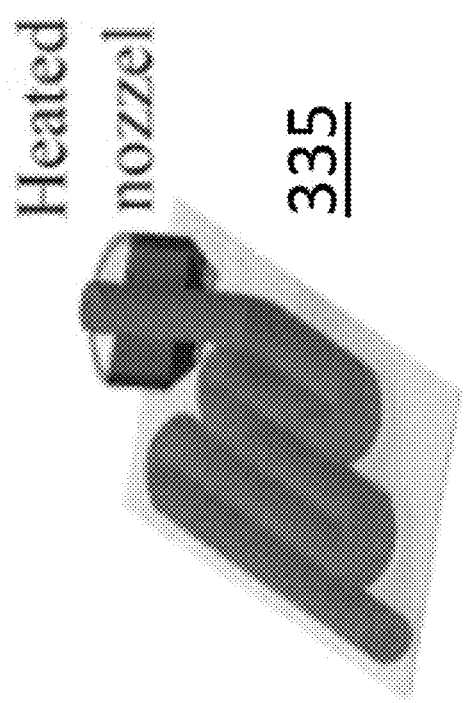

FIG. 3D illustrates passage of the fiber through a heated nozzle to 3D print scaffolds with complex geometries.

FIG. 3E illustrates how a printed scaffold can match the outer structure of a spinal cord and linearly guide growing neurons within its microchannels.

Figure 4A:
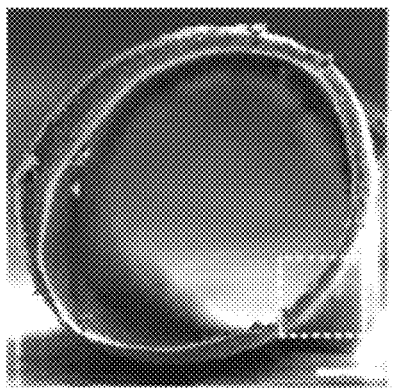

FIG. 4A illustrates a non-porous PCL conduit. The scale bar is 100 µm.

Figure 4B:
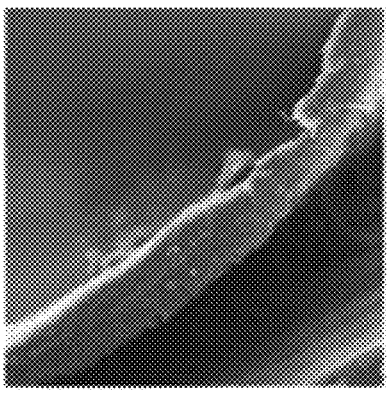

FIG. 4B illustrates a magnified image of a portion of FIG. 4A. The scale bar is 40 µm.

Figure 4C:
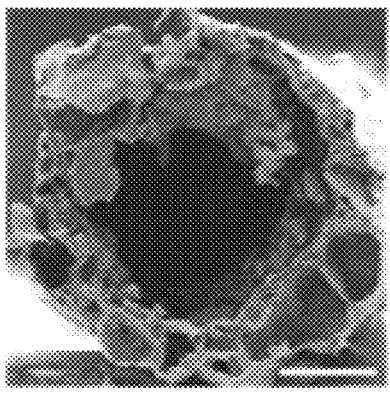

FIG. 4C illustrates a porous PCT conduit with a range of salt particle sizes. The scale bar is 100 µm.

Figure 4D:
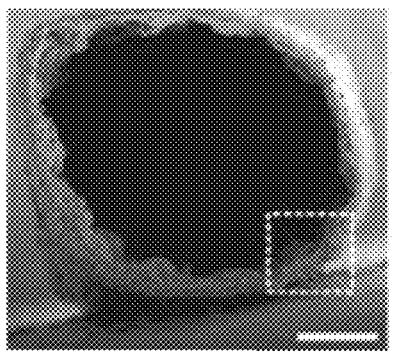

FIG. 4D illustrates a porous PCT conduit with salt particles filtered to less than 28 µm diameter, and having a circular cross-section. The scale bar is 100 µm.

Figure 4E:
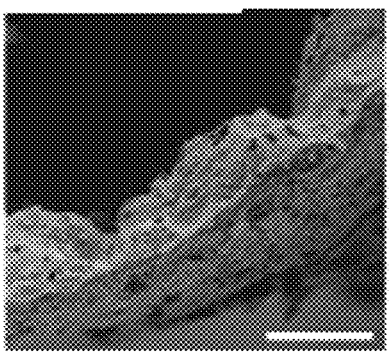

FIG. 4E illustrates a magnified image of a portion of FIG. 4D. The scale bar is 40 µm.

Figure 4F:
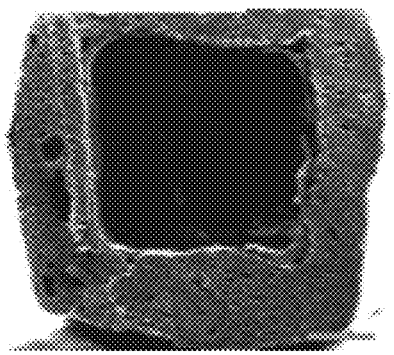

FIG. 4F illustrates a porous PCT conduit with salt particles filtered to less than 28 µm diameter, and having a square cross-section. The scale bar is 200 µm.

Figure 4G:
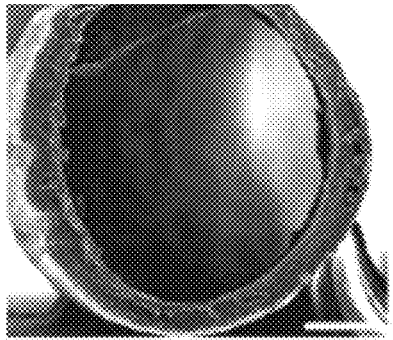

FIG. 4G illustrates a non-porous PLA conduit. The scale bar is 100 µm.

Figure 4H:
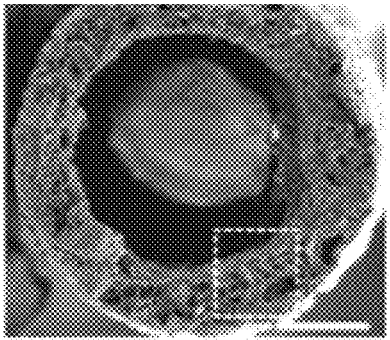

FIG. 4H illustrates a porous PLA conduit. The scale bar is 100 µm.

Figure 4I:
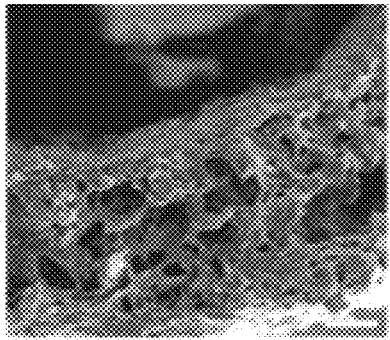

FIG. 4I illustrates a magnified image of a portion of FIG. 4H. The scale bar is 40 µm.

Figure 4K:
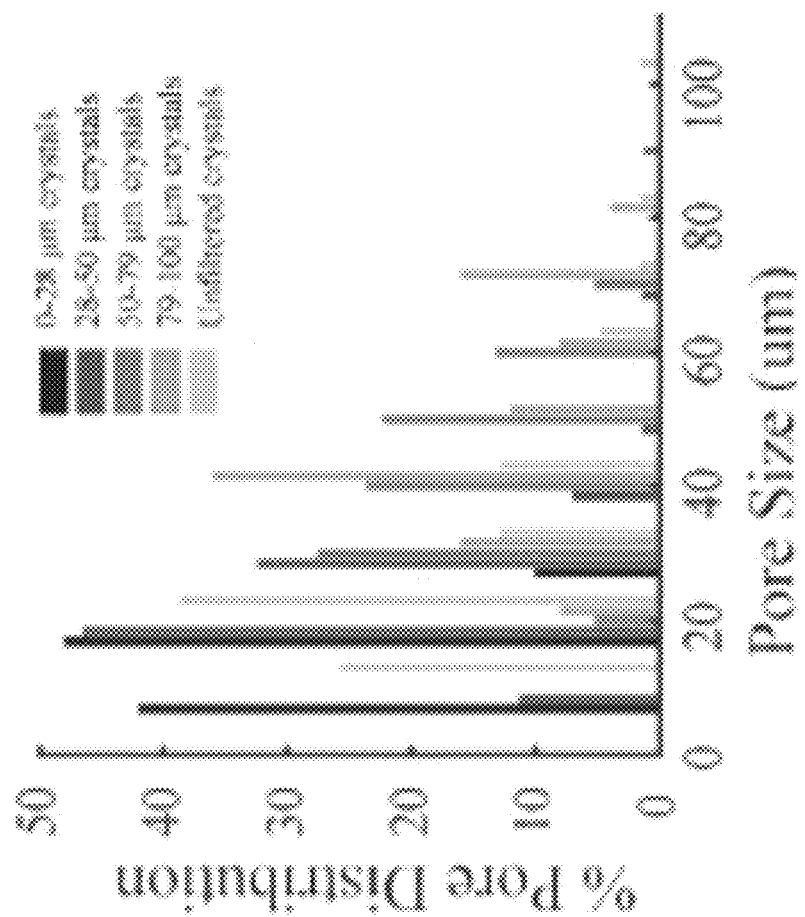
Figure 4J:
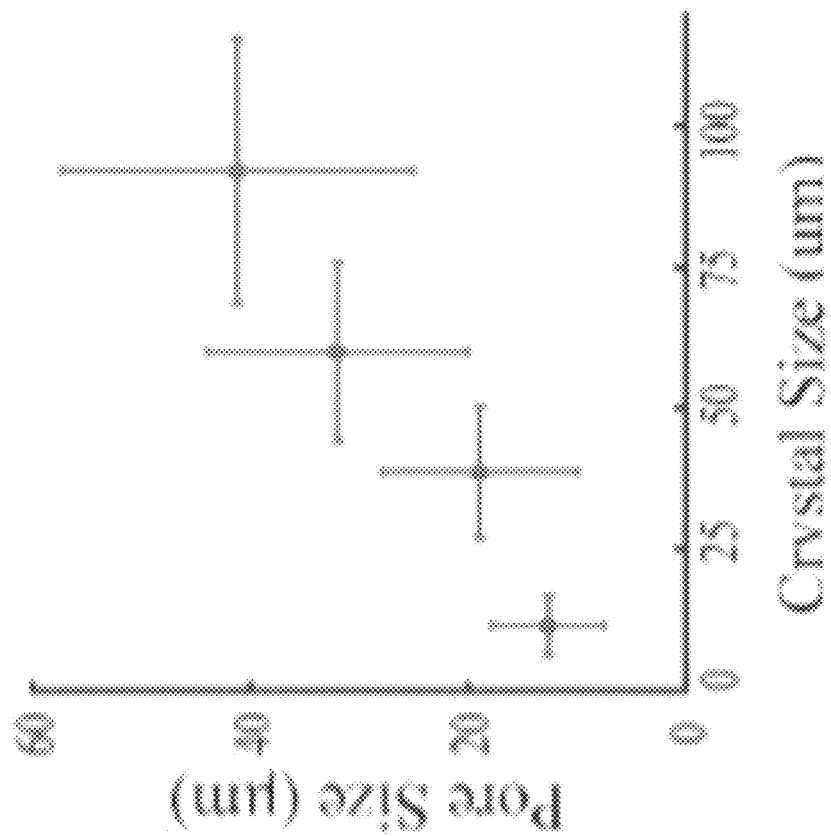

FIG. 4J is a plot illustrating that the average size of the salt particles used for fiber fabrication correlate to the average pore sizes in the fiber. Bars indicate standard deviation.

FIG. 4K is a histogram of pore distribution in conduits fabricated with different range of salt particles.

FIG. 4L illustrates EDX analysis on a PCL fiber prior to salt leaching The scale bar is 30 µm.

FIG. 4M illustrates EDX analysis on the PCL fiber of FIG. 4L one hour after salt-leaching. The scale bar is 30 µm.

FIG. 4N illustrates EDX analysis on the PCL fiber of FIG. 4L 24 hours after salt-leaching. The scale bar is 30 µm.

FIG. 5A shows the microchannel structures of a printed bifurcated scaffold.

FIG. 5B also shows the microchannel structures of a printed bifurcated scaffold.

FIG. 5C shows a bifurcated scaffold and the inset panels shows the end of the scaffold demonstrating its microchannel structure.

FIG. 5D shows a butterfly-shaped scaffold and the inset panels shows the end of the scaffold demonstrating its microchannel structure.

FIG. 5E shows a hexagonally packed scaffold

FIG. 5F shows a magnified view of FIG. 5E, before salt removal.

FIG. 5G shows a magnified view of FIG. 5E after salt-removal.

Figure 5H:
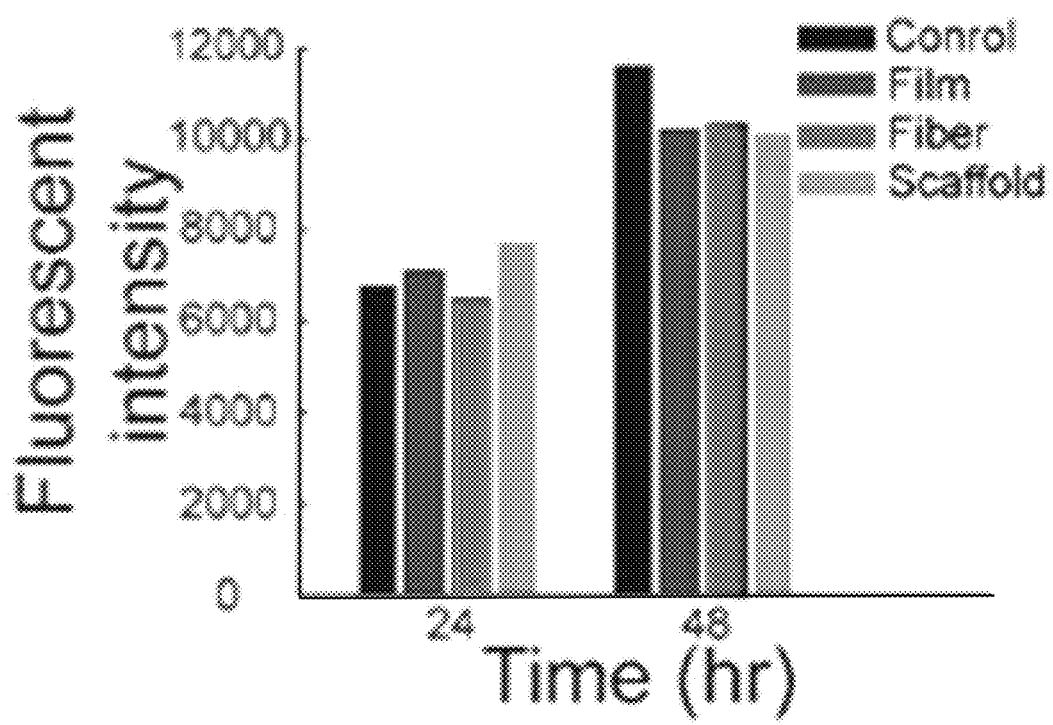

FIG. 5H is a plot of cytotoxicity using AlamarBlue® assay of HEK293 cells with or without fiber, film or scaffold in the medium and indicates the safety of the material in vitro.

Figure 5J:
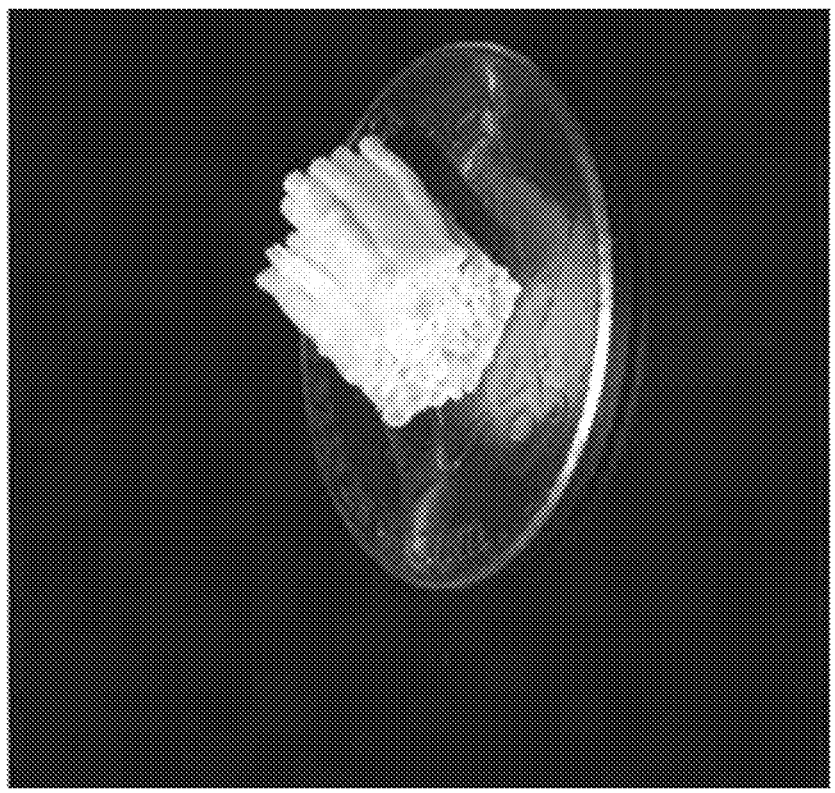
Figure 5I:
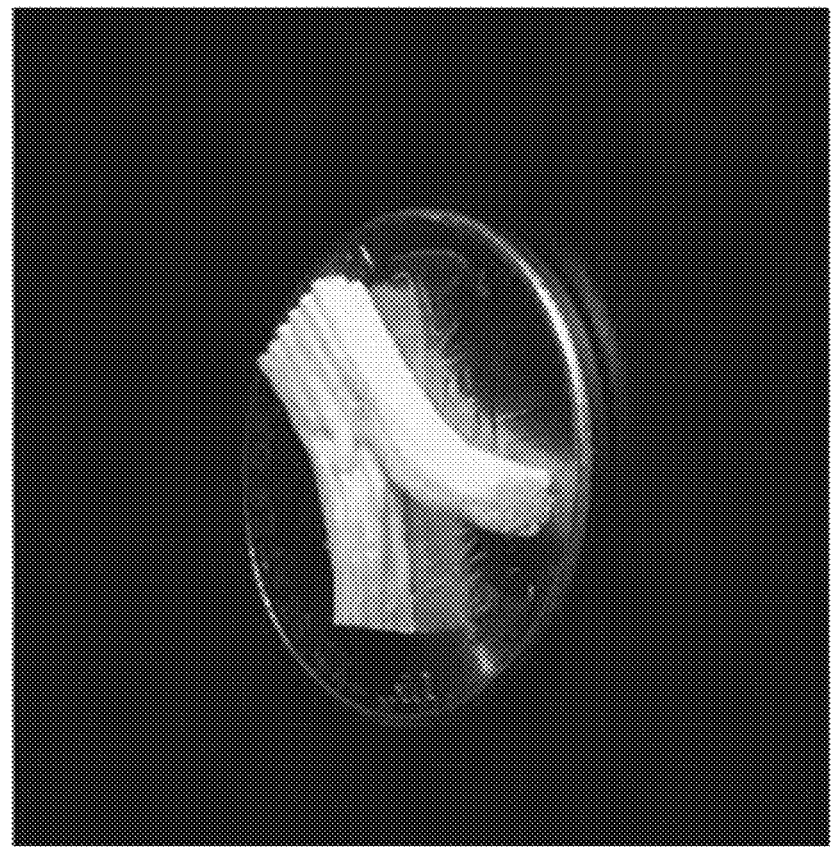

FIG. 5I shows a cm-scale scaffold in a triangle, hexagonal packing.

FIG. 5J shows a cm-scale scaffold having a butterfly structure which resembles the spinal cord cross-section.

FIG. 6A shows neurofilament (NF) growth of a dorsal root ganglion cell (DRG) in a fibronectin-coated, non-porous fiber after 12 days.

FIG. 6B shows neurofilament (NF) growth of a dorsal root ganglion cell (DRG) in a fibronectin-coated, porous fiber after 12 days.

FIG. 6C shows neurofilament (NF) growth of a dorsal root ganglion cell (DRG) on a fibronectin-coated, cover glass as control after 12 days.

FIG. 6D shows neurofilament (NF) growth of a dorsal root ganglion cell (DRG) on a fibronectin-coated non-porous film after 12 days.

FIG. 6E shows neurofilament (NF) growth of a dorsal root ganglion cell (DRG) on a fibronectin-coated porous film after 12 days.

FIG. 7A shows a porous circular fiber.

FIG. 7B shows a magnified view of a portion of the fiber of FIG. 7A.

FIG. 7C shows a porous fiber with a circular cross-section.

FIG. 7D shows a porous fiber with square cross-section.

FIG. 7E shows a porous fiber with inner patterns/groves.

FIG. 7F shows a double channel porous fiber.

FIG. 7G is an SEM image of a porous fiber prior to salt leaching.

FIG. 7H shows the EDX analysis of the SEM image of FIG. 7G.

Figure 7J:
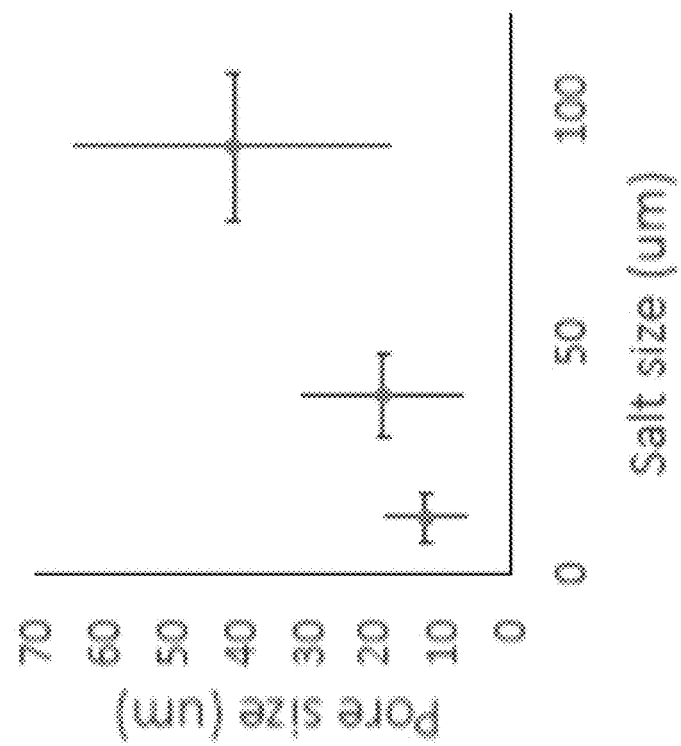
Figure 7I:
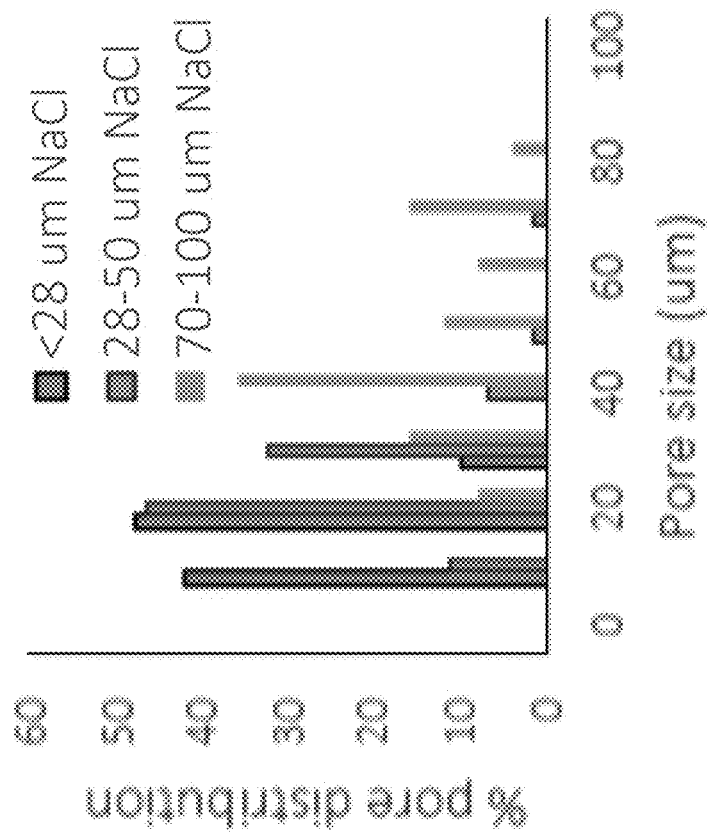

FIG. 7I is a plot illustrating pore distributions in fiber channels produced from PCL composites with NaCl crystals of different size ranges FIG. 7J is a plot illustrating the average sizes of NaCl crystals used for PCL channel fabrication correlated to the average pore sizes. Bars indicate SD.

Figure 8A:
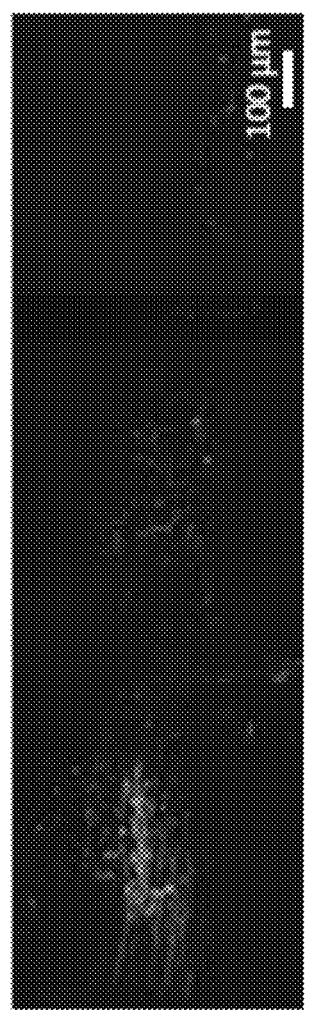

FIG. 8A is an optical image of culturing DRG in a fibronectin-coated porous PCL channel.

Figure 8B:

FIG. 8B illustrates the NF staining of FIG. 8A.

Figure 8C:
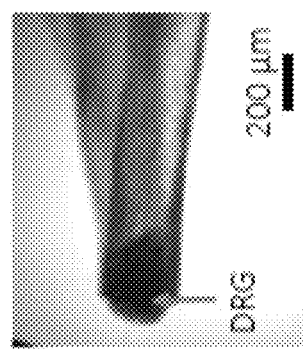

FIG. 8C also illustrates the NF staining of FIG. 8A.

FIG. 9A illustrates a schematic of a spinal cord nerve gap injury and a microchannel scaffold with a matching cross section to bridge the gap.

FIG. 9B illustrates how NaCl crystals are filtered to select grain size and mixed with a polymer solution. The polymer/ salt solution is doctor-bladed into films, then rolled and consolidated around a polystyrene rod used as a sacrificial material.

Figure 9C:
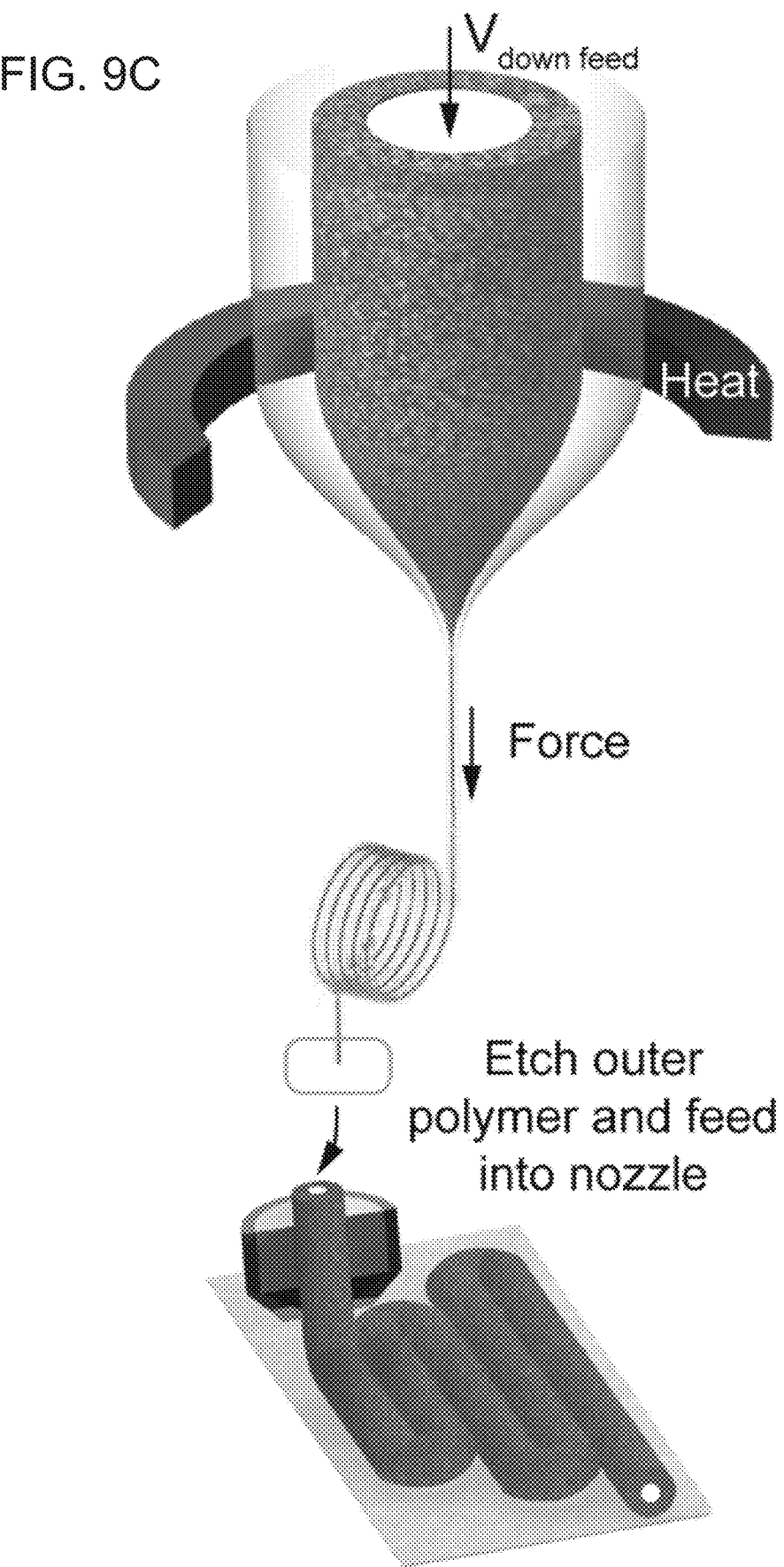
Figure 9D:
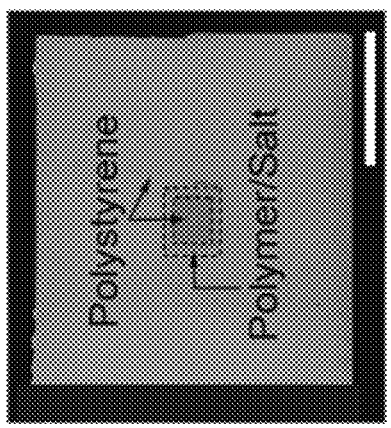

FIG. 9C illustrates how the composite preform is inserted into a sacrificial cladding from the same material as the core, thermally drawn and fed into a heated nozzle for fuse printing FIG. 9D is a cross-sectional photographs of a preform containing PCL/NaCl composite and polystyrene sacrificial core and cladding with circular cross-section.

Figure 9E:
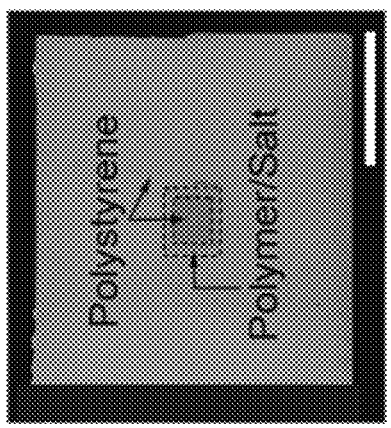

FIG. 9E is a cross-sectional photograph of a preform containing PCL/NaCl composite and polystyrene sacrificial core and cladding with a rectangular cross-section.

Figure 9F:
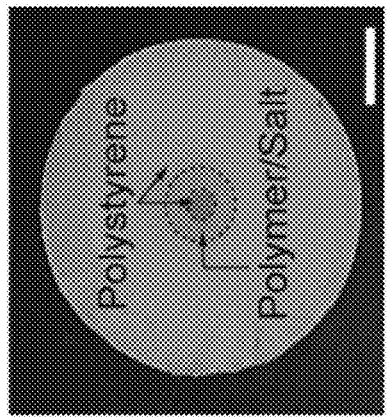

FIG. 9F illustrates a meter-long section of circular fiber produced from the preform in FIG. 9D. Scale bar=10 mm.

Figure 9G:
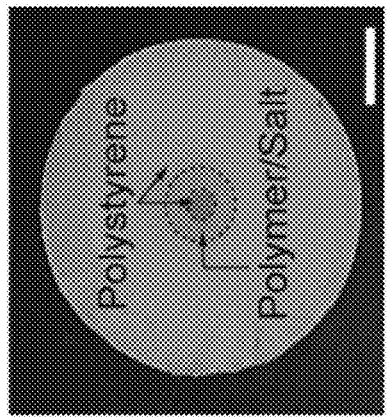

FIG. 9G illustrates a meter-long section of rectangular fiber produced from the preform in FIG. 9E. Scale bar=10 mm.

Figure 9H:
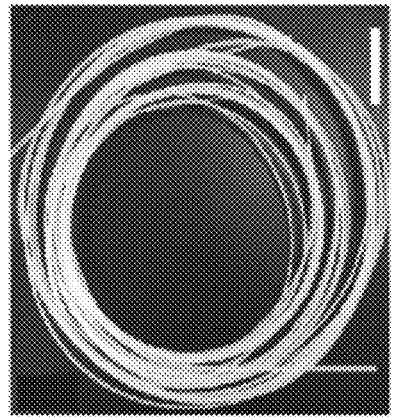

FIG. 9H is a cross-sectional micrograph of the fiber drawn from the preform shown in FIG. 9D. Scale bar=300 µm.

Figure 9I:
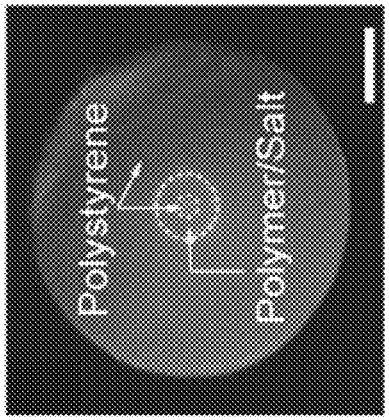

FIG. 9I illustrates a cross-sectional micrograph of the fiber drawn from the preform shown in FIG. 9D. Scale bar=300 µm.

FIG. 9J illustrates hollow channel fibers produced from the preform in FIG. 9D with varying diameters following removal of the sacrificial cladding. The tuning of the channel diameter is achieved by varying the preform feed speed and drawing speed.

FIG. 9K is a first scanning electron microscope (SEM) image of the hollow fibers in FIG. 9J. The scale bar is 500 µm.

FIG. 9L is a second SEM image of the hollow fibers in FIG. 9J. The scale bar is 200 µm.

FIG. 9M is a third SEM image of the hollow fibers in FIG. 9J. The scale bar is 100 µm.

FIG. 9N illustrates how, following removal of the sacrificial core and cladding, the channel fibers are passed through a heated nozzle to fuse print scaffolds with complex geometries. Scale bar=3 mm.

FIG. 9O illustrates a fuse-printed microchannel scaffold with a digitally imparted geometry. Scale bar=300 µm.

FIG. 9P is a close-up SEM image of an interface between three porous channels within a fuse printed scaffold. Scale bar=150 µm.

Figure 10C:
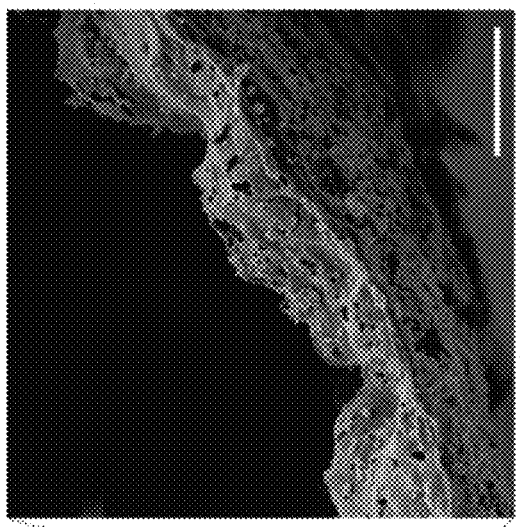
Figure 10B:
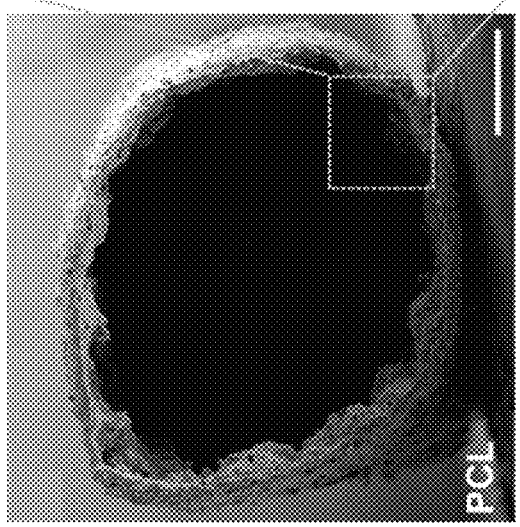
Figure 10A:
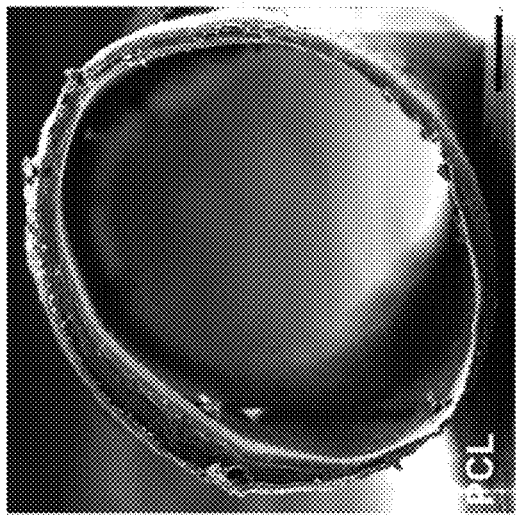

FIG. 10A illustrates a non-porous PCL fiber channel. Scale bar=100 µm.

FIG. 10B illustrates a porous PCL fiber channel. Scale bar=100 µm.

FIG. 10C is a magnified image of the dashed box shown in FIG. 10B. Scale bar=40 µm.

Figure 10F:
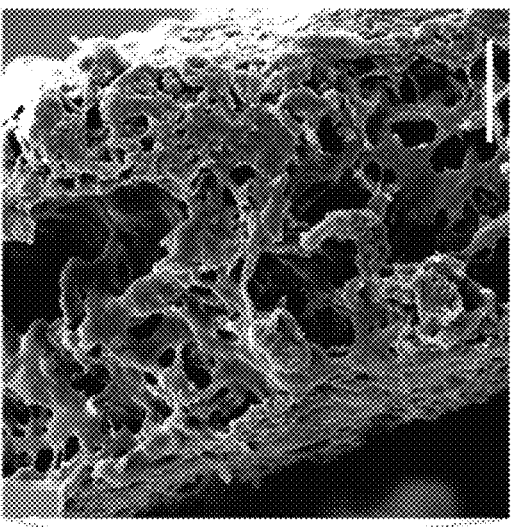
Figure 10E:
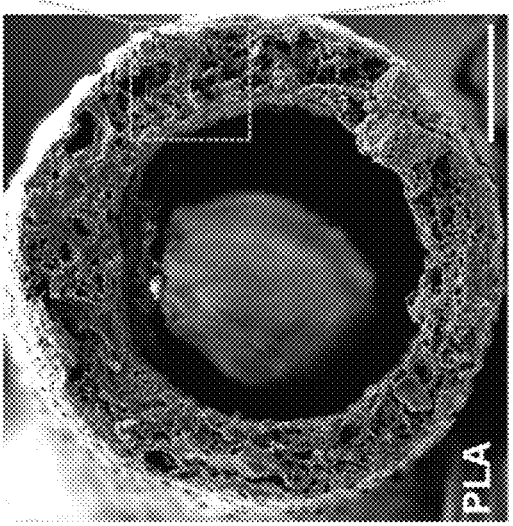
Figure 10D:
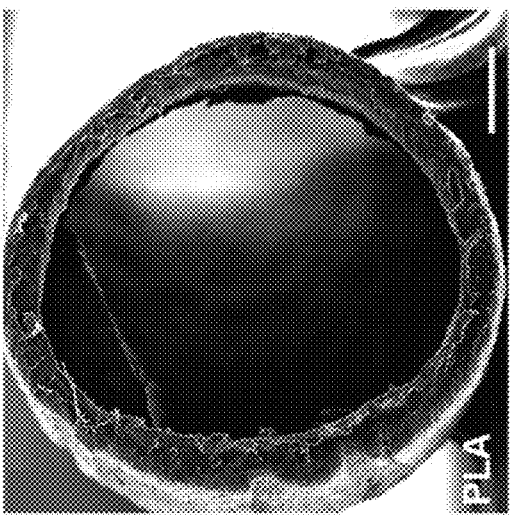

FIG. 10D illustrates a non-porous PLA fiber channel. Scale bar=100 µm.

FIG. 10E illustrates a porous PLA fiber channel. Scale bar=100 µm.

FIG. 10F is a magnified image of the dashed box shown in FIG. 10E. Scale bar=40 µm.

Figures 10G, 10H:
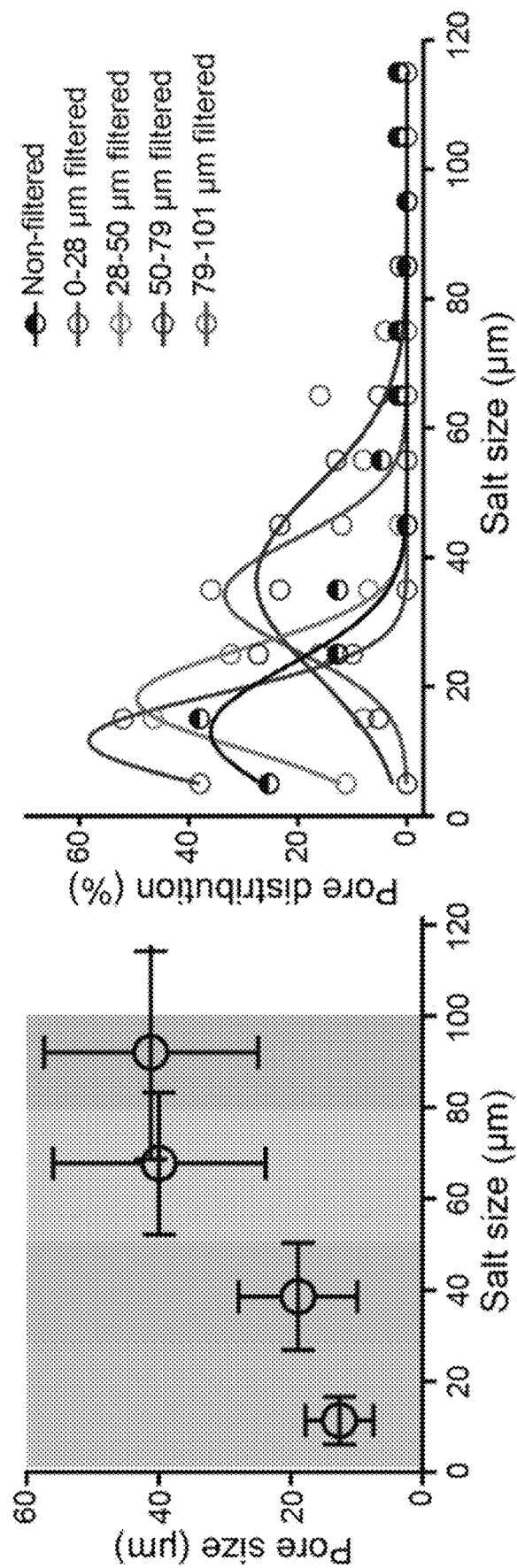

FIG. 10G is a plot illustrating that the average sizes of NaCl crystals used for PCL channel fabrication correlated to the average pore sizes. Bars indicate standard deviation. The shaded areas mark the sizes of the meshes used to filter NaCl crystals.

FIG. 10H is a plot illustrating pore distribution in fiber channels produced from PCL composites with NaCl crystals of different size ranges.

Figure 10K:
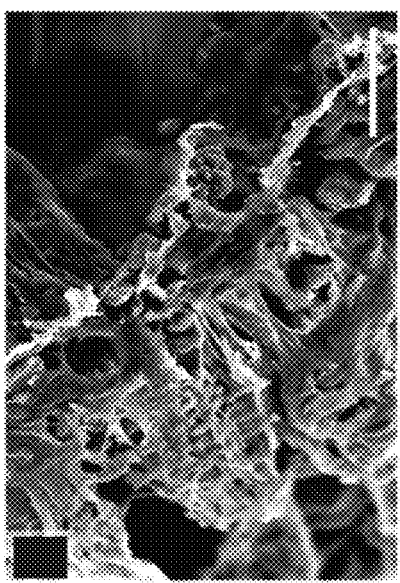
Figure 10N:
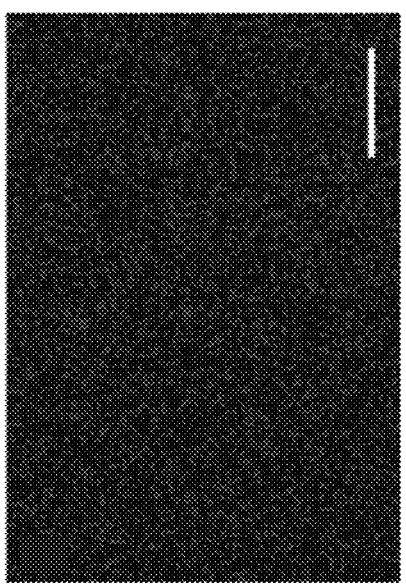
Figure 10J:
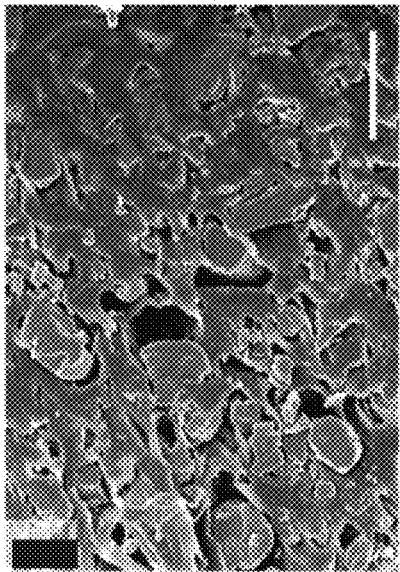
Figure 10M:
Figure 10I:
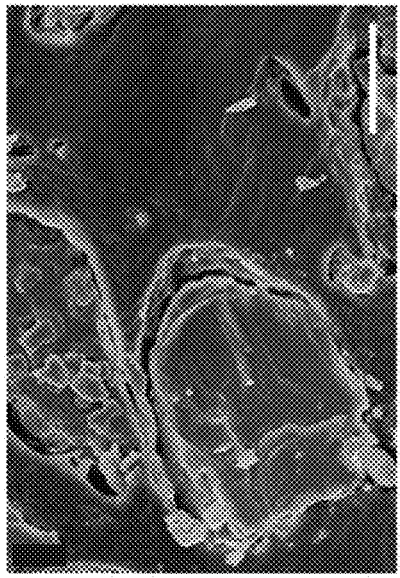

FIG. 10I illustrates a first SEM image of PCL composites, prior to salt-leaching. Scale bar=30 µm.

FIG. 10J illustrates a second SEM image of PCL composites, following one hour of salt-leaching. Scale bar=30 µm.

FIG. 10K illustrates a third SEM image of PCL composites, following 24 hours following salt-leaching. Scale bar=30 µm.

Figure 10L:

FIG. 10L illustrates EDX analysis for the SEM image of FIG. 10I, prior to salt-leaching. Scale bar=30 µm.

FIG. 10M illustrates EDX analysis for the SEM image of FIG. 10J, following one hour of salt-leaching. Scale bar=30 µm.

FIG. 10N illustrates EDX analysis for the SEM image of FIG. 10K, following 24 hours following salt-leaching. Scale bar=30 µm.

FIG. 11A is a photograph of a branched, fuse printed scaffold mimicking a bifurcated nerve. Scale bar=2 mm.

FIG. 11B is a photograph of a butterfly-shaped, fuse printed scaffold mimicking a spinal cord cross-section. Scale bar=2 mm.

FIG. 11C is a SEM image of a hexagonally packed printed scaffold. Scale bar=1 mm.

FIG. 11D illustrates a SEM image prior to salt leaching. Scale bar=200 µm.

FIG. 11E illustrates a SEM image following salt-leaching, demonstrates salt particle removal and emergence of porosity. Scale bar=200 µm.

FIG. 11F is a SEM image of a printed porous scaffold following 4-week incubation in physiological conditions (phosphate buffered saline, 37° C.) under gentle agitation. The structure maintained porosity and adhesion between the individual microchannel fibers. Scale bar=200 µm.

FIG. 12A is a confocal microscope image of immunostaining for neurofilament demonstrate neurite extension within Matrigel-coated porous PCL fiber channels. Scale bar=1 mm.

FIG. 12B is a confocal microscope image of immunostaining for neurofilament demonstrate neurite extension within Matrigel-coated non-porous PCL fiber channels. Scale bar=1 mm.

FIG. 12C is a confocal image of neurite extension, as marked by neurofilament immunostaining, from DRGs seeded on Matrigel-coated porous PCL films. Scale bar=1 mm.

FIG. 12D is a confocal image of neurite extension, as marked by neurofilament immunostaining, from DRGs seeded on Matrigel-coated non-porous PCL films. Scale bar=1 mm.

FIG. 12E is illustrates in vitro neurite extension between the fiber channels of FIGS. 12A (porous channel), 12B (non-porous channel), and the films of FIGS. 12C (porous channel), 12D (non-porous channel), as compared by a two-way ANOVA followed by post-hoc Tukey HSD test. Average neurite extension is greater in porous PCL channels than in non-porous channels (n=7 samples for porous channels and n=6 samples for non-porous channels; $p<0.05$). Neurite extension is significantly greater in channels than on flat PCL films independent of porosity (n=6 samples; $p<0.05$). No significant differences are found in neurite extension on porous and non-porous films ($p>0.05$). All values are mean±standard error of mean.

Figure 13A:
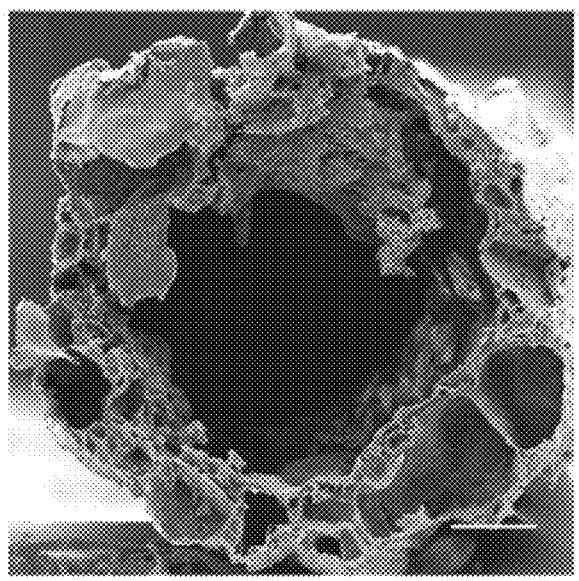

FIG. 13A is an image of a PCL fiber fabricated from unfiltered salt resulting in a wide pore size distribution. Scale bar=100 µm.

Figure 13B:
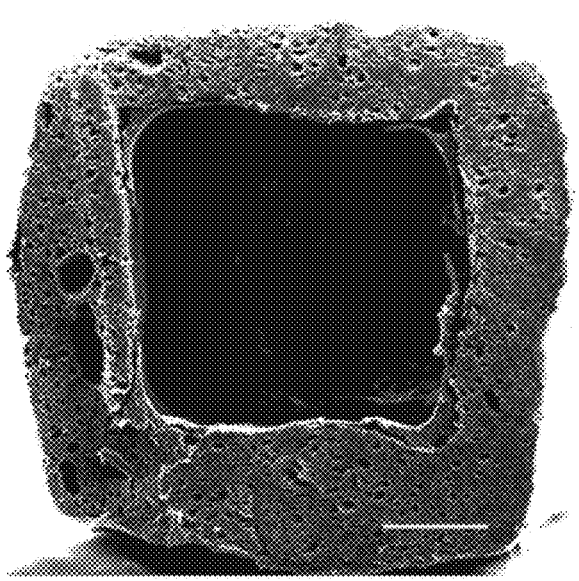

FIG. 13B is an image of a porous PCL structure with a square cross-section. Scale bar=200 µm.

Figure 14:
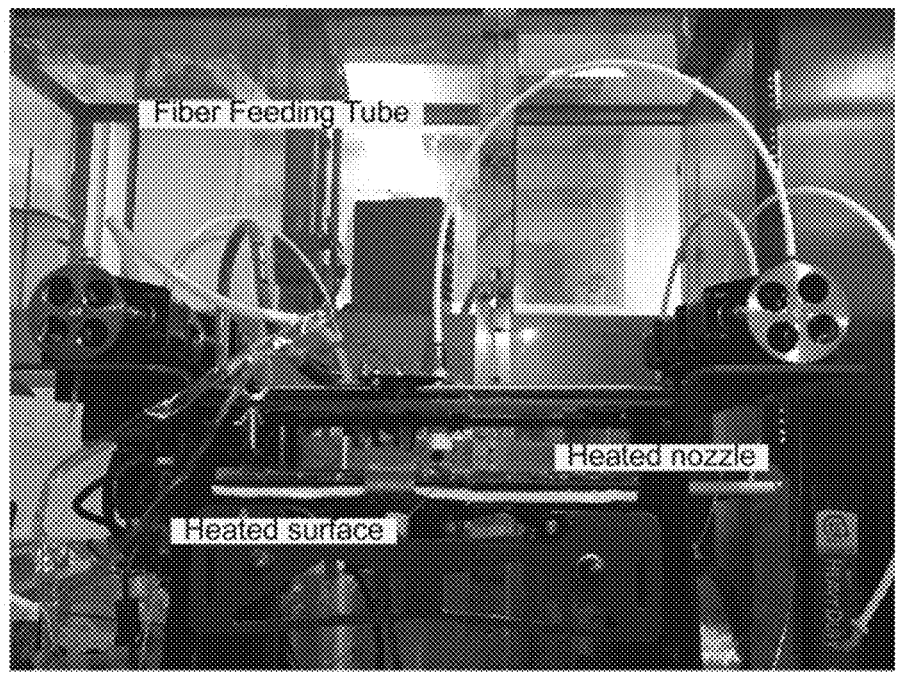

FIG. 14 is a photograph of components of an example fuse printing set up.

Figure 15A:
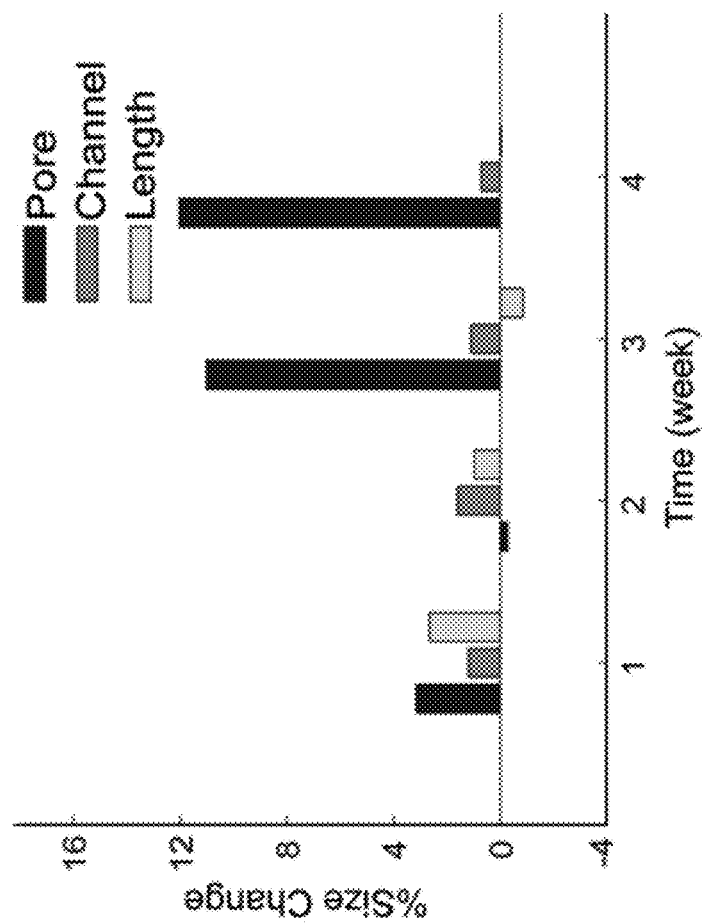

FIG. 15A is a plot illustrating differences in the dimensions of a printed bifurcated scaffold from its digital design. $W_{1-3}$ represents 3 different scaffold lengths. $R_{Curvature}$ is the scaffold radius of curvature.

Figure 15B:
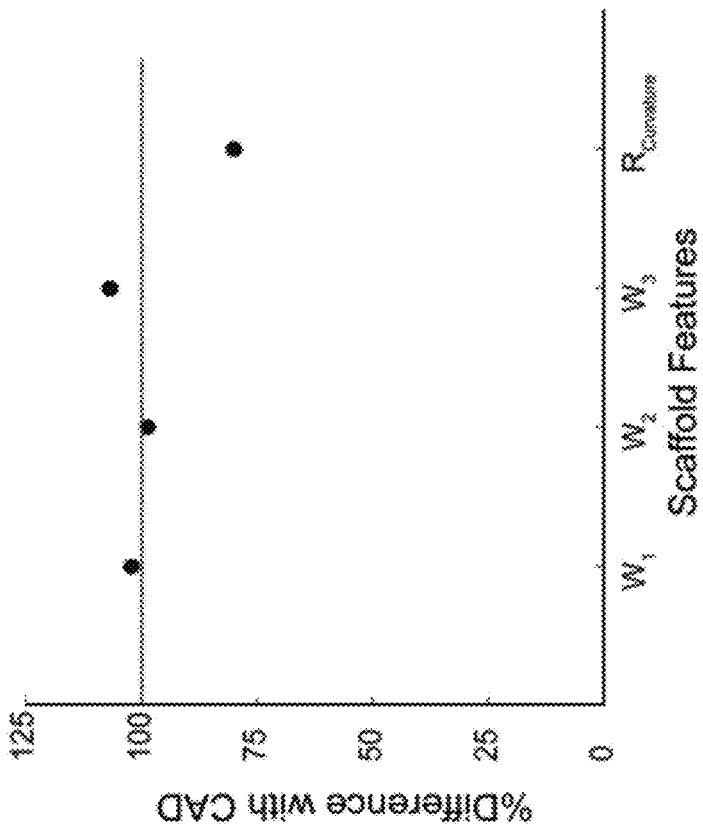

FIG. 15B is a plot illustrating quantitative analysis of the change in fuse printed scaffold pore size, channel inner diameter and scaffold outer length over 4 weeks when stored at physiological conditions.

FIG. 16A is an image of an AlamarBlue® assay of HEK293 cells in control settings. Scale bar=10 µm.

FIG. 16B is an image of an AlamarBlue® assay of HEK293 cells in the presence of a porous PCL film as a cytotoxicity test. Scale bar=10 µm.

FIG. 16C is an image of an AlamarBlue® assay of HEK293 cells in the presence of a porous PCL channel as a cytotoxicity test. Scale bar=10 µm.

FIG. 16D is an image of an AlamarBlue® assay of HEK293 cells in the presence of a fuse printed PCL scaffold as a cytotoxicity test. The cell morphology remains the same across FIGS. 16A-16D. Scale bar=10 µm.

FIG. 16E is a plot of changes in fluorescent intensity at 600 nm absorbance showing that films, fibers or scaffolds do not impede cell growth and proliferation when compared to cells grown in media alone.

FIG. 17A is a confocal microscopy image of a porous PCL channel for NF (neurofilaments) to illustrate co-staining for neurofilaments, Schwann cells and nuclei for DRG growth. Scale bar=20 µm.

FIG. 17B is a confocal microscopy image of a porous PCL channel for S100 (Schwann cells) to illustrate co-staining for neurofilaments, Schwann cells and nuclei for DRG growth. Scale bar=20 µm.

FIG. 17C is a confocal microscopy image of a porous PCL channel for DAPI (nuclei) to illustrate co-staining for neurofilaments, Schwann cells and nuclei for DRG growth. Scale bar=20 µm.

FIG. 17D is a confocal microscopy image that is a superposition of the images of FIGS. 17A-17C. Scale bar=20 µm.

FIG. 17E is a confocal microscopy image of a non-porous PCL channel for NF (neurofilaments) to illustrate co-staining for neurofilaments, Schwann cells and nuclei for DRG growth. Scale bar=20 µm.

FIG. 17F is a confocal microscopy image of a non-porous PCL channel for S100 (Schwann cells) to illustrate co-staining for neurofilaments, Schwann cells and nuclei for DRG growth. Scale bar=20 µm.

FIG. 17G is a confocal microscopy image of a non-porous PCL channel for DAPI (nuclei) to illustrate co-staining for neurofilaments, Schwann cells and nuclei for DRG growth. Scale bar=20 µm.

FIG. 17H is a confocal microscopy image that is a superposition of the images of FIGS. 17E-17G. Scale bar=20 µm.

FIG. 17I is a confocal microscopy image of a porous PCL film for NF (neurofilaments) to illustrate co-staining for neurofilaments, Schwann cells and nuclei for DRG growth. Scale bar=20 µm.

FIG. 17J is a confocal microscopy image of a porous PCL film for S100 (Schwann cells) to illustrate co-staining for neurofilaments, Schwann cells and nuclei for DRG growth. Scale bar=20 µm.

FIG. 17K is a confocal microscopy image of a porous PCL film for DAPI (nuclei) to illustrate co-staining for neurofilaments, Schwann cells and nuclei for DRG growth. Scale bar=20 µm.

FIG. 17L is a confocal microscopy image that is a superposition of the images of FIGS. 17I-17K. Scale bar=20 µm.

FIG. 17M is a confocal microscopy image of a non-porous PCL film for NF (neurofilaments) to illustrate co-staining for neurofilaments, Schwann cells and nuclei for DRG growth. Scale bar=20 µm.

FIG. 17N is a confocal microscopy image of a non-porous PCL film for S100 (Schwann cells) to illustrate co-staining for neurofilaments, Schwann cells and nuclei for DRG growth. Scale bar=20 µm.

FIG. 17O is a confocal microscopy image of a non-porous PCL film for DAPI (nuclei) to illustrate co-staining for neurofilaments, Schwann cells and nuclei for DRG growth. Scale bar=20 µm.

FIG. 17P is a confocal microscopy image that is a superposition of the images of FIGS. 17M-17O. Scale bar=20 µm.

Figure 17Q:
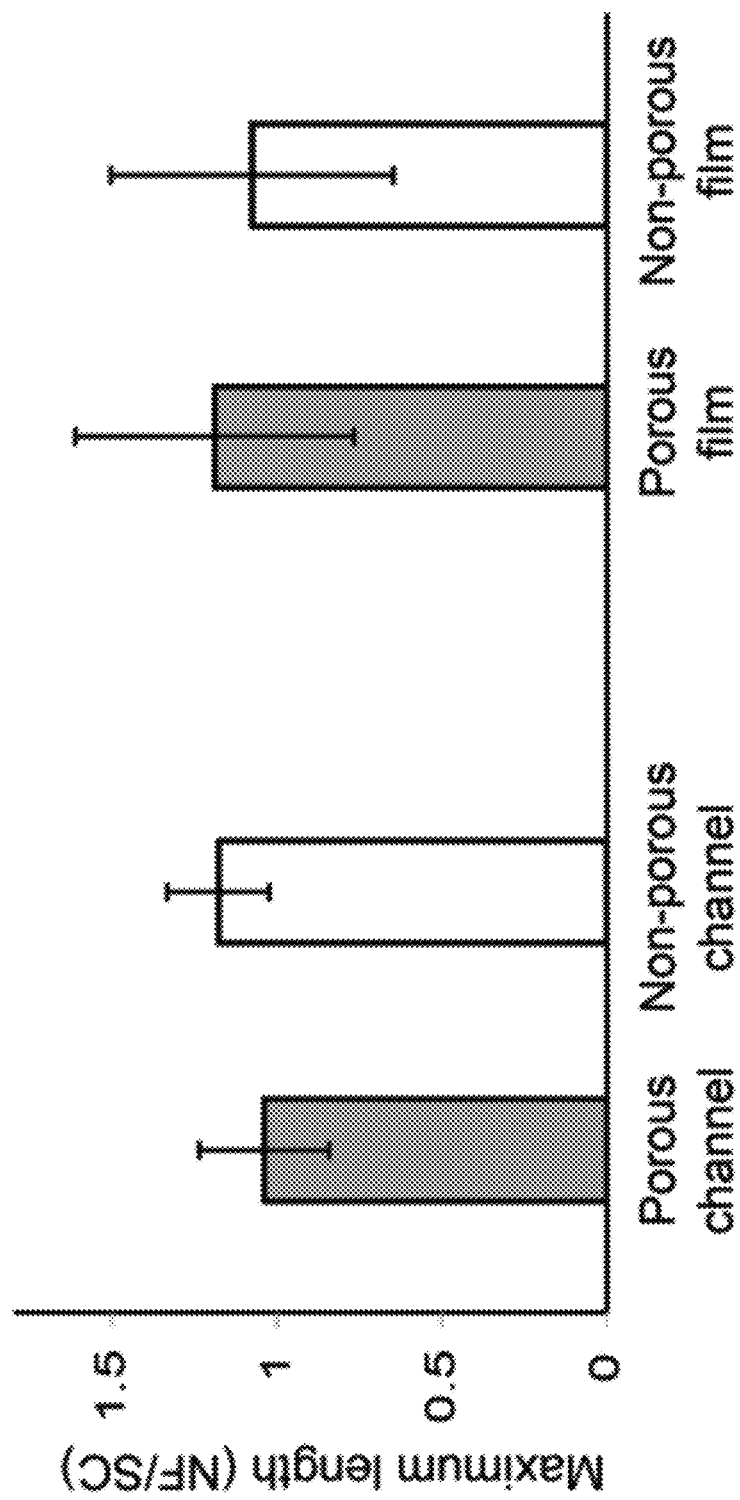

FIG. 17Q is a plot illustrating the ratio of maximum growth length for neurofilaments versus Schwann cells indicating similar growth length for the two types of cells.

Figure 18:
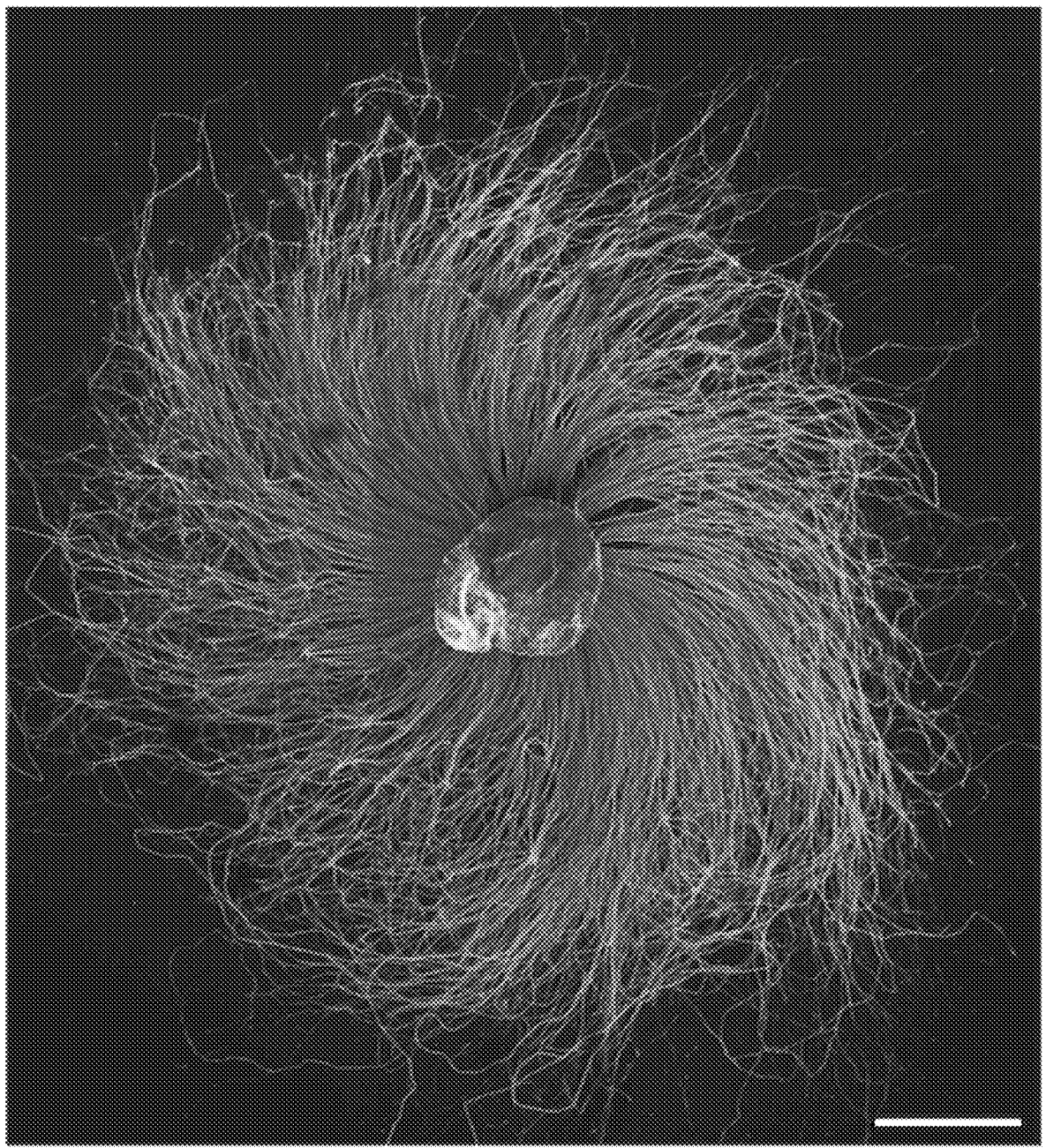

FIG. 18 is an image of a dorsal root ganglion (DRG) grown on a Matrigel™-coated glass cover slip for 12 days. Scale bar=500 µm.

FIG. 19A is a schematic illustration of transplanting a scaffold/construct to VML (volumetric muscle loss) mouse model.

FIG. 19B shows pictures of an example protocol of transplanting porous fiber (pFiber) and porous film (pFilm) to the injury site of the VML mouse model of FIG. 19A. A Hyaluronic acid (HA) patch was used to prevent the scaffold from moving out of the injury site. $NaIO_4$ was used for gelation.

Figures 19C, 19D:
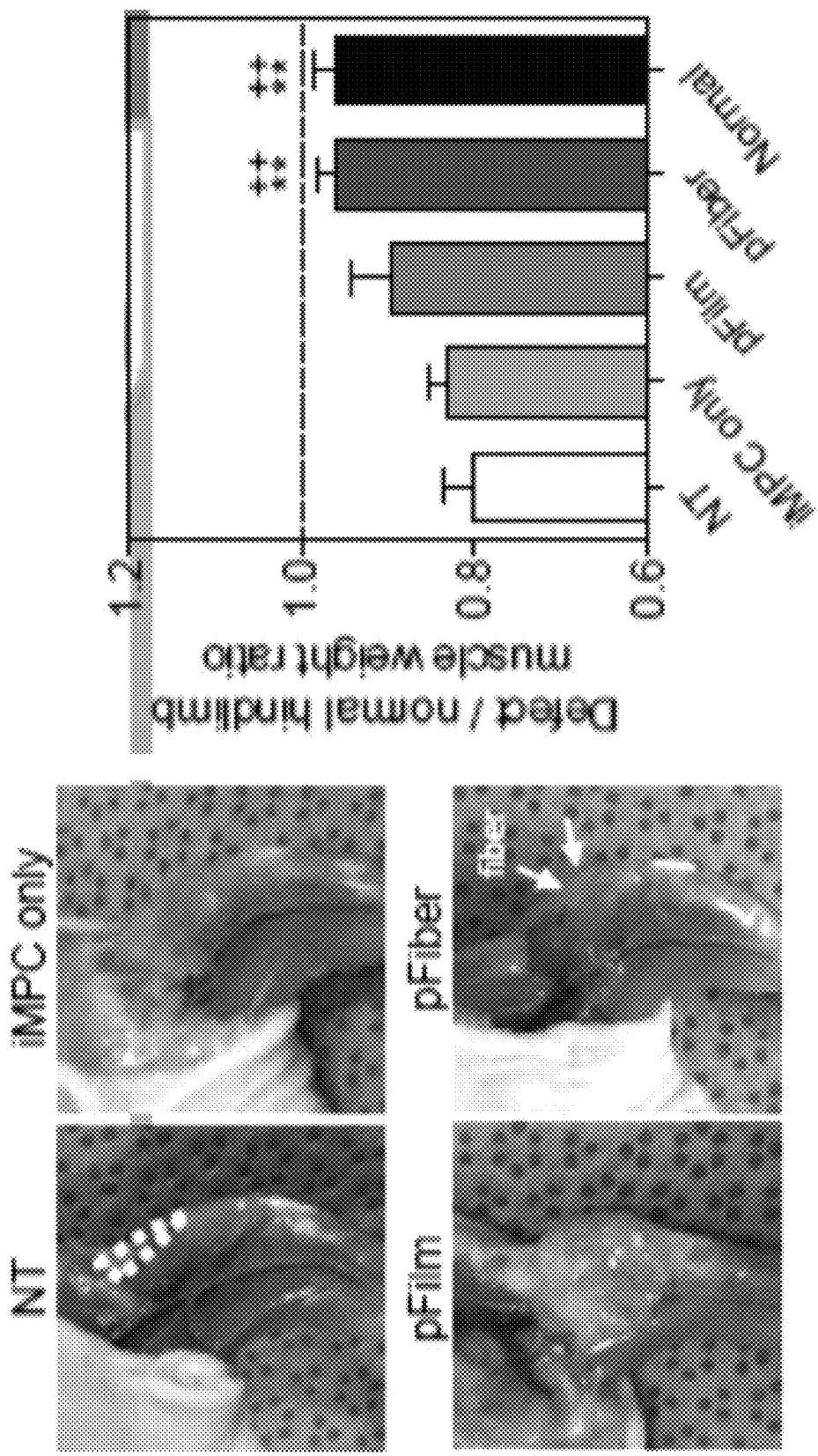

FIG. 19C shows pictures of the injury site a mouse model of FIG. 19A after 4 weeks of transplantation.

FIG. 19D is a plot illustrating the ratio of the defected and contralateral hind limb weight after 12 weeks of post-transplantation (**P<0.01 versus no treat (NT), and ++P<0.01 versus Normal group) in the mouse model of FIG. 19A.

Figures 19E, 19F:
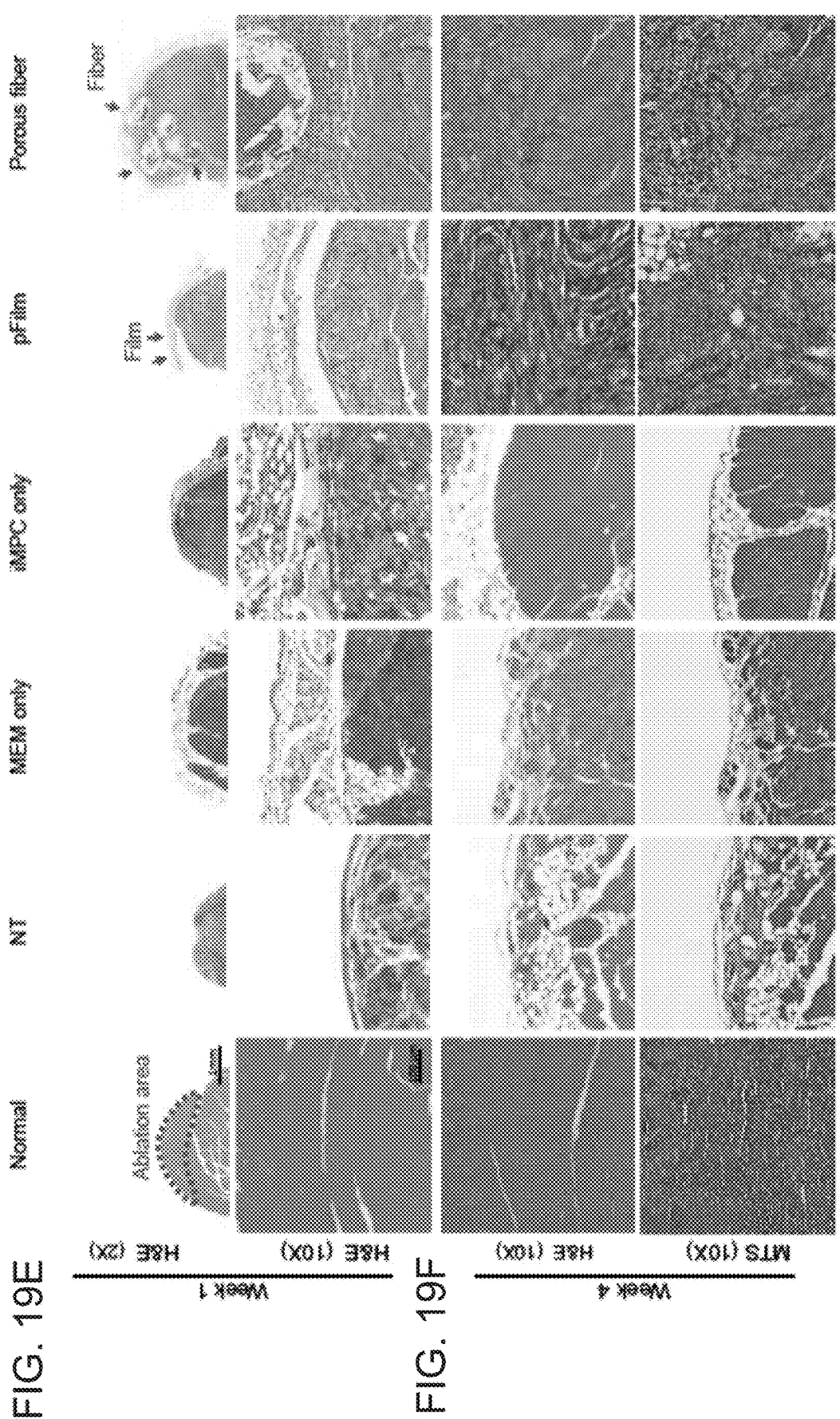

FIG. 19E shows representative images of hematoxylin and eosin (H&E)-stained cross-sections of VML-injured quadriceps femoris muscles treated with different scaffolds at the proximal regions of the newly formed area from the host tissues after 1 week of transplantation (scale bars=1 mm and 100 µm). The black dotted lines represent the boundary between the defect and host region.

FIG. 19F shows representative images of H&E and Masson's trichrome (MT) staining at the de novo regions at week 4. The ablated regions were imaged in NT, muscle extracellular matrix (MEM) only and skeletal muscle progenitor cells (iMPC) only groups as there were no newly formed muscle tissue (scale bar=100 µm).

Figure 20A:
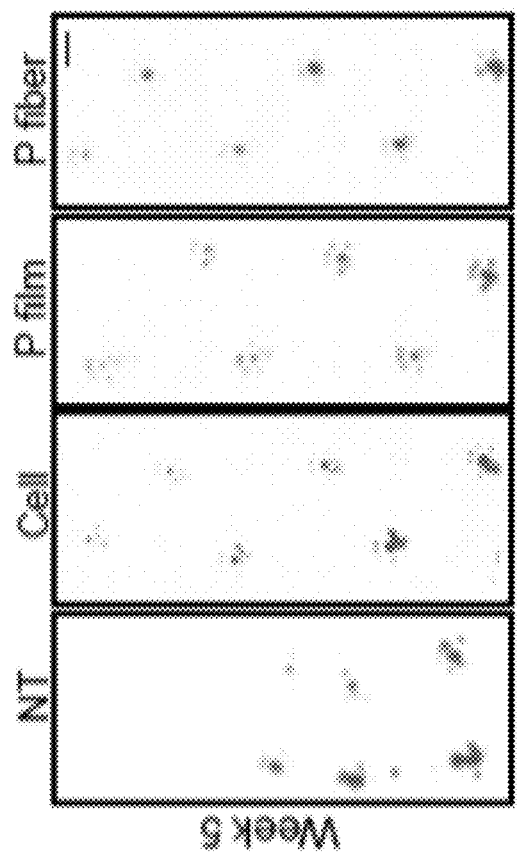
Figure 20A:
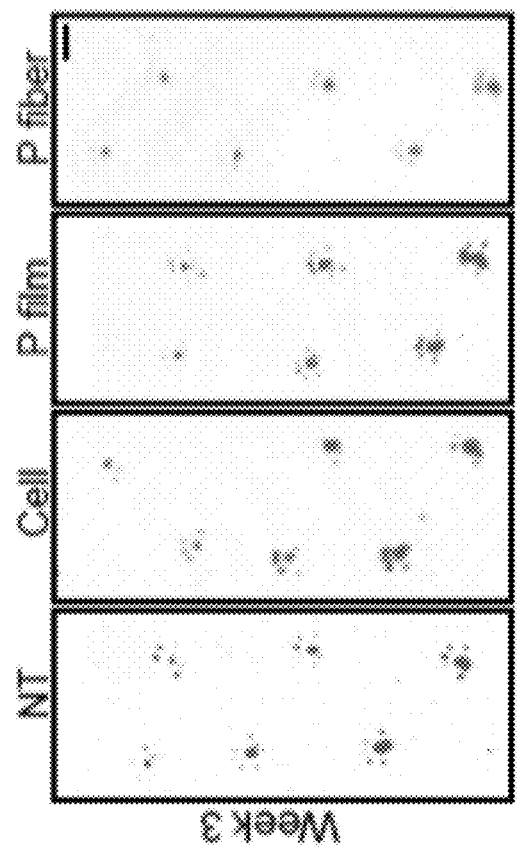

FIG. 20A illustrates gait analysis for the VML injured mouse model of FIG. 19A, at weeks 3 and 5.

Figure 20B:
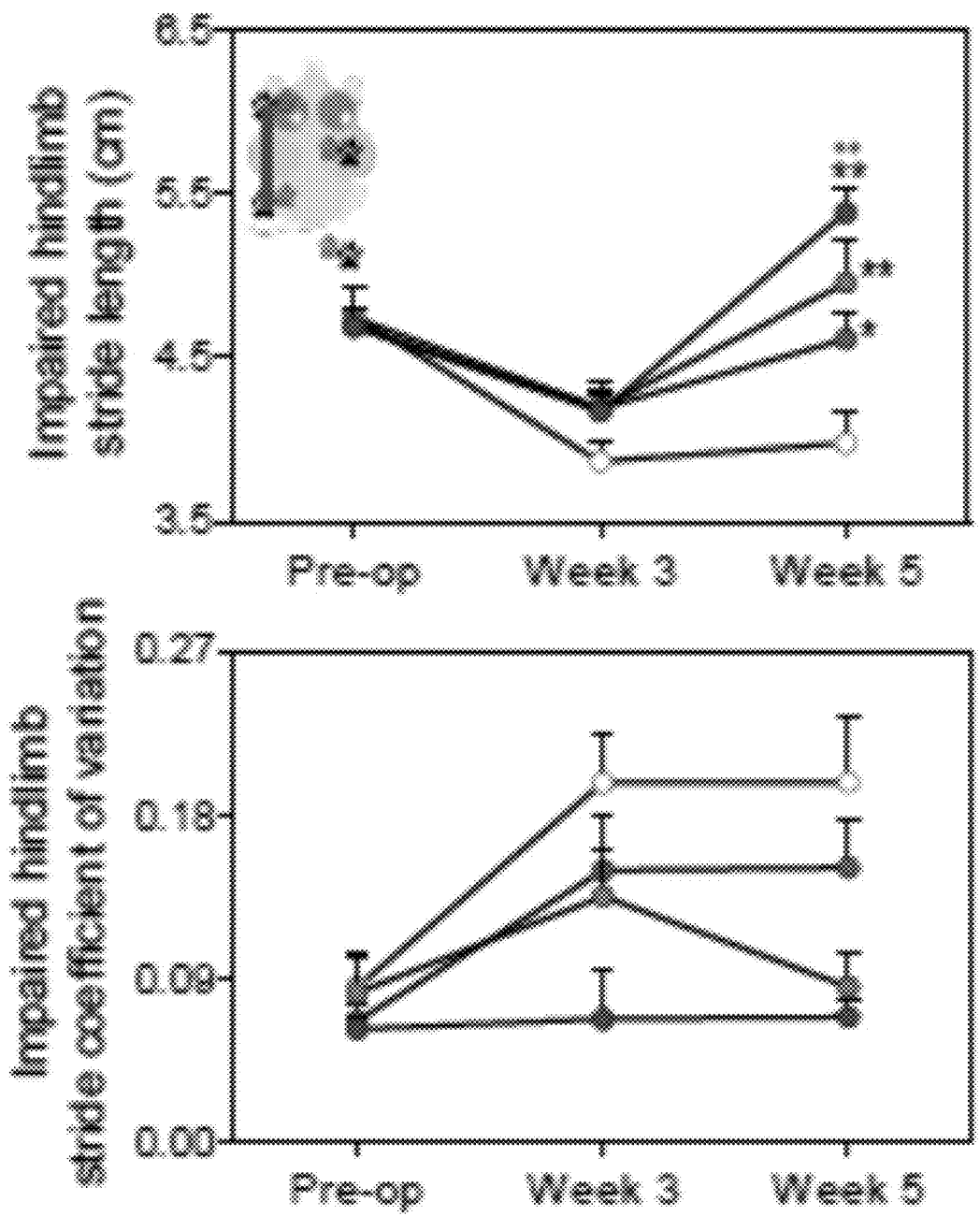

FIG. 20B illustrates how transplantation of porous tubes improves functional performance of the VML mouse model of FIG. 20A, and shows gait analyses of stride length and coefficient of variation at weeks 3 and 5 (*p<0.05 and **p<0.01 versus NT, +p<0.05 and ++p<0.01 versus iMPC, and #p<0.05 versus pFilm groups at the same time point, n=10 for week 4, and n=4~5 for week 8).

Figure 20C:
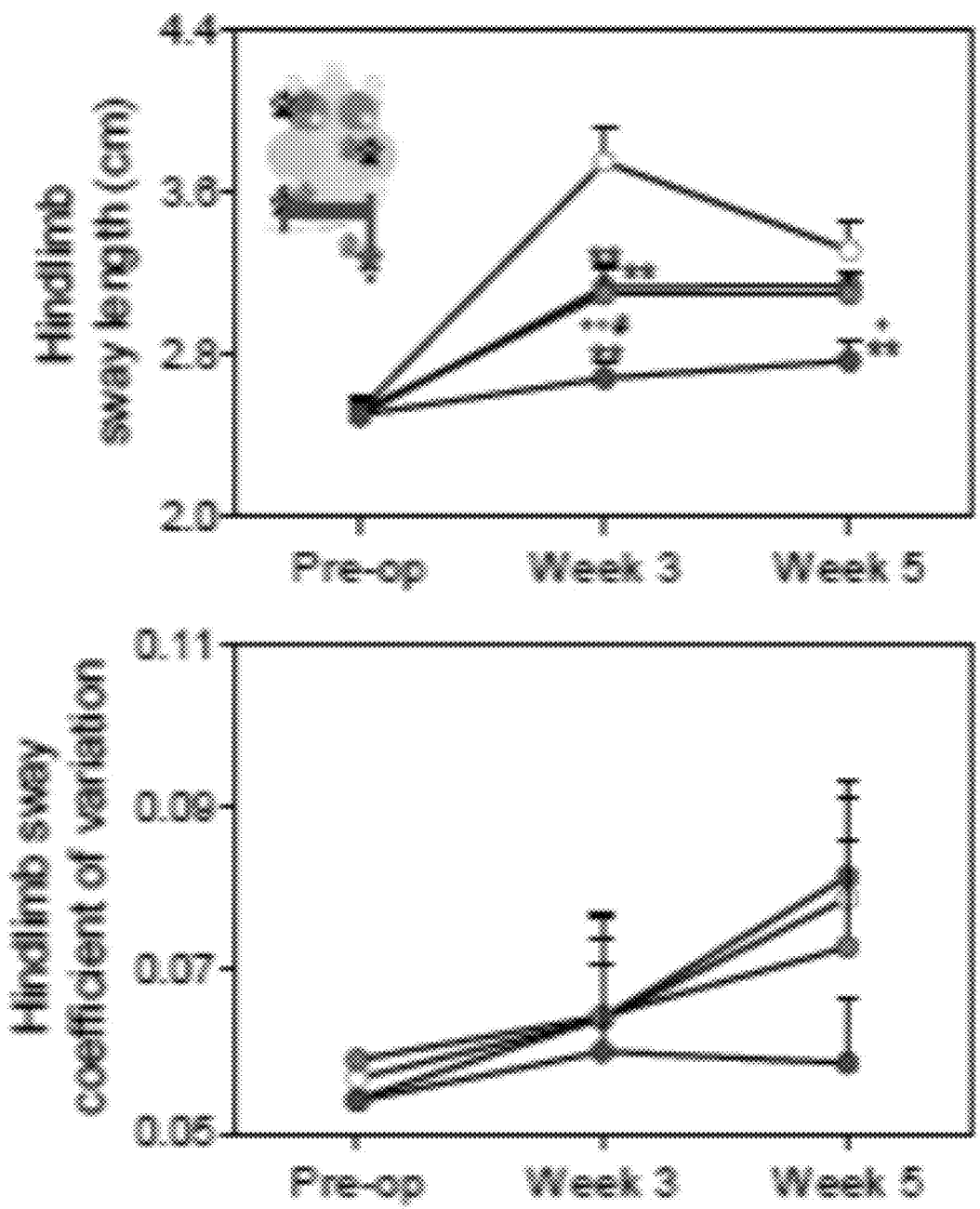

FIG. 20C illustrates how transplantation of porous tubes improves functional performance of the VML mouse model of FIG. 20A, and shows gait analyses of sway length and coefficient of variation at weeks 3 and 5 (*p<0.05 and **p<0.01 versus NT, +p<0.05 and ++p<0.01 versus iMPC, and #p<0.05 versus pFilm groups at the same time point, n=10 for week 4, and n=4~5 for week 8).

Figure 20D:
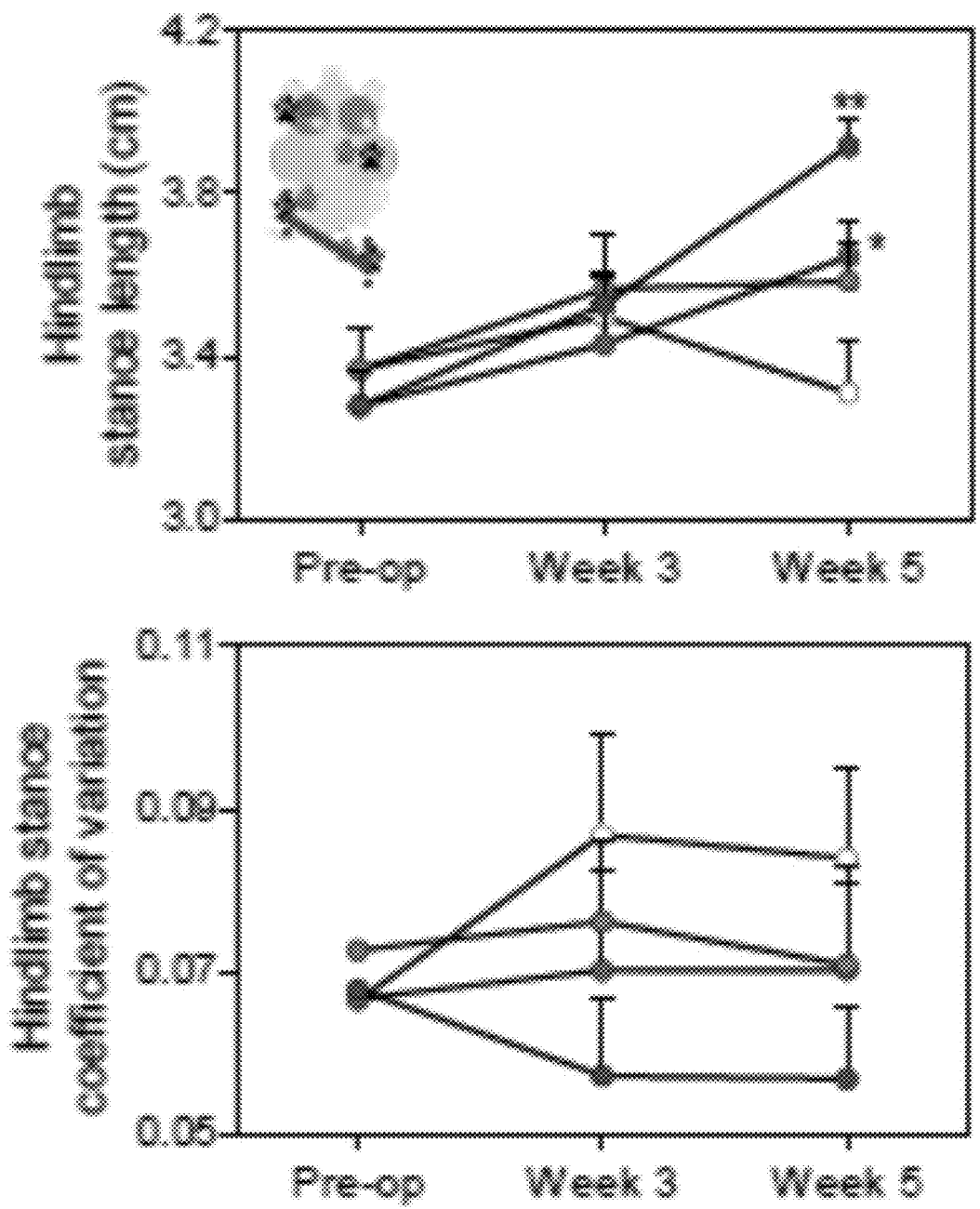

FIG. 20D illustrates how transplantation of porous tubes improves functional performance of the VML mouse model of FIG. 20A, and shows gait analyses of stance length and coefficient of variation at weeks 3 and 5 (*p<0.05 and **p<0.01 versus NT, +p<0.05 and ++p<0.01 versus iMPC, and #p<0.05 versus pFilm groups at the same time point, n=10 for week 4, and n=4~5 for week 8).

Figure 20E:
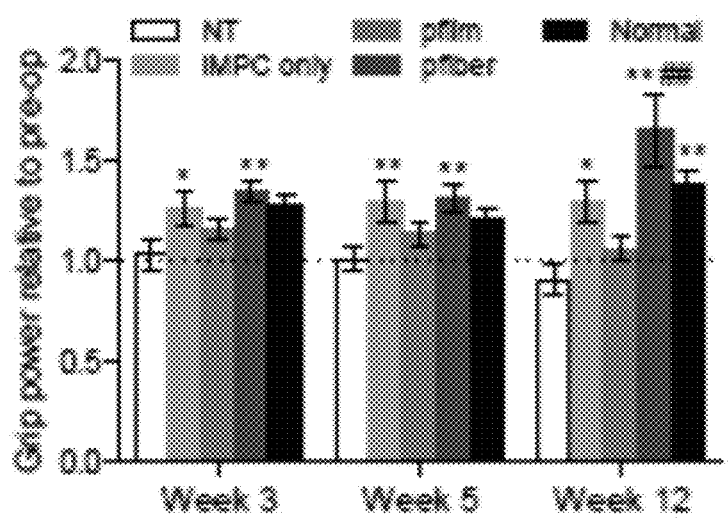

FIG. 20E is a plot illustrating the results of grip strength tests in NT, iMPC only, pFilm, pFiber, and Normal group (*p<0.05 and **p<0.01 versus NT, and ##p<0.01 versus pFilm group, n=10~15 for weeks 3 and 5, and n=5~10 for week 12.

Figure 20F:
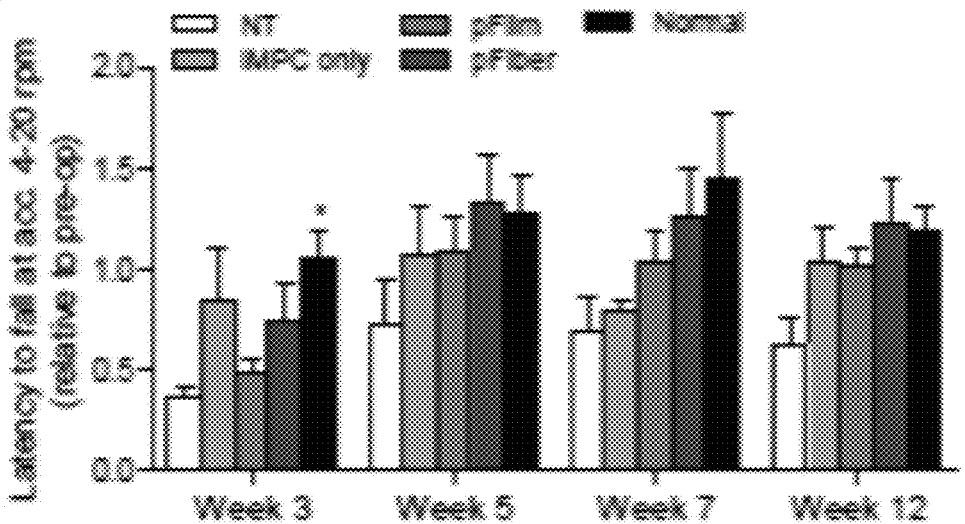

FIG. 20F illustrates the results of Rotarod tests conducted at an accelerating speed from 4 to 20 rounds per minute (rpm). Statistical difference between the groups was determined with two-way analysis of variance followed by Bonferroni post-tests.

Figure 20G:
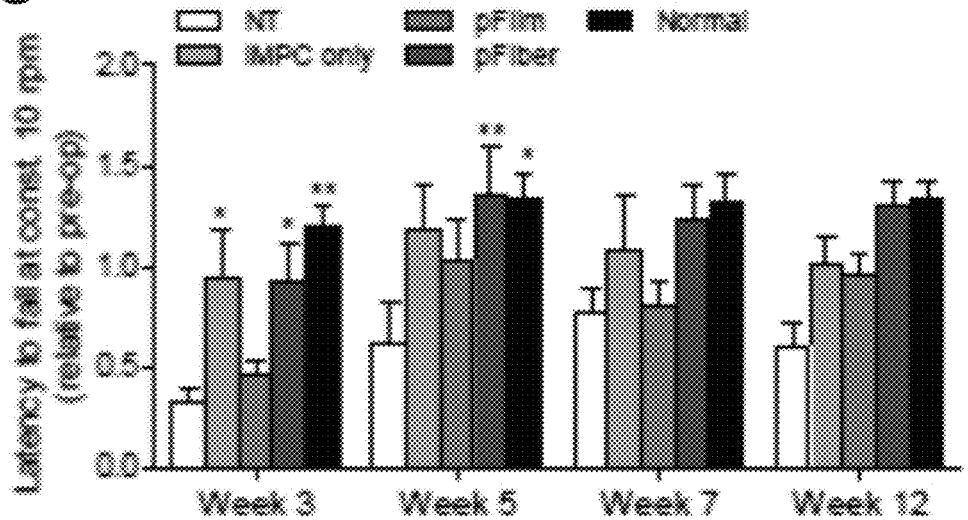

FIG. 20G illustrates the results of Rotarod tests conducted at constant speeds of 10 rpm (*p<0.05 and **p<0.01 versus NT groups, n=10~14 for weeks 3 and 5, and n=5~10 for week 7 and 12). Statistical difference between the groups was determined with two-way analysis of variance followed by Bonferroni post-tests.

DETAILED DESCRIPTION

Overview

Disclosed herein are methods for making porous scaffolds for tissue growth and other applications, such as air purification and/or water filtration. These scaffolds include thermally drawn fibers. Fibers are 3D printed to produce complex scaffold geometries with multiple inner channels. A scaffold can include, but is not limited to, thermoplastics, and can be composed of multiple materials. The pore size and/or porosity distribution of the scaffold can be controlled to be a target/predetermined value or range. For example, the target pore size/diameter can be in a range from about 0.1 µm to about 500 µm, e.g., 6 µm to about 100 µm, including all values and sub-ranges in between.

Also disclosed are methods of making porous tissue scaffolds for neural tissue growth. The scaffold can include inner channels or microchannels in complex shapes matching a naturally-occurring nerve and/or any targeted structure/geometry. Each microchannel can include a porous wall having a thickness from about 10 µm to about 500 µm, or more. The porous wall can include a biocompatible and biodegradable material including one or multiple polymers. The polymers may be any suitable thermoplastic such as, but not limited to, polycaprolactone, poly(lactic-co-glycolic acid), polylactic acid or other thermoplastics, and combinations thereof. Such methods may include tuning a crystalline size to a desired size range, mixing a crystalline with a polymeric solution to form a suspension. The polymeric solution is cast into films. The films are then rolled around a different material to generate a preform that is then thermally drawn. Over meters of tubes/fibers can be produced, with the outer geometries and/or wall thicknesses being dictated by the preform dimensions.

Also disclosed are methods of making a porous scaffold based on an image. For example, for generating a scaffold to address nerve tissue repair, this image can be an MM scan or image of a nerve tissue or nerve tissue injury site that is meant to be implanted for example. To fabricate these scaffolds, fuse printing can be employed, such as can be carried out by a 3D printer that includes a heated nozzle. The thermally drawn fibers described above, with or without the crystalline particles removed, can be passed through the heated nozzle, which included a heated end. The diameter of the heated end can correspond to the fiber's outer diameter. The heated fibers can be printed onto an underlying polymeric film for adhesion of the first printed layer to the print bed. The resultant scaffolds can have inner channels with target dimensions and geometries. The resulting scaffold can then be implanted at the target nerve injury site.

Nerve Repair

As an example application for the porous scaffolds manufactured according to the methods provided herein, nerve repair can be improved when growing neurons are supported and linearly guided via an implanted scaffold. FIGS. 1A-1G generally illustrate that for spinal cord, a scaffold with dimensions similar to the nerve gap is placed in the lesion. For the peripheral nerve it may be desirable to suture the scaffold to the nerve stubs at both ends to stabilize its position.

Fiber Fabrication

Provided herein are scaffold fabrication techniques that yield microchannel scaffolds with flexibility over scaffold constituents and dimensions, controlled porosity and predefined outer geometries.

A thermal drawing process (TDP) is adapted to produce scaffolds. During TDP, a cm-scale construct/preform is precisely machined to have a targeted composition of one or multiple components. The components can be thermoplastics with similar glass transition temperatures ($T_g$), such anywhere as from 60° C. to 320° C., including all values and sub-ranges in between. One or more metals may be incorporated into the preform, so as to create electrodes inside, and to develop conductive channels/scaffolds in turn. The preform is then heated (e.g., placed in a furnace with a temperature above the $T_g$ of the materials (if applicable)) and tension is applied. Fibers with a cross-section similar to the preform, but at a smaller scale (usually 5-200× smaller in diameter than the preform), are produced from the preform via TDP. This technique allows scaffold production on a large scale, with at least tens of meters of fiber generated in a single draw. The high yield of TDP makes this technology a particularly useful approach for precise reproducibility and higher availability of the products to researchers and consumers.

Figure 1G:
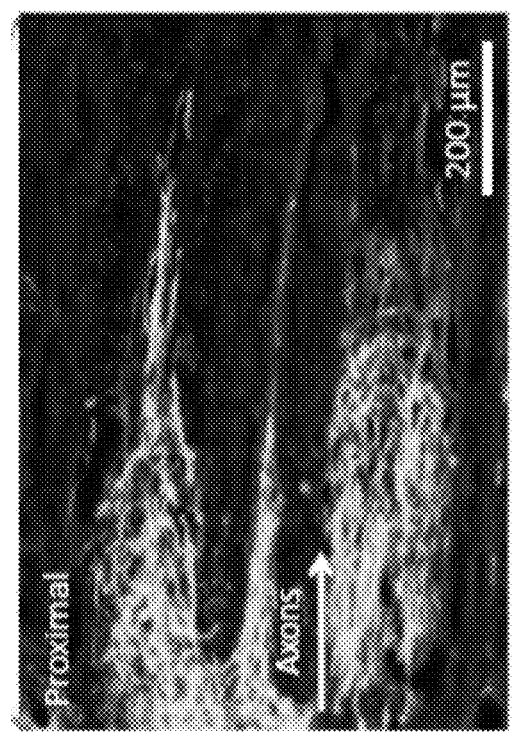
FIG. 1G is an image of an example nerve guidance scaffold 4 weeks after implantation in a rat's spinal cord. The staining is for neurofilaments showing the linear growth of axons along the scaffold channels.
Figure 1F:
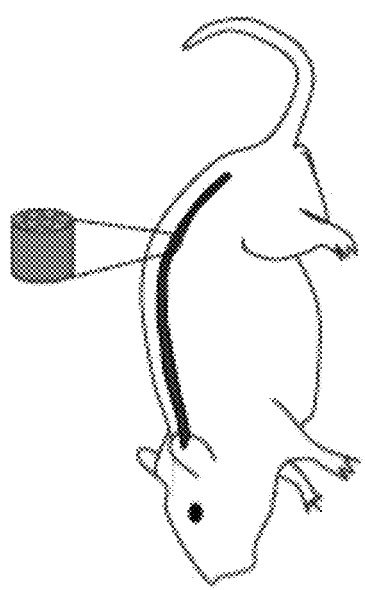
FIG. 1F is an illustration of scaffold placement in a rat's spinal cord.
Figure 1E:
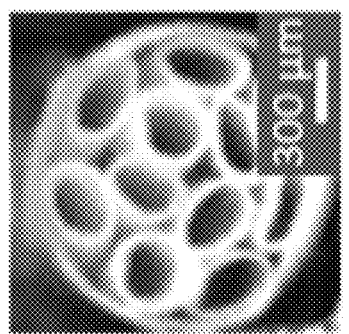
FIG. 1E is an image of a polycaprolactone (PCL) scaffold.
Figure 2A:
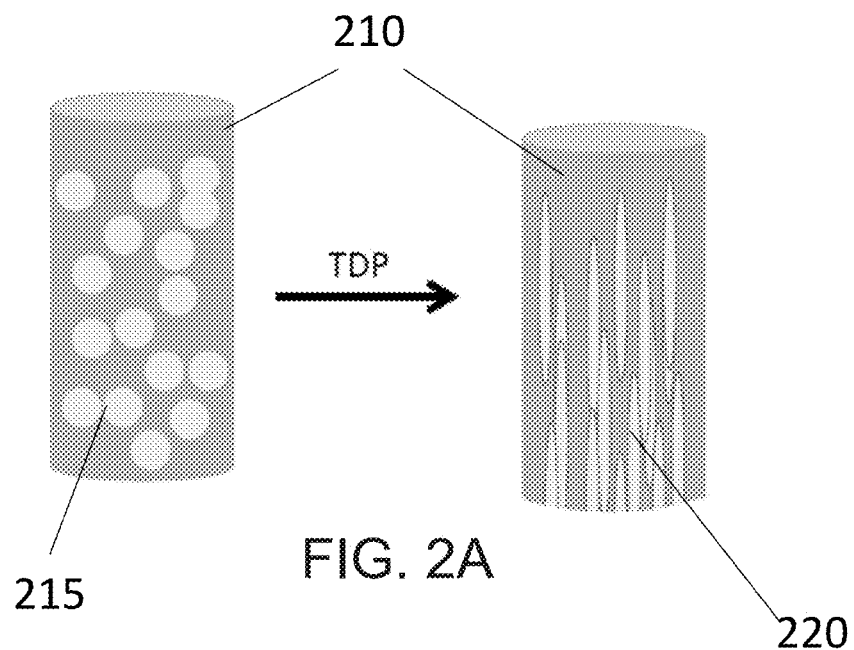
FIG. 2A illustrates a porous scaffold (right side) generated by thermal drawing of a porous preform (left side).
Figure 2B:
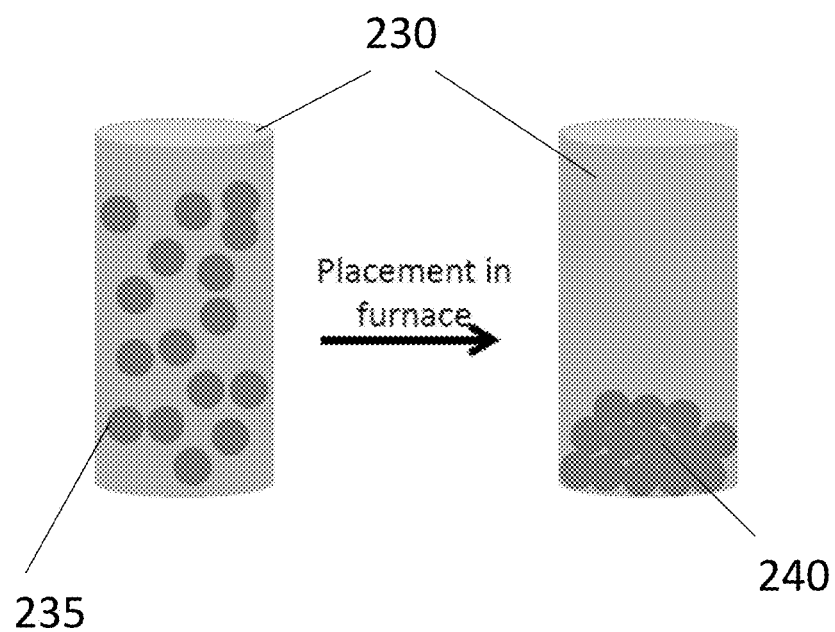
FIG. 2B illustrates the resulting preform obtained upon mixing of a preform polymer solution with pore-forming particles.

TDP is an established technique to produce fibers with targeted geometries and sizes. However, generating porous scaffolds via TDP is challenging, as illustrated in FIGS. 2A-2B. FIG. 2A illustrates how introducing porosity via pores 215 in a preform 210 before stretching via TDP results in tears within the final fiber after TDP. Specifically, the pores 215 in a preform get stretched into elongated pores 220 as illustrated, resulting in a mechanically fragile fiber 210 after TDP. FIG. 2B illustrates how merely combining a pore-forming particle (also sometimes referred to as a 'porogen') 235 with a polymer solution 230 when generating the preform is inadequate, since the particles 235 tend to aggregate into clumps 240 at the bottom of the solution, resulting in uneven distribution. Accordingly, to expand the use of TDP to a wide range of thermoplastics and to precisely control pore size and porosity distribution, a new approach is required.

To circumvent these challenges, the process of salt leaching is combined with TDP to introduce and control porosity, as illustrated in FIG. 3A. Generally, salt leaching characterizes an approach where salt crystals, such as common salt crystals (sodium chloride, or NaCl), are combined with a fiber-forming polymer such that the salt crystals end up embedded in the walls of the resulting fiber, and can then be removed at some stage to leave behind pores having desirable dimensions, distribution, etc. However, as shown in FIG. 2B, merely combining salt particles with a polymer-containing solution prior to drawing is inadequate, and the process illustrated in FIG. 3A overcomes these shortcomings.

At step 310 in FIG. 3A, ground sodium chloride (NaCl) is filtered to a desired size and/or size range (e.g., that of a desired pore size of, for example, 0.1 μm to about 500 μm, including all values and sub-ranges in between), though any suitable salt compound can be employed. For example, a single filter can be used to obtain salt particles below a desired size. As another example, two or more filters can be used to obtain salt particles within a desired size range. The ground salt particles and/or the filter salt particles can be further ground down to a desirable size via ball milling. Generally, while described herein with respect to NaCl particles, any suitable salt having a melting temperature above the drawing temperature of the TDP process can be used.

At step 320, the filtered salt particles is mixed with a thermoplastic/polymer solution in a concentration that can yield a desired porosity and/or porosity range in the resulting fiber such as, for example, from less than 1%, up to 45%, including all values and sub-ranges in between. The solution includes the thermoplastic dissolved in a suitable solvent. At step 330, the solution is doctor bladed into a film. At step 340, the film is rolled around a core composed of a sacrificial material, i.e., a material that can be removed later to yield an inner channel of the fiber. Examples of such a sacrificial material includes any suitable material with a $T_g$ close to that of the polymer, such as polystyrene or teflon. Optionally, an additional layer/cladding of a sacrificial material (which can be the same material as the core or different) can be placed around the rolled film to generate the preform, as best illustrated in FIG. 3B. As also shown in step 330 of FIG. 3B, the preform can then be thermally drawn into a fiber. Several meters of fibers can be produced in this manner, with the outer geometries and/or wall thickness of the constructs being dictated by the preform dimensions. The sacrificial material and the salt particles can then be removed simultaneously or in a sequential manner. For example, the sacrificial material can be chemically removed, while the salt particles can be removed by dissolution in water or ethanol.

Fiber Characterization

PCL can be used as the main fiber-forming polymer/material, though other thermoplastics such as polylactic acid can also be employed. Hollow fibers with targeted pore size and porosity distribution, with circular and square cross-sections of different widths can produced, as illustrated in FIGS. 4A-4I, 9D-I. Pore sizes in the fibers can generally correspond to sizes of the salt particles used to make the preform, while the volume ratio of salt to fiber-forming polymer can determine the porosity (e.g., as a volume percentage), as illustrated in FIGS. 4J, 4K, 10A-10H. When imaging is used to evaluate porosity, observed pores can appear smaller than the target pore size (i.e., smaller than the size of the target salt particles) as a result of the viewing angle, which may prevent complete imaging and measurement of the true size of those pores. Pores larger than salt sizes may be the result of the occasional agglomeration of salt particles during preform fabrication. The interconnected porosity, which can be a quantitative or qualitative measure of pores that are connected and therefore enable mass transport between pores, and salt-leaching rate of the fiber, can be monitored via Elemental Dispersion X-ray (EDX) analysis, such as on PCL fabricated using a salt particle-polymer solution mix with 35% (v/v). The salt-leaching rate can characterize how fast the salt-leaching can be done.

An example EDX analysis is shown in FIGS. 4I-4N, conducted on a meters long PCL fiber with a 300 μm inner diameter that was cut into 1 cm-long sections, and the sacrificial material was then chemically removed from both inner core and the outer layer. The fibers were then either analyzed prior to salt-leaching (i.e., removal of the salt particles) or placed in water for periods of 1 or 24 hours. The EDX analysis was performed on the midline cross-sections of the fibers to detect salt particles prior to and during salt-leaching. Average percentage of salt particles was 85 v/v % before salt-leaching, 67.4 v/v % after 1 hour and 2.6 v/v % after 24 hours of salt-leaching. Salt removal indicates that the inner pores were interconnected for the salt to be dissolved. Said another way, the solvent (e.g., here, water), can flow or propagate between interconnected pores and dissolve the crystalline. If the pores were not interconnected, since the middle of the fiber was not exposed to the solvent, the removal of salt particles would have to be done through penetration of water through the non-porous polymer itself, which can take several days and longer.

In addition, as theoretically predicted, introducing pores reduces the elastic moduli of these PCL fibers. Tensile testing on these PCL fibers indicates a 76.2% decrease in the elastic moduli from non-porous PCL to 35 v/v % porous PCL (i.e., reduction from 294.3 kPa to 70.0 kPa). In this manner, TDP combined with salt-leaching can be useful for modulating fiber porosity as well as its mechanical properties, and in turn, the same properties for the resulting scaffold.

Scaffold Fiber Fabrication

Once the fiber is generated, porous scaffolds can be produced therefrom, having multiple inner channels with complex targeted outer geometries, without restrictions in length or cross-sectional dimensions. An example printing technique, termed filament surface heating, can be employed to 3D-print the thermally drawn conduits. Unlike most 3D printing techniques, and similar to thermal drawing, filament surface heating provides flexibility over the material choice by which most thermoplastics can be printed, since heating of the thermoplastic to promote adhesion after printing is desirable. Accordingly, any suitable approach capable of heating the fiber during deposition above the $T_g$ for the fiber-forming polymer can be employed.

Prior to printing, the sacrificial polymer/material can be removed from the fiber (e.g., both from its core and the outer layer) by selective chemical etching. If the salt particles have not already been removed, they can be removed at this stage, or be left in place. As best illustrated in FIG. 3D, at step 335, the fiber is then fed into a printing nozzle with an outer diameter slightly larger than the outer diameter of the fiber, and surface heating occurs at the printing nozzle. The fiber passes through the nozzle and is deposited, and such a deposited fiber can also be referred to as a filament. In this manner, a deposited fiber/filament with a heated surface for fusion between adjacent deposited filaments/printed lines is generated. As shown in FIGS. 5A-5J and also FIGS. 9O, 11A-C, the printing of the fiber can be in the form of a scaffold with filaments stacked together and having a desirable geometry, e.g., one matching a shape drawn with a computer-aided design (CAD) software, to generate a custom-printed multichannel scaffold. As also illustrated in FIG. 3D, when the fiber is continuously deposited, the resulting deposited filaments can have closed ends, which can then be trimmed to expose their inner channels from one end to the other.

At this point, if the salt particles have not been removed, salt-leaching can be conducted (e.g., by dissolution in water or ethanol) to generate porous scaffolds. Fuse-printed scaffolds with hexagonal and triangle outer geometries, as well as scaffolds matching the structure of a spinal cord, can be generated while maintaining porosity, as best illustrated in FIGS. 5A-5J, and also FIGS. 9O-9P, 11.

FIGS. 5C, 9A in particular illustrates a scaffold that can replace a transected branched nerve, and has a bifurcated microchannel structure indicating that each nerve bundle can be separately guided from its neighboring nerve bundles. In this manner, a porous microchannel scaffold with matching outer geometry and dimensions consistent with that of an image (e.g., a magnetic resonance imaging (MRI) scan) can be produced in short time. With the meters-long fiber-production output of TDP, scaffolds can be printed with desired dimensions and lengths on a large scale. The fiber can be fed into the heating nozzle at step 335 non-continuously, which can lead to filament deposition and printing of scaffolds (i.e., via filament stacking) with a controlled mixture of varying inner diameter channels, channels formed from different materials or having different compositions, and/or the like. Such multi-diameter/material/composition scaffold can facilitate discovery of the most effective scaffold design for nerve repair in a particular clinical case.

FIGS. 6A-6E as well as FIGS. 12A-12E illustrate the testing of the application of thermally drawn porous scaffolds for nerve regeneration by culturing primary dorsal root ganglion (DRG) cells inside Matrigel-coated porous and non-porous PCL scaffolds. DRGs are isolated from newly born Fischer neonate rats, cut in half and placed at the tip of 300 µm inner-diameter filaments coated with Matrigel™. As seen in FIGS. 6A-6E, staining for neurofilaments 12 days post-culturing shows that neurites grew within the porous filaments of the scaffold, but not the non-porous ones. To test if nerve growth was suppressed within non-porous filaments due to lack of mass transport or because of the differences in surface morphology, DRGs were also cultured on Matrigel™-coated porous and non-porous PCL films where mass transport occurs on the surface of both films. The staining results after 12 days demonstrated statistically equivalent DRG growth, which suggests cell growth through the deposited fibers/filaments is more dependent on the wall porosity than surface morphology. Similar studies on fibronectin-coated conduits demonstrated growth only within porous scaffolds reinforcing the hypothesis that mass transport is essential for cm-long neurite growth TDP in combination with salt-leaching, and particularly in combination with the polymer-salt particle film formation process of FIGS. 3A, 9B, 9C, provides for a high-throughput scaffold fabrication method with control over pore size, mechanical properties and scaffold dimensions that can use different thermoplastics having different degradation rates and/or chemical properties. Printing the scaffolds using filament surface heating and via filament stacking, into complex structures that match CAD designs in short time and on a large scale, is particularly useful to different fields in the clinic and industry where material choice, porosity and inner and outer structures need to, or are desired to, be precisely tailored.

Example Methods for Scaffold Generation and Characterization

NaCl (Alfa Aesar) was ground using an automatic mortar and pestle (manufacturer). Nylon filter meshes with sizes of 28, 50, 79 and 101 µm (McMaster) were then used to produce salt particles with size ranges of <28 um, 28-50 µm, 50-79 µm and 79-101 µm by first using the smaller size mesh and then the mesh with the upper size, when applicable. PCL (3 wt. %) (Sigma) was dissolved in chloroform (Sigma). PLA (4 wt. %) was dissolved in a 50:50 volume ratio chloroform and dichloromethane (Sigma). The polymer solutions were mixed with salt at the desired size range and volume percentages (up to 65 vol % salt) using a vortex (VWR). A T-shape aluminum piece was machined to a blade with a height of 1 mm for doctor blading. Polymer/salt mixtures were poured on a copper sheath for PCL and glass for PLA, and the Al blade was passed over the mixtures. The films were air-dried for at least 10 min for PCL and 30 min for PLA prior to removal, and the solvents were removed in vacuum for over 24 hours and 48 hours for PCL and PLA, respectively.

The films were wrapped around polystyrene (PS) (McMaster) as a sacrificial material with circular or square geometries and covered with a Teflon sheath/layer, which was then tightly taped. While polystyrene is used here as an example, any hydrophobic material can be employed. A uniform piece was obtained by consolidating the films around the rod in an oven at the following temperatures for 1 hr: 100% PCL at 63° C., PCL/salt at 70° C., 100% PLA at 73° C. and PLA/salt at 80° C. The tape and teflon sheath is then removed. For consolidated rods (preforms that the polymer/salt film has tightly formed around the preform), a 25.4 mm dimeter polystyrene rod was machined to have a hole in the middle with the size of the outer diameter of the consolidated rod (about 9 mm), and the rod was placed inside to generate the preform. For square cross-section fibers, machined PS slabs with consolidated PCL/PS pieces in a square cross-section shape were placed in a hot press at 100° C. for 1 hour and then, while maintaining the temperature, a 50 psi pressure was applied for 1 hour and then the preform was allowed to air cool to room temperature under pressure.

These preforms were vertically suspended inside a furnace at 200° C. for PCL and 240° C. for PLA before being thermally drawn. To remove the inner and the outer polystyrene, scaffolds were chemically etched by placing them in cyclohexane under gentle agitation for 2 days with the solution changed three times. The samples then underwent salt-leaching by placing them in ethanol under mild agitation for at least 24 hr.

The resulting fibers were cut with razor blades and coated with 3 nm of gold particles and imaged with a scanning electron microscope (SEM) (Model 6010LA; JOEL). Salt and pore size quantification were done with ImageJ software. For EDX analysis, thermally drawn PCL fibers with 35 vol % salt and an inner diameter of 0.3 mm were cut to 10 mm in length. After etching the polystyrene in cyclohexane for two days with solution changed three times, the samples were placed in ethanol for 0, 1 and 24 hr, transected in half, gold coated and assessed for NaCl presence using EDX (n=3). Tensile testing was done on non-porous and 35 vol % porous PCL fibers of about 15 mm in length and 0.3 mm inner diameter in a Dynamic Mechanical Analyzer (Model DMA Q800; TA Instruments) under a constant extension rate of 0.2 mm/min (n=5).

The PCL fibers with 35 vol % porosity generated with salt particles of 28-50 µm were thermally drawn as described above. About 5-7 m of the fibers with 0.3 mm inner diameter were then placed in cyclohexane for 12 hr, with the solution changed three times for the outer polystyrene to be completely removed, while the inner polystyrene was partially removed. The fibers were subsequently fed into a printing nozzle. The nozzle contained a short stainless steel hot end with a length of 0.3 mm to heat the fibers. The diameter of the hot end was 0.8 mm, which corresponded to the fiber outer diameter of 0.7-0.8 mm. The hot end temperature was 165-175° C., measured by a VWR thermocouple probe. The feeding speed was 100-120 mm/min. The PCL fibers were printed as filaments onto an underlying PCL film (thickness of 0.2 mm) for adhesion of the first printed layer of filaments to the print bed. The input layer height was set at the diameter of the filament. The three-dimensional design of the porous scaffold was drawn in Solidworks and was later processed by Slic3r to create a gcode for printing. The gcode of the printed scaffold was then read by Pronterface software, which communicated the XYZ print positions to the 3D-printer (Rova3D Multinozzle printer). After scaffold printing, any remaining sacrificial polymer inside the channel is chemically etched, followed by salt removal to result in porous filaments in the scaffold.

For in-vitro analysis, Non-porous and 35 vol % porous PCL fibers were sectioned to 10 mm in length. After the cyclohexane and salt were removed as described above, the fibers and PCL films with similar porosities were placed in ethanol and set in the biosafety cabinet under UV for 45 min. Maintaining the fibers in a sterilized atmosphere, the ethanol was replaced with sterilized phosphate buffer saline (1×DPBS) and exchanged three times for 15 min each and then air-dried. The fibers were either coated with Matrigel™ or fibronectin. For Matrigel™ coating, the fibers were left in reduced growth factor Matrigel™ (BD Biosciences) diluted 1:30 with a DRG medium (Neurobasal-A media supplemented with B-27 and glutamax; Life Technologies) for an hour at room temperature. Fibronectin coating was applied by placing the fibers in 50 µg/ml of fibronectin (Sigma) for 1 hour and air drying for 1 hour. The fibers were placed in a DRG medium in 24-well, non-tissue culture plates (VWR Scientific Products) for at least 2 hr. During this time, air bubbles were pressed out of the fibers using sterile tweezers. For the control experiments, 12-mm glass coverslips (Electron Microscopy Sciences) etched overnight with 10% hydrochloric acid solution (Sigma) and stored in 99% ethanol were used. The coverslips were dried over a flame and placed into 24-well plates and coated with Matrigel™ or fibronectin as described above.

DRGs were isolated from Sprague Dawley neonatal rats on postnatal days 1-2 (Charles River). Individual DRG explants were collected from the spinal column, and the nerve roots and connective tissue were removed. The isolated DRGs were sectioned in half and either placed inside the fibers at one end, or in the center of the films/coverslips. The media was changed on day 6 and the cultures were fixed on day 12 with 4% paraformaldehyde (Electron Microscopy Sciences) in 1×DPBS for 45 min. The samples were then rinsed with 1×DPBS and permeabilized with 0.1% Triton X-100 in 1×PBS for 25 min. Donkey serum (2.5%) was used to block the samples at 4° C. overnight. Samples were then incubated in 1:500 rabbit anti-neurofilament primary antibody (Abcam) diluted in 2.5% donkey serum for 2 hours at room temperature, rinsed 3 times in 1×PBS. Secondary antibody staining was done with 1:1000 donkey anti-rabbit Alexa Fluor® 568 IgG (Abcam) for 2 hr, followed by three washes. To stain the nuclei, the samples were then incubated with 30 µM 6-diamidino-2-phenylindol (DAPI) (Life Technologies) for 2 min and washed with 1×DPBS three times. The samples were mounted on glass slides in Prolong Gold Anti-fade (Abcam) prior to imaging with a confocal microscope (Olympus).

In summary, porous scaffolds that match the complex shape of nerves as well as bifurcated nerves can be used for nerve repair. To produce such scaffolds, a thermal drawing process is combined with salt-leaching to generate fibers with circular or square cross-sections with controlled pore sizes from less than 10 µm to over 100 µm, with a production rate of over tens of meters in a single experimental run. The fibers can have controlled wall thicknesses as low as 20 µm with precise inner diameters. To produce microchannel scaffolds with complex outer geometries that can also mimic branched neurons, thermally drawn fibers can be 3D printed as filaments by employing a filament surface heating technique. The printed scaffolds can have a structure that precisely matches computer-aided designs generated from imaging scans of nerve tissues. Culturing primary neural cells inside polycaprolactone filaments demonstrates the necessity of porosity for tissue survival and growth within one cm-long channels. Such a scaffold fabrication technique provides a clinically and commercially relevant process for nerve repair and can be transitioned to a variety of other applications that require constructs with targeted wall porosity and complex geometries, such as for muscle repair, for example.

Example 1—Scalable Fabrication of Porous Microchannel Nerve Guidance Scaffolds with Complex Geometries Microchannel scaffolds accelerate nerve repair by guiding growing neuronal processes across injury sites. Although geometry, materials chemistry, stiffness, and porosity have been shown to influence nerve growth within nerve guidance scaffolds, independent tuning of these properties in a high-throughput manner remains a challenge. Here fiber drawing is combined with salt leaching to produce microchannels with tunable cross-sections and porosity. This technique is applicable to an array of biochemically inert polymers and delivers hundreds of meters of porous microchannel fibers. Employing these fibers as filaments during three-dimensional printing enables the production of microchannel scaffolds with geometries matching those of biological nerves, including branched topographies. Applied to sensory neurons, fiber-based porous microchannels enhance growth as compared to non-porous channels with matching materials and geometries. The combinatorial scaffold fabrication approach may advance the studies of neural regeneration and accelerate the development of nerve repair devices.

Porous scaffolds with precise microstructures and geometries have benefitted from decades of refinement for a diversity of applications ranging from gas separation, water filtration, cell sorting, and tissue regeneration. Applied to nerve repair, these scaffolds are hypothesized to help maintain the organization of nerve bundles and linearly guide growing axons toward their pre-existing targets to restore injured neural pathways (FIG. 9A). Clinically available nerve guidance implants, however, are either limited in length, which reduces their utility in large (>4 cm) gap injuries, or mechanical flexibility, which can lead to adverse tissue response and pain. Furthermore, clinically available synthetic channels consist of a single lumen, which does not permit preservation of microstructural organization of nerve fibers and growing axons.[9] This, in turn, may result in limited or erroneous innervation of distal targets impeding functional recovery and resulting in formation of painful neuropathies.

To preserve the nerve fiber topography during growth, scaffolds containing multiple individual microchannels have been produced via molding, extrusion, freeze drying, three-dimensional (3D) printing, electrospinning, or photolithography. The enhanced ability of such multichannel scaffolds to preserve directionality of growing neuronal processes has been corroborated in rodent models of peripheral nerve and spinal cord injury. Despite the successes of microchannel scaffolds in research models, their translation to clinical use remains impeded by several technological barriers. First, a fabrication technique compatible with a wide range of materials is required to optimize the scaffolds mechanical and chemical properties for enhanced biocompatibility and improved nerve growth. Second, to enable the transport of nutrients, oxygen and waste, materials constituting the scaffold walls should support interconnected porosity. Third, the scaffold geometry should resemble the structural complexity of the injured nerve. Fourth, to facilitate translation of synthetic scaffolds from bench to bedside, these devices must be reproducibly manufactured at lengths corresponding to clinically observed nerve gaps with a diversity of cross-sectional dimensions and geometries.

To overcome these technical barriers, introduced here is a high-throughput fabrication technique that delivers microchannel scaffolds with flexibility over constituent materials and device dimensions and controlled porosity and digitally pre-defined geometries. The method employs on thermal drawing of macroscopic multi-material models, preforms, into micro-structured multifunctional fibers. Preforms with centimeter-scale lateral dimensions and lengths, composed of multiple materials with similar glass transition ($T_g$) and melting ($T_m$) temperatures can be produced via conventional machining and assembly techniques, and then drawn into tens to thousands of meters of fibers with micro-scale lateral dimensions and cross-sectional geometries matching those of the preforms. Although thermal drawing readily delivers microscale devices at high yield, fabrication of porous structures via this method poses a challenge, as pores cannot be programmed at the preform level. Porosity in thermally drawn fibers was recently achieved by leveraging thermally induced phase segregation of a polymer-solvent mixture. This approach, however, imposes restrictions on materials selection and couples pore dimensions to the polymer and solvent properties.

To expand the use of fiber drawing to a wide array of thermoplastics and to precisely control pore sizes, a porogen (sodium chloride, NaCl) is loaded into polymers prior to the preform fabrication (FIG. 9B). NaCl crystals with the desired dimensions were obtained via filtration and mixed with solutions of thermoplastics that were then cast into films of defined thickness by doctor-blading. For each device, the composite polymer-NaCl films were then rolled around a mandrel of a sacrificial material with a $T_g$ close to that of the polymer composite and consolidated under heat. The resulting structures were inserted into a sacrificial cladding of the material matching that of the sacrificial core and thermally drawn into tens of meters of micro-structured fibers with circular and rectangular cross-sections (FIGS. 9C-9I). Following thermal drawing, the sacrificial polymer cladding and core and the NaCl crystals were sequentially dissolved by selective chemical etching resulting in porous microchannels with linear dimensions defined by the preform geometry and drawing parameters (FIGS. 9D-9I). Lateral dimensions of the microchannels could be tuned by varying the stress on the fiber during thermal drawing (FIGS. 9J-9M). The thermally drawn composite fibers could then be 3D fuse printed into complex geometries (FIGS. 9N-9P).

As this approach is largely agnostic to the chemistry of the thermoplastic, it was applied to polycaprolactone (PCL) and polylactic acid (PLA) both of which are ubiquitously used in tissue engineering. Tens of meters of hollow PCL and PLA constructs with circular and rectangular cross-sections, inner core dimensions ranging between 50 µm and 3 mm, and wall thicknesses tunable between 20 µm and 1 mm were produced (FIGS. 10A-10F, 13A-13B).

Pore dimensions and their distribution corresponded to those of the NaCl porogen crystals embedded within the polymer matrix (FIGS. 10G, 10H). To enable fluid exchange between the neurites growing within the fiber scaffolds and the exterior environment, while avoiding non-directional growth through the pores, the dimensions of the latter should be <100 µm. To further prevent the neuronal migration through the pores NaCl crystals with a size of 11.4±5.26 µm (mean±standard deviation) were selected as a porogen. To obtain interconnected porosity, numerical analysis estimated the percolation threshold with highly irregular particles (20 faces particle) of similar dimensions to be approximately 30%. It was discovered that, while it was possible to produce thermally drawn PCL filaments with porosity exceeding 45 vol %, such structures could not be easily handled or fuse printed. The PCL filaments with 35 vol % porosity, however, were mechanically robust and suitable for fuse printing.

To verify interconnected porosity and to determine the time necessary for complete salt removal, elemental dispersion X-ray (EDX) analysis was applied to the PCL channels fabricated with 35 vol % salt. Sacrificial claddings and inner cores were dissolved from 1 cm-long sections of cylindrical PCL channels with an inner diameter of 300 µm and wall thickness of 78 µm. The EDX analysis was performed on the midline cross-sections (0.5 cm from each end) of the channels, revealing an average of 20.7% and 96.9% removal of salt following 1 hour and 24 hours in water bath, respectively (FIGS. 10I-10N). In addition, as theoretically predicted and experimentally reported for PCL films, introducing pores reduced the elastic moduli of PCL channels. Tensile testing of PCL channels indicated a decrease in the elastic moduli from 294.3 kPa for solid PCL to 70.0 kPa for PCL with 35 vol % porosity.

While microscale single lumen channels enable nerve guidance in vitro, they have limited utility in repairing nerves with complex architectures in vivo. Consequently, it was sought to produce porous scaffolds with multiple inner channels with complex targeted outer geometries, without restrictions on length or cross-sectional dimensions. This was accomplished by applying a filament surface heating technique to 3D print the thermally drawn conduits into digitally-defined shapes. Akin to thermal drawing, filament surface heating can be applied to a broad range of thermoplastics enabling the combinatorial processing of materials via sequential use of the two techniques.

Prior to fuse printing of scaffold structures, the sacrificial polystyrene cladding was chemically etched off the PCL fibers to produce hollow channels. The NaCl crystals, however, were left within the polymer matrix to avoid potential collapse of the pores during the surface heating. The conduits were then fed into a printing nozzle where the surface heating occurred, which resulted in the fusion of adjacent microchannel fibers (FIG. 14). The printed structures were then subjected to salt-leaching to produce multichannel microporous scaffolds at centimeter scales. To illustrate the utility of this approach to produce complex structures, multichannel scaffolds were printed with cross-sectional geometries mimicking that of the spinal cord cross-section as well as bifurcated scaffolds that could potentially be applied to bridge transected branched nerves (FIGS. 11A, 11B, 15A). Following salt leaching, scanning electron microscope (SEM) images of the fuse-printed scaffolds revealed their porous walls analogous to those of the individual fiber channels (FIGS. 11C, 11D).

To evaluate the utility of the porous microchannel fibers as conduits for nerve growth, their stability was first evaluated in physiological conditions. Scaffold shapes and pore sizes were maintained over 28 days in phosphate buffered saline under gentle agitation at 37° C. (FIGS. 11E, 11F, 15B). Furthermore, an AlamarBlue® cytotoxicity assay applied to human embryonic kidney (HEK293) cells cultured in media containing the scaffolds did not reveal any adverse effects on the cell viability (FIGS. 16A-16E).

The necessity of porous walls for nerve growth within scaffold channels is widely accepted in tissue engineering as the porosity facilitates adequate nutrient, waste, and oxygen exchange between the tissue and the local environment. It was sought to evaluate the effects of porosity on nerve growth within our thermally drawn microchannels in vitro. Consistent with prior studies, primary neonatal rat dorsal root ganglia (DRGs) were used as an in vitro model of peripheral nerve growth within the scaffolds. Isolated DRGs were cut in half, and placed at the edges of porous and non-porous thermally drawn PCL channels coated with Matrigel™. Twelve days following seeding, DRGs placed within the porous channels exhibited longer processes than those placed within non-porous structures as revealed by neurofilament (NF) immunostaining ($p<0.05$; post-hoc Tukey HSD test), FIGS. 12A, 12B). Consistent with prior reports, the migration and growth of Schwann cells, as quantified by S-100 immunostaining, accompanied neurite extension (FIGS. 17A-17Q). To test if the nerve growth was reduced within non-porous channels due to lower mass transport or due to the differences in surface morphology, DRGs were also cultured on Matrige™-coated porous and non-porous PCL films and glass coverslips as controls submerged in media with no restrictions on mass transport. In contrast to the findings for nerve guidance channels, similar growth ($p>0.05$; post-hoc Tukey HSD test) was observed for both films (FIGS. 12C, 12D, 17A-17Q, 18), which suggested that mass transport played a more significant role in confined environments. In both porous and non-porous channels the neurite outgrowth from DRGs extended significantly beyond the lengths observed for DRGs seeded on films ($p<0.05$; post-hoc Tukey HSD test, FIG. 12E).

The combination of fiber drawing and salt-leaching enabled high-throughput fabrication of nerve guidance channels with controlled porosity, stiffness, and dimensions from different thermoplastics. These porous fiber-based channels were further arranged into complex scaffold geometries via filament surface heating fuse printing. As the latter method takes advantage of digital design, it may enable fabrication of personalized patient-specific scaffolds based on the structural images of injured nerves. This scalable approach for producing porous structures with pre-defined geometries and lengths may find additional applications outside tissue engineering including fluid filtration and chemical separation.

Conduit Fabrication Via Thermal Drawing:

NaCl (Alfa Aesar) was ground using an automatic ceramic mortar and pestle (Fritsch). Nylon filter meshes with sizes of 28, 50, 79 and 101 µm (McMaster) were then used to select salt particles with size ranges of <28 µm, 28-50 µm, 50-79 µm and 79-101 µm by first shaken dry over the smaller size mesh and then the mesh with the upper size, when applicable. PCL (MilliporeSigma) was dissolved in chloroform to form a 3 wt. % solution. PLA (GoodFellow) was dissolved in a 50:50 volume ratio chloroform and dichloromethane and a 4 wt % solution was obtained. The polymer solutions were mixed with salt at the desired size range and volume percentages (up to 65 vol % salt) using a vortex (VWR). A T-shape aluminum (Al) piece was machined to a blade with a height of 1 mm for doctor blading. Polymer/salt mixtures were poured on a copper sheath for PCL and glass for PLA, and the Al blade was passed over the mixtures. The films were air-dried for at least 10 min for PCL and 30 min for PLA prior to removal. Film removal was aided by applying ethanol to the films. The solvents were removed in vacuum for over 24 hours and 48 hours for PCL and PLA, respectively. The films were wrapped around polystyrene (PS; McMaster) with circular or square cross-sections and covered with a Teflon sheath which was then tightly taped. A uniform piece was obtained by consolidating the films around the rod in an oven at the following temperatures for 30 min: 100% PCL at 63° C., PCL/salt at 70° C., 100% PLA at 73° C., and PLA/salt at 80° C. The consolidated rods, were then placed inside a 25.4 mm diameter PS rod after machining it to have a hole in the middle with the size of the outer diameter of the consolidated rod (between 4 mm to 9 mm). For square cross-section fibers, machined PS slabs with consolidated PCL/PS pieces were placed in a press at 100° C. for 1 hour and then, while preserving the temperature, a pressure of 50 psi was applied for 1 hr. The preform was then air cooled to room temperature under pressure. During thermal drawing, preforms were vertically suspended inside a furnace at 220° C. for PCL and 240° C. for PLA. To remove the PS, conduits were placed in cyclohexane under gentle agitation (<50 rotation per minute) overnight. The samples were then first rinsed with ethanol (VWR) and then placed in water for at least 24 hours to remove the salt.

Conduit Characterization:

Conduits were cut with razor blades and coated with 3 nm of gold particles and imaged with SEM (Model 6010LA; JOEL). Salt and pore size quantification were done with ImageJ software. For EDX analysis, thermally drawn PCL conduits with 35 vol % salt and an inner diameter of 0.3 mm were cut to 10 mm in length. After etching the PS in cyclohexane overnight, the samples were used as they were or rinsed with ethanol and placed in water for 1 or 24 hr. All samples were cut in half, gold coated and assessed for NaCl presence using EDX (Model 6010LA; JOEL) (n=3). Tensile testing was done on non-porous and 35 vol % porous PCL conduits of 15 mm in length and 0.3 mm inner diameter in a Dynamic Mechanical Analyzer (Model DMA Q800; TA Instruments) under a constant extension rate of 0.2 mm/min (n=5) until conduit breakage.

Fuse Printing Microchannel Scaffolds and Analysis:

PCL fibers with 35 vol % porosity were thermally drawn as described above. About 5-7 m of the fibers with 0.3 mm inner diameter were placed in cyclohexane for 12 hr, with the solution changed three times for the outer polystyrene to be completely removed, while the inner polystyrene was only partially removed. The fibers were subsequently fed into a printing nozzle. The nozzle contained a short stainless steel hot end with a length of 0.3 mm to heat the fibers. The diameter of the hot end was 0.8 mm, which corresponded to the fiber outer diameter of 0.7-0.8 mm. The hot end temperature was 165-175° C., measured by a VWR thermocouple probe. The feeding speed was 100-120 mm/min. The PCL fibers were printed onto an underlying PCL film (thickness of 0.2 mm) for adhesion of the first printed layer to the print bed. The input layer height was set as the diameter of the fiber. The three-dimensional design of the porous scaffold was drawn in Solidworks and was later processed by Slic3r to create a gcode for printing. The gcode of the printed scaffold was then read by Pronterface software, which communicated the required XYZ print positions to the 3D-printer (Rova3D Multinozzle printer). The scaffold characterization and quantifications were done via SEM imaging and imageJ, respectively. Cytotoxicity tests were done via AlamarBlue® (ThermoFisher) assays on HEK cells following the manufacturer's protocol.

DRG Isolation:

All animal handling and procedures were approved by the MIT Committee on Animal Care and were in compliance with the National Institutes of Health Guide for the Care and Use of Laboratory Animals. DRGs were isolated from Sprague Dawley neonatal rats on postnatal day 1 (Charles River). Individual DRG explants were collected from the spinal column, and the nerve roots and connective tissue were removed from the DRGs.

In Vitro Setup and Immunohistochemistry:

Non-porous and 35 vol % porous PCL conduits were sectioned to 10 mm in length. After the polystyrene and salt were removed as described above, the conduits and PCL films with similar porosities to those of conduits were placed in ethanol and set in the biosafety cabinet under UV for 45 min. Maintaining the samples sterile, ethanol was replaced with sterilized phosphate buffer saline (1×DPBS) and exchanged three times, letting it rest for 15 min each time, and then air-dried. In vitro studies were performed similar to a previous study.

Briefly, samples were coated with Matrigel™ by applying reduced growth factor Matrigel™ (BD Biosciences) at a 1:30 dilution with a DRG medium (Neurobasal-A media supplemented with B-27 and glutamax; Life Technologies) for an hour at room temperature. The coated conduits and films were placed in a DRG medium in 24-well, non-tissue culture plates (VWR Scientific Products) for at least 2 hr. During this time, air bubbles were pressed out of the conduits using sterile tweezers. For the control experiments, 12-mm glass coverslips (Electron Microscopy Sciences) etched overnight in 10% hydrochloric acid solution (Sigma) and stored in 99% ethanol were used. The coverslips were dried over a flame and placed into 24-well plates and coated with Matrigel™ as described above. The isolated DRGs were sectioned in half and either placed inside the conduits at one end, or in the center of the films/coverslips. The isolated DRGs were sectioned in half and either placed inside the conduits at one end, or in the center of the films. The media was changed every 3-4 days and the cultures were fixed on day 12 with 4% paraformaldehyde (Electron Microscopy Sciences) in 1×DPBS for 40 min. The samples were then rinsed with 1×DPBS and permeabilized with 0.1% Triton X-100 in 1×PBS for 25 min. Goat serum (2.5%) was used to block the samples at 4° C. overnight. Samples were then incubated in 1:500 rabbit anti-neurofilament primary antibody (N4142, MilliporeSigma) and 1:500 mouse anti-S100 (S2657, MilliporeSigma) diluted in 2.5% donkey serum for 2 hours at room temperature, and rinsed 3 times in 1×PBS for fifteen minutes each. Secondary antibody staining was done with 1:1000 goat anti-rabbit Alexa Fluor® 633 IgG (A21070, Life Technologies) and 1:1000 goat anti-mouse Alexa Fluor® 568 IgG (A11004, Life Technologies) for 2 hr, followed by three washes in 1×DPBS of fifteen minutes each.

To stain the nuclei, the samples were then incubated with 30 μM 6-diamidino-2-phenylindol (DAPI) (Life Technologies) for 2 min and washed with 1×DPBS three times. The samples were mounted on glass slides with VECTASHIELD® mounting medium containing 6-diamidino-2-phenylindol (DAPI; VWR). Slides were imaged with a confocal microscope (Olympus FV1000 laser scanning confocal microscope). The maximum length of neurite growth from the center of the ganglia at the edge of the channels were used for analyzing growth in channels. Neurite growth length on the films was determined as the average radius of the neurite growth from the center of the ganglia to the end points generated by 72 cross-sectional lines with 5° spacing. Neurite extension were quantified via ImageJ. Statistical analysis was done in Python.

Example 2—Stem Cell Differentiation for Muscle Regeneration

FIGS. 19A-19F illustrate application of porous scaffolds to muscle generation. In particular, iMPC is incorporated with the porous films or porous fibers an implanted for treatment of volumetric muscle loss (VML) injury mouse model. It is seen that such porous scaffolds improve regeneration of muscles. FIGS. 20A-20G illustrate the functional improvement see in the VML injury mouse model.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method of manufacturing a hollow porous fiber, comprising:
   combining salt particles with a thermoplastic to generate a film;
   rolling the film onto a core substrate to create a preform;
   inserting the preform into a cladding;
   drawing a fiber from the preform at a temperature above a glass transition temperature of the thermoplastic, of the cladding, and of the core substrate, and below a melting temperature of the salt particles; and
   removing the salt particles, the core substrate, and the cladding from the fiber to generate the hollow porous fiber.

2. The method of claim 1, wherein the combining includes:
   combining the salt particles with a solution including the thermoplastic dissolved in a solvent to generate a salt-thermoplastic solution;
   casting the salt-thermoplastic solution onto a surface;
   blading the salt-thermoplastic solution into the film having a predetermined thickness; and
   evaporating the solvent from the film.

3. The method of claim 1, wherein the cladding and the core substrate are composed of the same material.

4. The method of claim 1, the removing further comprising stretching the fiber to remove the cladding and the core substrate, the method further comprising depositing the fiber in a predetermined arrangement.

5. The method of claim 4, the depositing the fiber in the predetermined arrangement including depositing the fiber as a set of filaments that are stacked together.

6. The method of claim 5, the depositing the fiber including heating the fiber above a glass transition temperature of the thermoplastic, such that the filaments in the set of filaments fuse together upon stacking during deposition.

7. The method of claim 5, further comprising:
   trimming the ends of one or more filaments of the set of filaments to expose an inner core of that filament generated by the removal of the core substrate, to generate a tissue scaffold.

8. The method of claim 7, wherein the removing the salt particles from the fiber includes leaching the salt particles from the set of filaments of the tissue scaffold.

9. The method of claim 4, wherein the predetermined arrangement is one of a butterfly shape and a branch shape.

10. The method of claim 1, the removing the salt particles including leaching the salt particles from the fiber.

11. The method of claim 1, further comprising, prior to combining the salt particles with the thermoplastic:
   filtering the salt particles with a filter having a pore size corresponding to a target pore size for the porous fiber to obtain filtered salt particles of the same size or smaller than the pore size.

12. The method of claim 11, wherein the target pore size is from about 0.1 µm to about 500 µm.

13. The method of claim 1, wherein the thermoplastic is selected from the group consisting of polycaprolactone (PCL) and polylactic acid (PLA).

14. The method of claim 1, wherein the salt particles are composed of sodium chloride.

15. The method of claim 1, wherein removal of the core substrate results in formation of an inner core in the fiber, the drawing including drawing at a drawing rate such that the inner core of the fiber has a diameter of from about 50 µm to about 3 mm.

16. The method of claim 1, the drawing including drawing at a drawing rate such that a porous wall of the fiber has a thickness of from about 20 µm to about 1 mm.

17. The method of claim 1, the combining the salt particles with the thermoplastic including combining the salt particles with the thermoplastic in a volume/volume ratio such that the porous fiber has a porosity of from about less than 1% to about 45%.

* * * * *